US012582820B2

(12) United States Patent
Covalin et al.

(10) Patent No.: US 12,582,820 B2
(45) Date of Patent: Mar. 24, 2026

(54) NEUROSTIMULATION THERAPY FOR TREATING UTERINE BLEEDING

(71) Applicant: Spark Biomedical, Inc., Dallas, TX (US)

(72) Inventors: Alejandro Covalin, Los Angeles, CA (US); Christopher Czura, Oyster Bay, NY (US); Navid Khodaparast, Dallas, TX (US)

(73) Assignee: SPARK BIOMEDICAL, INC., Dallas, TX (US)

( * ) Notice: Subject to any disclaimer, the term of this patent is extended or adjusted under 35 U.S.C. 154(b) by 0 days.

(21) Appl. No.: 19/002,188

(22) Filed: Dec. 26, 2024

(65) Prior Publication Data

US 2026/0007885 A1      Jan. 8, 2026

Related U.S. Application Data

(60) Provisional application No. 63/667,930, filed on Jul. 5, 2024.

(51) Int. Cl.
A61N 1/04          (2006.01)
A61N 1/05          (2006.01)
A61N 1/36          (2006.01)

(52) U.S. Cl.
CPC ....... A61N 1/36021 (2013.01); A61N 1/0456 (2013.01); A61N 1/0551 (2013.01); A61N 1/36017 (2013.01)

(58) Field of Classification Search
CPC ............................ A61N 1/0551; A61N 1/0456
See application file for complete search history.

(56) References Cited

U.S. PATENT DOCUMENTS

| | | | |
|---|---|---|---|
| 6,735,476 B2 | 5/2004 | Mellen | |
| 7,657,310 B2 | 2/2010 | Buras | |
| 7,711,432 B2 | 5/2010 | Thimineur et al. | |
| 8,729,129 B2 | 5/2014 | Tracey et al. | |

(Continued)

FOREIGN PATENT DOCUMENTS

WO      WO2021011165 A1      1/2021

OTHER PUBLICATIONS

Spark Biomedical, Inc., "Transcutaneous Auricular Neurostimulation (tAN™) to Aid in the Reduction of Symptoms Associated With Opioid Withdrawal", Sparrow Clinical Whitepaper, Version: MKT-005-V1, 2021, 8 pages.

(Continued)

*Primary Examiner* — Alyssa M Alter
(74) *Attorney, Agent, or Firm* — Finch & Maloney PLLC

(57)          ABSTRACT

In an illustrative embodiment, methods and systems for treating uterine bleeding include applying, at least every other day in which a subject exhibits or is expected to exhibit menstrual bleeding, neurostimulation therapy in one or more sessions, each session having a duration of at least five minutes, the neurostimulation therapy including applying electrical neurostimulation or mechanical neurostimulation to directly and/or indirectly activate one or more neural targets, the one or more neural targets including a trigeminal cervical complex and/or vagal efferent fibers. The neurostimulation therapy may be configured to enhance platelet function of the subject, thereby reducing a total volume of blood loss over a course of the menstrual bleeding.

19 Claims, 30 Drawing Sheets

(56)                References Cited

U.S. PATENT DOCUMENTS

| | | | |
|---|---|---|---|
| 9,089,719 | B2 | 7/2015 | Simon et al. |
| 9,925,373 | B2 | 3/2018 | Nirenberg |
| 10,463,854 | B2 | 11/2019 | Perez |
| 10,537,703 | B2 | 1/2020 | Tyler et al. |
| 10,786,666 | B2 | 9/2020 | Chu et al. |
| 10,912,712 | B2 | 2/2021 | Tracey et al. |
| 11,260,229 | B2 | 3/2022 | Manogue |
| 2005/0065574 | A1 | 3/2005 | Rezai |
| 2009/0287035 | A1 | 11/2009 | Dietrich et al. |
| 2014/0135886 | A1 | 5/2014 | Cook et al. |
| 2014/0206945 | A1 | 7/2014 | Liao |
| 2015/0335876 | A1 | 11/2015 | Jeffery et al. |
| 2019/0134390 | A1 | 5/2019 | Shimada et al. |
| 2019/0321623 | A1 | 10/2019 | Huston et al. |
| 2020/0094055 | A1* | 3/2020 | Manogue ............. A61N 1/0456 |
| 2020/0238085 | A1 | 7/2020 | Khodaparast et al. |
| 2021/0213286 | A1 | 7/2021 | Covalin et al. |
| 2022/0192580 | A1 | 6/2022 | Toth et al. |
| 2022/0212012 | A1 | 7/2022 | Manogue |
| 2022/0305260 | A1 | 9/2022 | Covalin et al. |

OTHER PUBLICATIONS

Bennett, John A., et al. "Acetylcholine Inhibits Platelet Activation", The Journal of Pharmacology and Experimental Therapeutics, May 2019, 182-187.

Rosas-Ballina, Mauricio, et al., "Acetylcholine-Synthesizing T Cells Relay Neural Signals in a Vagus Nerve Circuit", Science, Oct. 2011, 334(6052); 98-101.

Schedel, Angelika, et al., "Human Platelets Express Functional alpha7-Nicotinic Acetylcholine Receptors", Arterioscler Thromb Vasc Biol, Apr. 2011, 928-934.

Nettle, "A New Care Pathway for Menstrual Health", http://www.samphireneuro.com/nettle/health-care-providers, accessed Nov. 5, 2024, 16 pages.

Sara, Susan J., et al., "Orienting and Reorienting: the Locus Coeruleus Mediates Cognition Through Arousal", Neuron 76, Oct. 2012, Elsevier Inc., 130-141.

Abbasian, Nima, et al., "Supramaximal Calcium Signaling Triggers Procoagulant Platelet Formation", Blood Advances, Dept. of Pharmacology and Dept. of Biochemistry, Universit of Cambridge, Cambridge, UK, Jan. 2020, vol. 4, No. 1, 154-164.

Dobryakova, Ekaterina, et al., "The Dopamine Imbalance Hypothesis of Fatigue in Multiple Sclerosis and Other Neurological Disorders", Frontiers in Neurology, Mar. 2015, vol. 6, Article 52, 1-8.

McLagan, Bailey, et al., "The Role of Transcutaneous Electrical Nerve Stimulation for Menstrual Pain Relief: a Randomized Control Trial", Women's Health, vol. 20, 1-10; The Aurthor(s) 2024.

Steidel, Kenan, et al., "Transcutaneous Auricular Vagus Nerve Stimulation Influences Gastric Motility: a Randomized, Double-Blind Trial in Healthy Individuals", Elsevier, Brain Stimulation, 2021, 1126-1132.

Elboim-Gabyzon, Michal, et al., "Transcutaneous Electrical Nerve Stimulation (TENS) for Primar Dysmenorrhea: an Overview", International Journal of Women's Health, Dovepress, 2020:12, 1-10.

Bravo-Iniguez, Carlos E., et al., "Vagus nerve stimulation primes platelets and reduces bleeding in hemophilia A male mice", Nature Communications, Jun. 2023, 12 pages.

Invitation to Pay Additional Fees and, Where Applicable, Protest Fee, received in International Application No. PCT/US2025/033989, mailed Sep. 4, 2025, 5 pages.

* cited by examiner

Figure 4:
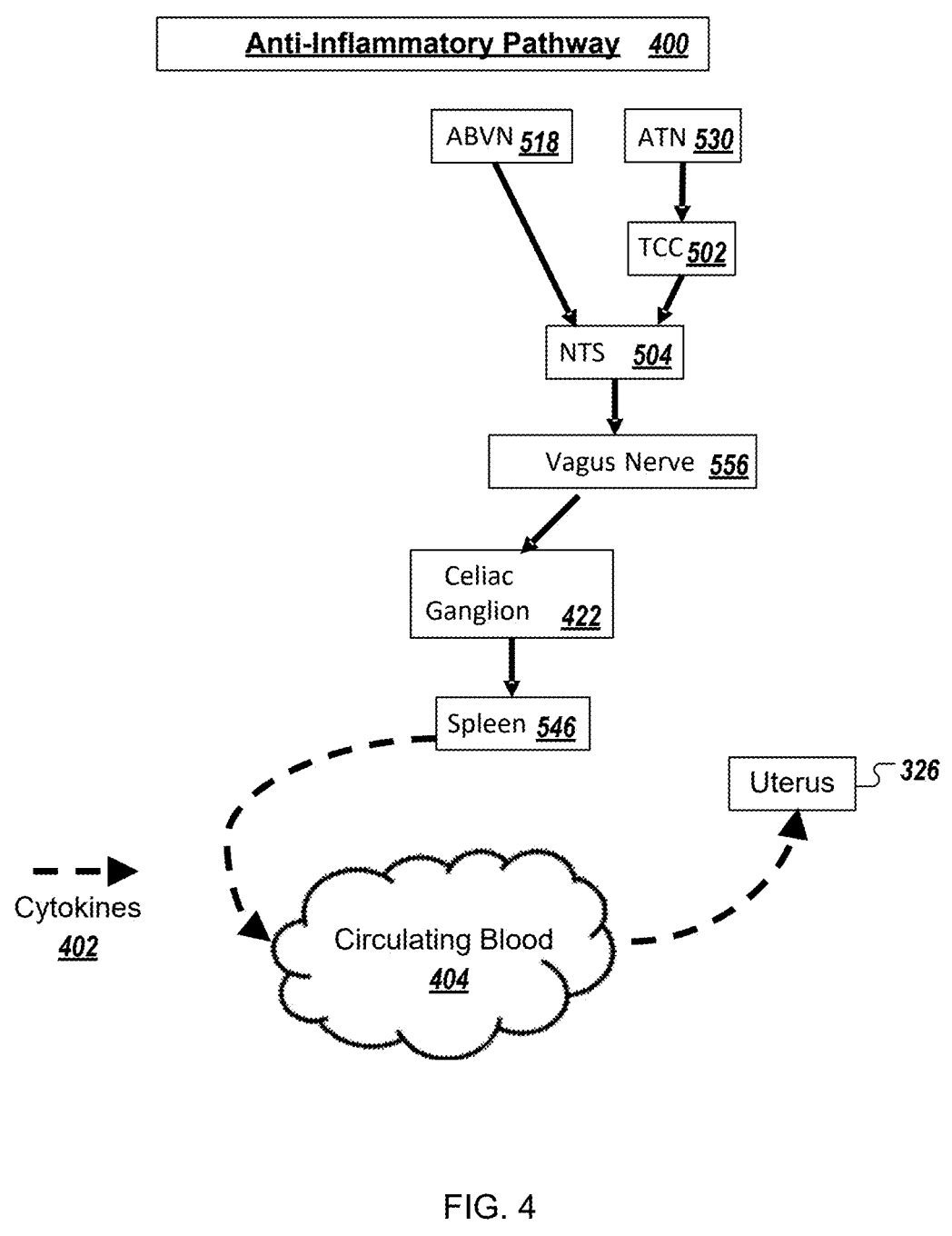

Anti-Inflammatory Pathway 400

ABVN 518

ATN 530

TCC 502

NTS 504

Vagus Nerve 556

Celiac Ganglion 422

Spleen 546

Uterus 326

Cytokines 402

Circulating Blood 404

Uterus Vasodilation Intervention

518

First Stimulation | ABVN

502

TCC

530

ATN | Second Stimulation

504

NTS

510

PAG

Uterus
Parasympathetic
Pathway
300

Ach Release
702

Uterus
326

*1530*

Hemostatic pathways

2040

1

NEUROSTIMULATION THERAPY FOR TREATING UTERINE BLEEDING

RELATED APPLICATIONS

This application claims priority to U.S. Provisional Patent Application 63/667,930 entitled "Neurostimulation Therapy for Treating Women's Health Conditions" and filed Jul. 5, 2024. This application is related to the following prior patents and patent applications by Spark Biomedical directed to stimulation therapies and stimulation devices: U.S. Pat. No. 10,967,182 entitled "Devices and Methods for Reducing Inflammation Using Electrical Stimulation" and issued Apr. 10, 2021; U.S. Pat. No. 11,351,370 entitled "Devices and Methods for Treating Cognitive Dysfunction and Depression Using Electrical Stimulation" and issued Jun. 7, 2022; U.S. patent application Ser. No. 18/583,160 entitled "Electrical Stimulation Methods and Devices for Improving Blood Management and filed Feb. 21, 2024, and U.S. Pat. No. 12,029,893 entitled "Wearable Auricular Neurostimulator and Methods of Use" and issued Jul. 9, 2024. The contents of each of the above-noted reference is hereby incorporated by reference in its entirety.

BACKGROUND

It is no secret that, compared to that of male's, women's health has been neglected. Neglected in the sense that for centuries the vast majority of medical research had been done with male participants, and up the mid 1800's there were practically no women physicians. In fact, in 1849, Elizabeth Blackwell was the first women to graduate from a medical school in the United States. Researchers excluded women as subjects in medical research mostly due to the level of complexity that the female hormonal cycle adds to the interpretation of research results. In fact, in 1977 the Food and Drug Administration (FDA) policy recommended excluding women of childbearing potential from Phase I and early Phase II drug trials. This lack of inclusion of women participants in medical research led to tragic consequences, such as it was the case of the use of thalidomide, which resulted in babies being born with serious deformation. It was not until the 1989 that the National Institutes of Health (NIH) recommended the inclusion of women as participants in medical research, and it was not until 1993 that the inclusion of women became mandatory on any NIH funded study.

It is likely this combination of a lack of female physicians along with the lack of women subjects participating in medical research that has led to the present lag in women's health. It is interesting to note that it is precisely the hormonal cycle, that which the researchers wanted to avoid, that is one of the main contributors to the need to fine tune gender-based medical protocols. Solutions that were optimized for males may or may not be optimal for females.

A large majority of women experiencing regular menstrual cycles suffer some degree of pre-menstrual syndrome (PMS). In fact, up to 75% of women have reported having some PMS symptoms, even more (~90%) if only bloating and headaches (including migraines) are considered. A small percentage (3% to 8%) of women suffer a severe form of PMS known as premenstrual dysphoric disorder (PMDD). PMS symptoms in women can include affective and cognitive/behavioral symptoms as well as physical symptoms. PMS can manifest, in some examples, as irritability and/or hostile behavior, feeling tired, sleep problems (e.g., sleeping too much or too little), appetite changes and/or food cravings, trouble with concentration and/or memory, tension and/or anxiety, depression, feelings of sadness and/or crying spells, mood swings, and/or a reduction in sexual desire. Some of the most common physical symptoms include joint pain, swollen and/or tender breasts, constipation or diarrhea, bloating and/or a gassy feeling, cramping, headache and/or backache, clumsiness, and lower tolerance for noise and/or light. See, e.g., Winer, Sharon A., and Andrea J. Rapkin. "Premenstrual disorders: prevalence, etiology and impact." The Journal of reproductive medicine 51.4 Suppl (2006): 339-347. For the purpose of the present disclosure, reference to headache implicitly includes menstrual-related migraine.

Dysmenorrhea, defined as painful menstruation, in particular pain in the pelvic area in the form of painful cramps occurring during menstruation, is triggered by the increase in uterine contractility. This increase in contractility leads to vasoconstriction, limiting blood flow and producing a level of ischemia triggering the painful cramps. In the absence of a pelvic pathology, dysmenorrhea is known as primary dysmenorrhea. In the presence of pelvic pathology, dysmenorrhea is categorized as secondary dysmenorrhea, for example in the case of endometriosis or adenomyosis. Dysmenorrhea is a very common gynecological condition among menstruating women which negatively affects the quality of life of those who suffer it. Despite being suffered by a large percentage of women, dysmenorrhea has been poorly treated, and even disregarded, by health professionals. Up to a third of women experience severe debilitating dysmenorrhea, as stated, in the form of menstrual cramps. In cases of severe pain, women may at times miss up to three days of work/school each menstrual cycle. The impact, however, goes beyond lost productivity. It disrupts daily activities, hinders academic performance in young women, disrupts sleep, and can contribute to anxiety and depression. Furthermore, dysmenorrhea has been associated with the risk of central sensitization leading to stronger pain sensation potentially for life. Therefore, it is of primal importance to control and lower menstrual pain, in particular in those cases in which pain levels are high.

Preeclampsia is a vascular problem that some pregnant women suffer. Preeclampsia can also occur several weeks after delivery. Preeclampsia is defined as new-onset maternal hypertension accompanied by cardiovascular, renal, and/or neural abnormalities presenting in the second half of pregnancy.

Postural orthostatic tachycardia syndrome (POTS) affects between half a million and three million individuals in the United States. As presently understood, it affects mostly white women of childbearing age. POTS symptoms manifest after the person stands up, (e.g., after assuming an upright position). Common symptoms include, in some examples, palpitations, syncope, presyncope, tremor, diaphoresis, chest pain, limb edema, venous pooling, Raynaud's phenomenon, increased urinary frequency, nocturia, bladder dysfunction, nausea, vomiting, diarrhea, bloating, abdominal pain, constipation, gastroparesis, muscle weakness, muscle pain, joint pain, joint dislocation/hypermobility, lightheadedness, dizziness, vertigo, headache, weakness, visual blurring, brain fog/cognitive disturbance, fatigue, sleep disturbance, heat intolerance, menorrhagia, polycystic ovary syndrome (PCOS), anxiety, and attention deficit/hyperactivity disorder (ADHD).

Polycystic ovary syndrome (PCOS) is characterized by elevated levels androgen and menstrual irregularities, as well as, in some cases, the existence of small cysts on at least one of the ovaries. PCOS can be mainly manifested biochemically (e.g., high androgen levels-a.k.a. hyperandrogenemia), or it can be mainly morphological (polycystic ovaries). PCOS is one of the main causes of infertility, and, given it presents as a hormonal imbalance, PCOS can lead to several other conditions.

In the United States, PCOS affects approximately 5 million women of reproductive age, leading to a yearly cost to the healthcare system of about $4 Billion USD. Overall, it is estimated that between 5% and 10% of women ages from 18 to 44 suffer from PCOS. The World Health Organization (WHO) estimated that 70% of worldwide affected women are undiagnosed. Females with PCOS are at higher risk of developing, among other ailments, type-2 diabetes, several cardiovascular conditions, endometrial cancer, and dyslipidemia. Symptoms of PCOS include, in some examples, infertility, alopecia, pelvic pain, irregular menstrual cycles, enlarge ovaries with small cysts, hirsutism, and acne.

Approximately 176 million women worldwide suffer from endometriosis. While in endometriosis, endometrial-type tissue is present outside the uterus, in adenomyosis (a.k.a. endometriosis interna), abnormal tissue grows into the uterine muscle. Many of those with endometriosis suffer severe pelvic pain, in particular during periods, sexual intercourse, bowel movements and/or urination. Other common symptoms include chronic pelvic pain, abdominal bloating, nausea, fatigue, and sometimes depression, anxiety, and infertility. In the USA, compared to the average healthcare cost for women, the healthcare cost for women suffering from endometriosis is 63% higher. Furthermore, also in the USA 66% of those women with endometriosis undergo endometriosis-related surgery within 12 months of their diagnosis. In 2009, the yearly healthcare cost in Canada associated with endometriosis was estimated to be $1.8 billion, amounting to an average of $5,200 per patient. A 2008 study performed in ten European countries found the yearly cost per patient to be approximately €10,000, which included loss of productivity. Aside from the large economic burden, endometriosis greatly affects quality of life of those women suffering it.

With an approximated prevalence of between 20% to 35%, adenomyosis is more common than endometriosis; however, due to an estimated large underreporting the true prevalence could be much higher. In more than 10% of the cases, adenomyosis is coincident with endometriosis. Many of the symptoms of adenomyosis are the same as those suffered with endometriosis.

Vasomotor symptoms (VMS) are what is commonly known as hot flashes (a.k.a. hot flushes) and night sweats. VMS usually occur to women in menopause and sometimes in perimenopause; however, VMS can also occur in males. VMS are a form of temperature dysfunction in which the body overreacts to small temperature changes. This overreaction produces a transient heat sensation, flushing, sweating and chills, in some cases accompanied by anxiety. These symptoms can usually last up to five minutes each time and they can occur multiple times per day. More than 80% of women suffer from VMS during menopause, and approximately 50% suffer from it during perimenopause.

While the nervous system primarily controls hormonal cycles, the hormones in circulation interact with the nervous system and, thus, hormonal cycles affect the nervous system response to many different interventions. The inventors recognized a need for new systems and methods designed to ameliorate a variety of women's health-related conditions through neurostimulation, for example by providing therapeutic adjustments to female subject's nervous system responses.

4

SUMMARY OF ILLUSTRATIVE EMBODIMENTS

In one aspect, the present disclosure relates to methods and systems for treating premenstrual syndrome (PMS) and/or premenstrual dysphoric disorder (PMDD) with neurostimulation therapy. The treatments, in some embodiments, may include triggering the release of larger quantities of serotonin (5-HT) in the brain, thereby increasing serotonin availability to ameliorate symptoms of PMS and/or PMDD. The effect of the therapy, for example, may reduce cognitive/behavioral symptoms as well as physical symptoms. The neurostimulation therapy may be applied, for example, via non-invasive auricular neurostimulation applied in close proximity to vagal and/or trigeminal neural fibers.

In some embodiments, bloating/gastrointestinal problems occurring during the pre-menstrual luteal phase may be treated by activating the vagal efferent fibers enervating the gut, thereby increasing gut motility and diminishing bloating and constipation (a.k.a. the PMS belly). The neurostimulation therapy may be applied, for example, via non-invasive auricular neurostimulation applied in close proximity to vagal and/or trigeminal neural fibers.

In certain embodiments, reduced tolerance to noise and/or light occurring during the luteal phase may be treated by activating the trigeminal and/or vagal nerve branches, thereby decreasing the neuronal hypersensitization typical of the luteal phase. The treatment may reduce noise and/or light sensitivity symptoms of PMS migraine. The neurostimulation therapy may be applied, for example, via non-invasive auricular neurostimulation applied in close proximity to vagal and/or trigeminal neural fibers.

In some implementations, sleep disturbances during the luteal phase may be treated using activation of parasympathetic centers to increase the parasympathetic/sympathetic (P/S) ratio, thereby at least partially compensating the typical sympathetic drive exhibited during this phase of the menstrual cycle. The P/S ratio can also be increased via a reduction in sympathetic activity. In some cases, sympathetic activity can be decreased by activating parasympathetic centers, such as, in some examples, the Solitary Nucleus-(NTS), the Nucleus Ambiguus (NA), or the Dorsal Motor Nucleus of Vagus (DMV). By improving the P/S ratio, for example, stimulation therapy may provide more favorable physiological conditions to promote healthy sleep. The neurostimulation therapy may be applied, for example, via non-invasive auricular neurostimulation delivered in close proximity to vagal and/or trigeminal neural fibers.

In one aspect, the present disclosure relates to methods and systems for treating vasomotor symptoms (VMS, a.k.a. hot flashes) with neurostimulation therapy. The treatments, in some embodiments, may include triggering the release of larger quantities of 5-HT and norepinephrine in the brain, thereby modulating hypothalamic thermoregulation. The neurostimulation therapy may be applied, for example, via non-invasive or minimally invasive auricular neurostimulation applied in close proximity to vagal and/or trigeminal neural fibers.

In one aspect, the present disclosure relates to methods and systems for treating dysmenorrhea with neurostimulation therapy. The treatments, in some embodiments, include parasympathetic innervation of the uterus, thereby causing vasodilation in the uterus to counteract and diminish the symptoms of pain and cramping. In some embodiments, the treatments include limiting pain sensation through stimulating the production of endorphins. In further embodiments, the treatment includes altering the parasympathetic/sympathetic ratio of the autonomic nervous system to modulate autonomic function. The neurostimulation therapy may be applied, for example, via non-invasive auricular neurostimulation applied in close proximity to vagal and/or trigeminal neural fibers.

In one aspect, the present disclosure relates to methods and systems for treating preeclampsia with neurostimulation therapy. The treatments, in some embodiments, include triggering spleen activity to produce an anti-inflammatory response, thereby counteracting vasoconstriction in utero-placental tissue. In some embodiments, the treatment includes altering the parasympathetic/sympathetic ratio of the autonomic nervous system to modulate autonomic function. The neurostimulation therapy may be applied, for example, via non-invasive auricular neurostimulation applied in close proximity to vagal and/or trigeminal neural fibers.

In one aspect, the present disclosure relates to methods and systems for treating postural orthostatic tachycardia syndrome (POTS). In some embodiments, the treatments include altering the parasympathetic/sympathetic ratio of the autonomic nervous system to modulate autonomic function. The neurostimulation therapy may be applied, for example, via non-invasive auricular neurostimulation applied in close proximity to vagal and/or trigeminal neural fibers.

In one aspect, the present disclosure relates to methods and systems for treating polycystic ovary syndrome (PCOS). In some embodiments, the treatments include altering the parasympathetic/sympathetic ratio of the autonomic nervous system to modulate autonomic function. The neurostimulation therapy may be applied, for example, via non-invasive auricular neurostimulation applied in close proximity to vagal and/or trigeminal neural fibers.

In one aspect, the present disclosure relates to methods and systems for treating endometriosis and/or adenomyosis. In some embodiments, the treatments include activation of parasympathetic centers to increase acetylcholine, thereby diminishing the proliferation of endometriotic lesions and combatting the lesion producing cycle of endometriosis. The neurostimulation therapy may be applied, for example, via non-invasive auricular neurostimulation applied in close proximity to vagal and/or trigeminal neural fibers.

In one aspect, the present disclosure relates to methods and systems for treating abnormal uterine bleeding, including heavy menstrual bleeding, such as menorrhagia. In some embodiments, the treatments include generating a pressor response by modulating blood flow in the uterus. In some embodiments, the treatments include generating a parasympathetic response, thereby causing vasodilation in the uterus. In some embodiments, the treatments include increasing the coagulation potential. The neurostimulation therapy may be applied, for example, via non-invasive auricular neurostimulation applied in close proximity to vagal and/or trigeminal neural fibers.

In all the above aspects, a minimally invasive treatment may be applied using percutaneous needles. In some embodiments, vagal and/or trigeminal branches can be stimulated non-invasively at locations other than around and on the auricle. In illustration, vagal fibers can be stimulated by placing electrodes on the neck in close proximity to the cervical vagal pathway. In another illustrative example, trigeminal fibers can be stimulated by placing electrodes on the forehead in close proximity to the ophthalmic nerve pathway.

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 4 is a block diagram of an example anti-inflammatory pathway;

DETAILED DESCRIPTION OF ILLUSTRATIVE EMBODIMENTS

Figure 1A:
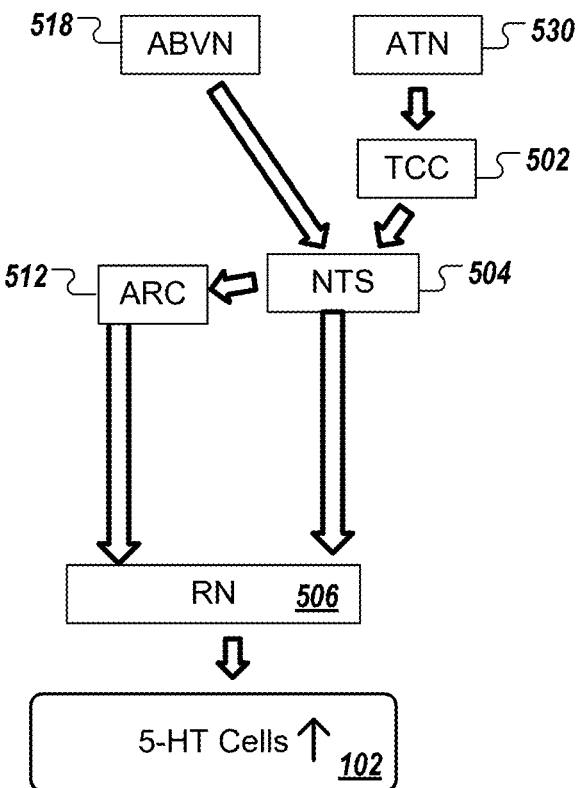
FIG. 1A is a block diagram of an example serotonin availability enhancement pathway.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

The autonomic nervous system (ANS) is controlled by the Central Autonomic Network (CAN), which includes both brainstem and hypothalamic centers or nuclei. Our internal master clock is located within the hypothalamus, in particular, neurons within the hypothalamic suprachiasmatic nucleus (SCN) possess a natural cycle establishing what is known as the circadian rhythm. The cycles are influenced by exposure to light, however, absent the influence of light, the cycles are approximately 25 hours. Thus, many other cycles, such as hormonal cycles, utilize the SCN-run "master clock," as well as additional signals such as hypothalamic activity in other nuclei, to maintain their periodicity. For example, menstrual and sleeping cycles are each controlled by the hypothalamus, in part by the circadian rhythm as well as other hypothalamic nuclei. On top of these hormonal cycles, the hypothalamus also regulates temperature, fluid balance, sexual behavior, metabolism, appetite, weight, insulin, emotions, and short-term memory-all of which are regulated to some extent by different hypothalamic areas. In addition, the hypothalamus also modulates cardiovascular responses as well as enteroendocrine function, the latter by driving the pituitary gland. Pituitary activity is heavily driven by the arcuate nucleus (ARC), another hypothalamic nuclei. This control of the pituitary gland modulates, among other things, the autonomic response to stress as well as the cyclic release of luteinizing hormone (LH) and follicle-stimulating hormone (FSH). Neurons in the preoptic hypothalamic area producing luteinizing hormone-releasing hormone (LHRH) project to the pituitary gland via ARC synapses terminating in the median eminence, where LHRH is delivered to the gonadotropic cells of the anterior pituitary containing the gonadotropin hormones, LH and FSH.

Referring to the ANS in the present disclosure, we include peripheral autonomic regions (e.g., the spinal sympathetic and parasympathetic pre- and post-ganglionic fibers and ganglions), as well as the CAN.

The autonomic nervous system (ANS) is one of the most affected by the variation in hormonal concentration. It is not by chance that many conditions in which the sufferers are primarily or entirely women have a degree of dysautonomia associated with them. For example, as it will be further detailed later, endometriosis is one of these conditions. In the present disclosure, dysautonomia is referred to in a broad sense, including not only situations in which responses to a stimulus are abnormal (e.g., in Postural Orthostatic Tachycardia Syndrome ("POTS")) but also in the situation in which a sympathetic/parasympathetic imbalance is present (e.g., in Vasomotor symptoms (VMS) a.k.a. hot flashes).

There are many conditions suffered by women in which a low parasympathetic/sympathetic ratio (P/S) is present. Such is the case in endometriosis, polycystic ovary syndrome, preeclampsia, pregnancy induced hypertension, and dysmenorrhea amongst others. Interestingly, researchers have suggested that in some cases, autonomic dysfunction maybe one potential cause of female infertility. See Yun, A. Joon, Kimberly A. Bazar, and Patrick Y. Lee. "Autonomic dysfunction may be an under-recognized cause of female fertility disorders." Medical Hypotheses 63.1 (2004): 172-177. Furthermore, many conditions not only associated with women, but in which the majority of sufferers are women, are also associated with a low parasympathetic/sympathetic ratio, for example POTS as well as Raynard's Disease. Other conditions suffered by women that can be ameliorated by changes in ANS activity include menstrual-related migraine. By means of modulating ANS activity, embodiments of the present disclosure address several women-related unmet medical needs. Modifying the P/S ratio, for example, is discussed below in relation to FIG. 6.

PMS and PMDD

Figure 5:
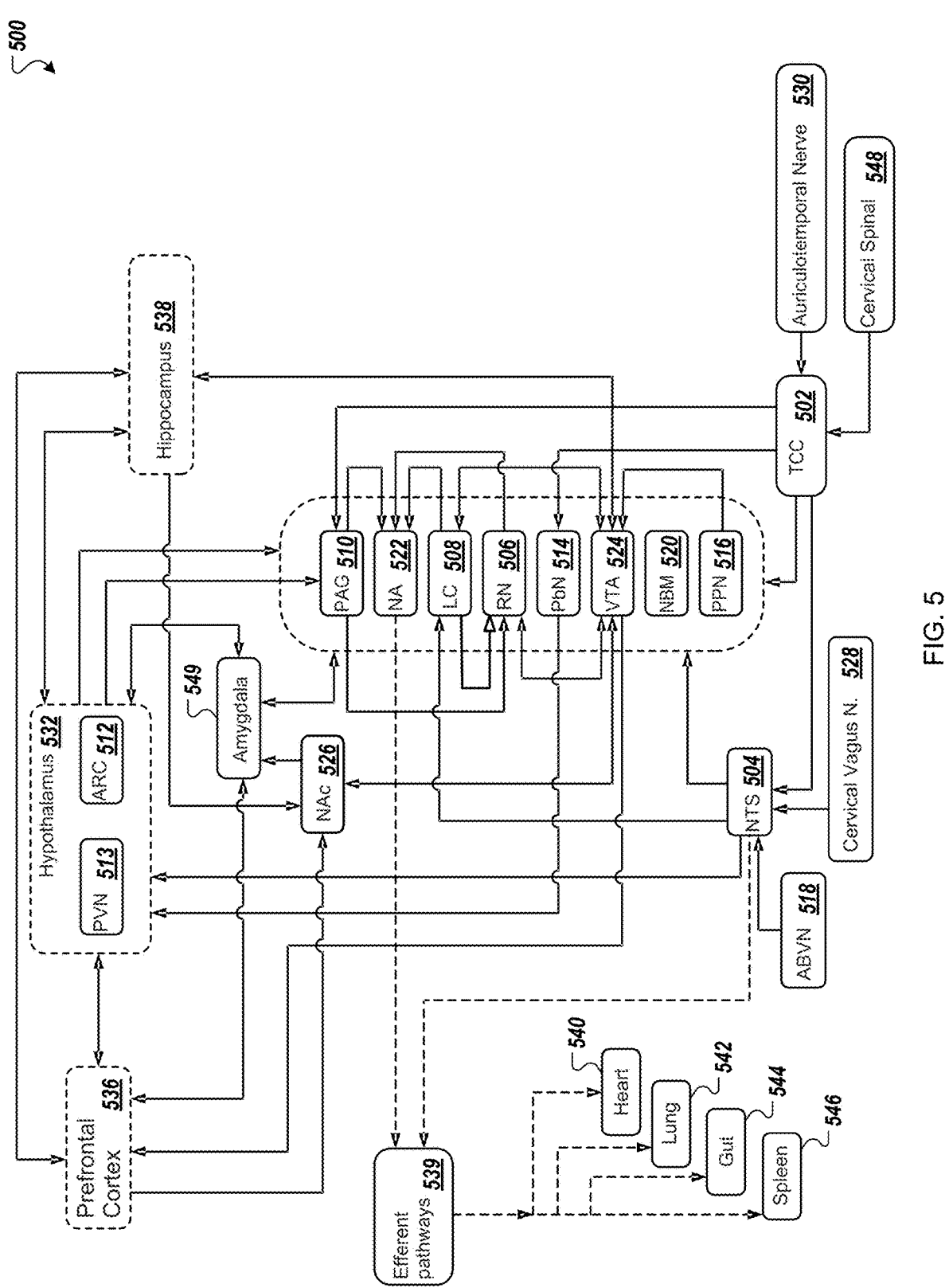
FIG. 5 is a block diagram mapping example neural structures and pathways.

In one aspect, the present disclosure relates to systems and methods for treating premenstrual syndrome (PMS). Selective serotonin reuptake inhibitors (SSRIs) are emerging as the most effective treatment option for PMS and PMDD. See, e.g., Steiner, Meir. "Premenstrual syndrome and premenstrual dysphoric disorder: guidelines for management." Journal of Psychiatry and Neuroscience 25.5 (2000): 459. Medications such as SSRIs increase serotonin (5-HT) availability by limiting its reabsorption (e.g., inhibiting its reuptake) at the synaptic cleft. An alternative to the pharmacological approach of increasing 5-HT local availability through limiting reabsorption is to release larger quantities of 5-HT. In the brain, 5-HT is mainly produced by neurons in the Raphe Nucleus (RN) 506 (see FIG. 5). There are several subdivisions or subnuclei in the RN; however, herein when we refer to the RN, we refer to any of the subnuclei. The RN 506 has afferent connections arising from the Nucleus Tractus Solitari (a.k.a. the nucleus of the solitary tract, solitary nucleus, or "NTS") 504 as well as from the hypothalamic arcuate nucleus (ARC) 512. Turning to FIG. 1A, a flow diagram of example activation paths 100 for increasing serotonin availability is illustrated. Activation of the NTS 504 as well as the ARC 512 leads to RN 506 activity and the release of 5-HT 102. Given the connections between the NTS 504 and both the trigeminal cervical complex (TCC) 502 and vagal afferents, one way to activate the NTS 504 as well as the ARC 512 is to increase vagal and/or TCC 502 activity. Increasing vagal activity by stimulating the auricular branch of the vagus nerve (ABVN) 518 has been shown to trigger NTS 504 activity; TCC 502 activity can be triggered by stimulating trigeminal branches, one of which is the auriculotemporal nerve (ATN) 530. That is, 5-HT availability 102, thus a treatment to ameliorate PMS symptoms, can be achieved by stimulating the vagus and/or the trigeminal fibers.

During the pre-menstrual luteal phase, most women experience increased sympathetic tone and a decreased parasympathetic tone; i.e., a decrease in the parasympathetic/sympathetic ratio (P/S ratio). These physiological changes tend to impact sleeping patterns, including reduced sleep efficiency and increased nocturnal awakenings. [Baker & Driver, 2007]. As a result, women tend to suffer sleep disturbances during the luteal phase. Modifying the P/S ratio, for example, is discussed below in relation to FIG. 6.

Low tolerance for noise and light as well as headaches and/or migraines during the pre-menstrual luteal phase share, to some degree, a common cause; that is the hypersensitization of the trigeminal network. This hypersensitization is at least partially due to the drastic increase in progesterone during this phase. Progesterone has been shown to increase neuronal excitability, and particularly that of the trigeminal network. This increase in trigeminal excitability is partially due to the increase in the production and release of calcitonin gene-related peptide (CGRP). Stimulation of trigeminal branches at high frequencies (e.g., between 70 Hz and 150 Hz) may be used to mitigate this condition.

Increased progesterone during the luteal phase also affects gut motility by slowing it down. This lower gut motility can lead to constipation, gas and bloating; sometimes known as PMS Belly. Vagus stimulation can be applied to increase gastric motility. See Steidel, Kenan, et al. "Transcutaneous auricular vagus nerve stimulation influences gastric motility: a randomized, double-blind trial in healthy individuals." Brain stimulation 14.5 (2021): 1126-1132.

Figure 19:
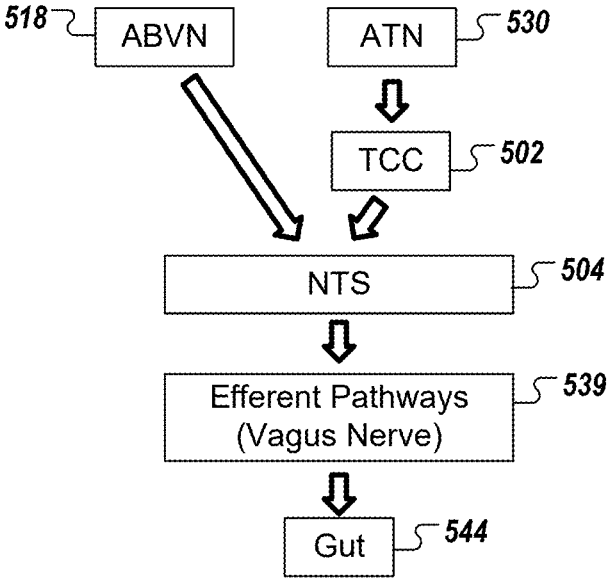
FIG. 19 is a block diagram of an example gut motility pathway.

Turning to FIG. 19, a flow diagram of an example gut motility pathway 1900 for increasing gut motility via neurostimulation is illustrated. Activation of the NTS 504 leads to activity in efferent pathways 539 (mainly the vagus nerve), resulting in stimulation of the gut 544. Given the connections between the NTS 504 and both the trigeminal cervical complex (TCC) 502, one way to activate the NTS 504 is to increase vagal and/or TCC 502 activity. Increasing vagal activity by stimulating the ABVN 518 has been shown to trigger NTS 504 activity; TCC 502 activity can be triggered by stimulating trigeminal branches, one of which is the auriculotemporal nerve (ATN) 530.

In some embodiments, PMS symptoms can be decreased by applying electrostimulation in a non-invasive manner with non-piercing electrodes to the skin located in close proximity to vagal and/or trigeminal neural fibers. PMS symptoms may similarly be decreased using a minimally invasive approach such as utilizing needles. An invasive approach, although less preferred, may also be used via implanted electrodes that, for example, wrap around the target nerves. In one example, vagal stimulation, using either a non-invasive approach or a minimally invasive approach, can be applied targeting the cervical vagus along the lateral neck. In another example, the vagal nerve may be activated through ABVN stimulation. The ABVN may be stimulated in or around the auricle, such as, in some examples, at the cymba concha, the tragus, and/or at the base of the temporal bone (e.g., at or in close proximity to the mastoid canaliculus (a.k.a. Arnold's canal)). Trigeminal fibers may be stimulated, in a non-invasive approach or in a minimally invasive approach, for example, by targeting the trigeminal ophthalmic branches. The trigeminal ophthalmic branches, in some non-limiting examples, may be targeted by positioning one or more electrodes at the forehead or below the eye, or by targeting the auriculotemporal nerve (ATN) (e.g., on the lateral aspect of the face, just in front of the ear, and/or on the upper portion of the auricle).

Food cravings, particularly for carbohydrates, are commonly reported in the pre-menstruation phase of the menstrual cycle. This phenomenon has been partially linked to decreased serotonin levels during this phase. Carbohydrate consumption increases tryptophan availability and subsequent serotonin synthesis in the brain, suggesting these cravings may represent a push from the body to consume carbohydrates in order to increase serotonin production. These cravings are further modulated by cyclic hormonal changes, particularly in estrogen levels, which affect both metabolic regulation and appetite control. Systems and methods described herein, in some embodiments, are configured to reduce these cravings through targeted neurostimulation of vagal and trigeminal pathways leading to activation of NTS, which in turn activates the raphe nucleus. The raphe nucleus is a primary site of serotonin production in the brain. This activation pathway promotes increased serotonin availability without requiring carbohydrate consumption. Additionally, the stimulation modulates hypothalamic activity, helping to regulate appetite control centers and stabilize the autonomic responses typically disrupted during menstruation. Through these mechanisms, the therapy can help reduce food cravings by addressing both the underlying serotonin deficiency and the autonomic dysregulation of appetite control systems.

Onset of PMS symptoms vary between individuals, in most cases appearing several days before menstruation. In some embodiments, PMS symptoms are treated by delivering stimulation to the ABVN and/or ATN using electrodes positioned in and/or around the ear. The stimulation treatment, for example, may be provided as needed upon or after the onset of symptoms. In an illustrative example, PMS may be treated by applying stimulation at least once every other day (e.g., every 12 hours, every 24 hours, every 36 hours, every 48 hours, etc.) for several days starting when symptoms begin to appear and ceasing stimulation sessions when symptoms are no longer perceived.

The central endorphin pathway's activation of the VTA not only leads to increased dopamine production but plays a crucial role in fatigue mitigation. Dopamine, a key neurotransmitter involved in motivation, arousal, and motor control, when released in higher quantities can reduce fatigue symptoms and increase physical performance capacity. Low dopamine levels have been associated with increased fatigue, decreased motivation, and reduced physical performance. See Dobryakova, E., et al. "The dopamine imbalance hypothesis of fatigue in multiple sclerosis and other neurological disorders." Frontiers in neurology 6 (2015): 52. Thus, activation of the central endorphin pathway can lead to increased dopamine availability via VTA activation, thereby providing a mechanism for fatigue reduction.

Figure 2:
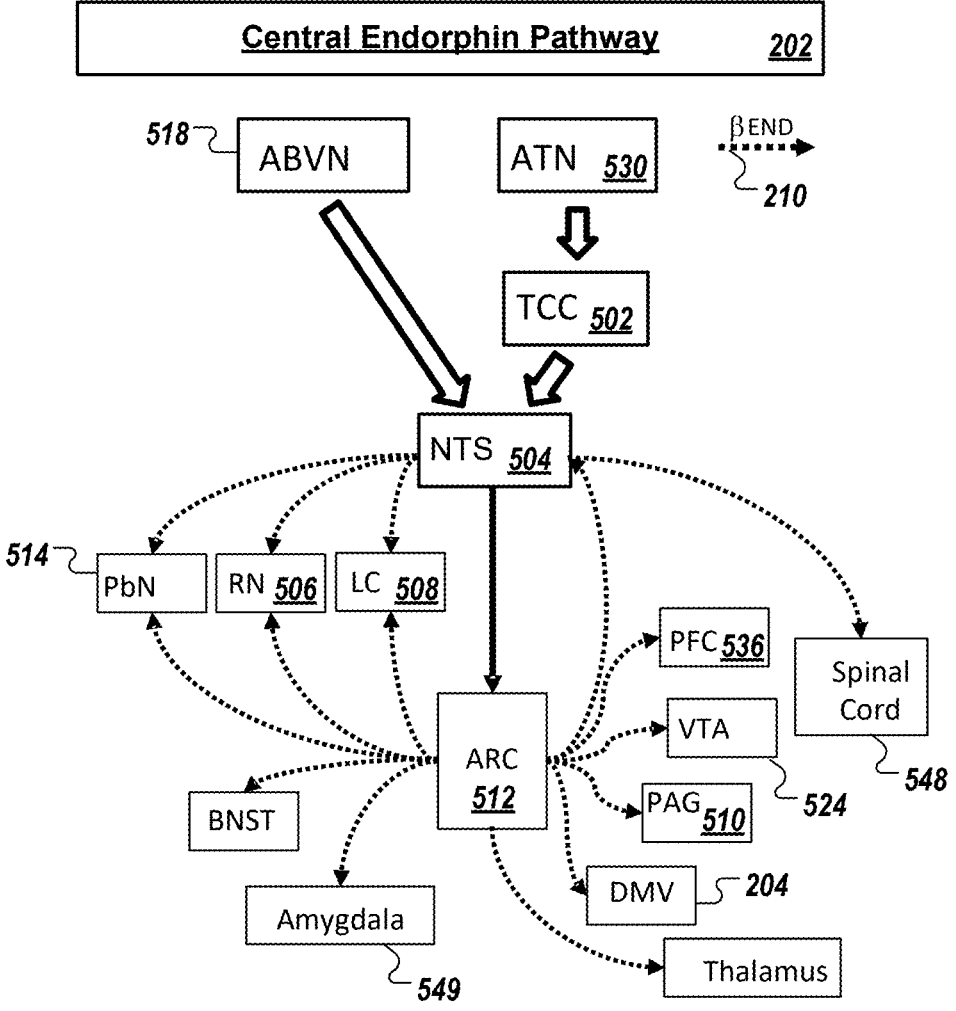
FIG. 2 is a block diagram of an example central endorphin pathway.

Beyond the negative impact PMS can have on the mood of the sufferer, PMDD can mimic serious emotional health conditions such as depression or an anxiety disorder. The effects on the patient suffering from PMDD often inhibit professional and/or social interactions for a week prior to the onset of menstruation and continuing into the first few days of the menstrual cycle. In some implementations, to counteract the stress and depression aspects of PMDD, neurostimulation therapy for treating PMDD can include triggering the central endorphin pathway to modulate stress and anxiety levels, combat symptoms of fatigue, and/or alleviate feelings of depression. The brain areas or nuclei forming the neural circuitry involved in the stress response are not only involved in depression but also are integral components of the Endogenous Opioid Circuit (EOC), which includes the Central Endorphin Pathway (FIG. 2) as well as the secondary connections arising from it. As illustrated in FIG. 2, the NTS 504, LC 508, PbN 514, PAG 510, RN 506, PFC 536, Ventral Tegmental Area (VTA) 524, and the Amygdala 549 are part of the EOC. The central endorphin pathway 202 interacts with several other brain regions or nuclei including with other hypothalamic areas. Stimulating afferent pathways to the central endorphin pathway 202 such as vagal and/or trigeminal structures activates this circuit and connected regions, including the VTA 524, which is one of the main producers of dopamine in the CNS. By activating the central endorphin pathway 202 and connected regions, PMDD symptoms related to stress, anxiety, fatigue, and depression may be mitigated.

Vasomotor Symptoms (VMS)

Figure 1B:
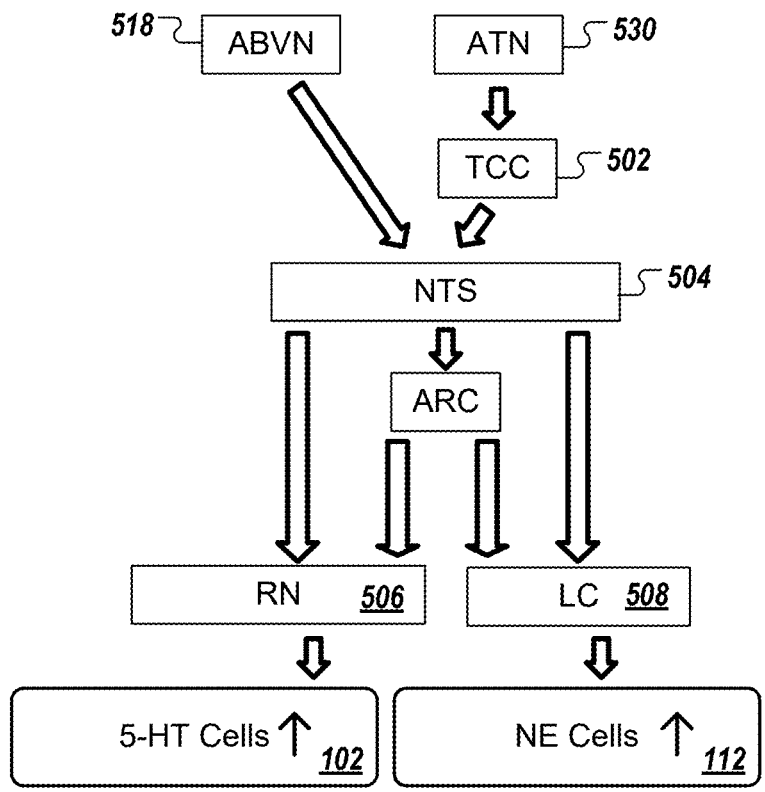
FIG. 1B is a block diagram of an example serotonin and norepinephrine availability enhancement pathway.

Abnormal hypothalamic thermoregulation is at the core of VMS. Bodily temperature is assessed and controlled by several interacting hypothalamic nuclei. Selective serotonin reuptake inhibitors (SSRIs) and norepinephrine reuptake inhibitors (SNRIs), respectively, increase the availability of 5-HT and norepinephrine (NE) by blocking the reuptake of these neurotransmitters in the synaptic clef. The availability of both 5-HT and NE can also be achieved by increasing their production. Turning to FIG. 1B, as illustrated in an example activation pathway for increasing serotonin and norepinephrine availability 110, the main NE and 5-HT production sites in the central nervous system (CNS) are respectively the Locus coeruleus (LC) 508 and the Raphe nucleus (RN) 506. Both nuclei receive connections from the NTS 504. Further, the RN 506 receives inputs from the LC 508. Activation of the LC 508 and RN 506, respectively, may result in an increase of NE 112 and 5-HT availability 102. NE is also produced by some NTS 504 neurons.

Figure 1C:
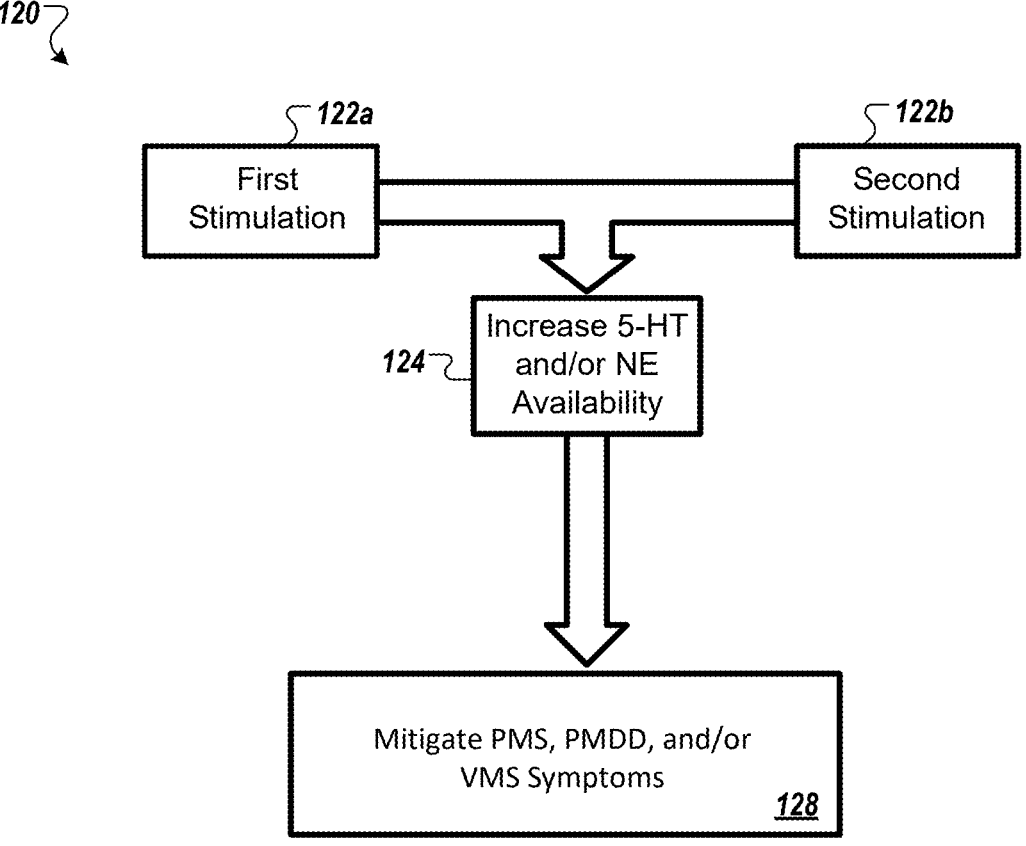
FIG. 1C is a block diagram of example stimulation paths for enhancing serotonin and/or norepinephrine availability.

Turning to FIG. 1C, in some embodiments, example stimulation paths 120 may be used to mimic the effect of currently used pharmacological treatments to help minimize VMS symptoms through providing neurostimulation therapy configured to increase 5-HT and/or NE 124. For example, as illustrated in the activation pathways 110 of FIG. 1B, activation of the NTS 504 can achieve an increase of both NE 112 and 5-HT 102. The NTS 504 activity can be promoted via a first stimulation 122a of vagal fibers and/or a second stimulation 122b of trigeminal fibers. The increase in 5-HT and/or NE availability 124 produced by the stimulation(s) 122a, 122b, for example, may mitigate the effects of VMS by promoting healthy thermoregulation 128.

In some embodiments, VMS therapy involves increasing 5-HT and/or NE by applying electrostimulation in a non-invasive manner with non-piercing electrodes to the skin located in close proximity to vagal and/or trigeminal neural fibers. Similarly, VMS therapy can be performed via a minimally invasive approach such as utilizing needles. An invasive approach, although less preferred, can also be used via implanted electrodes that, for example, wrap around the target nerves. In one example, the first stimulation 122a of FIG. 1C (e.g., vagal stimulation), using either a non-invasive approach or a minimally invasive approach, can be applied targeting the cervical vagus along the lateral neck. In another example, the vagal nerve may be activated through ABVN stimulation 122a. The ABVN may be stimulated in or around the auricle, such as, in some examples, at the cymba concha, the tragus, and/or at the base of the temporal bone (e.g., at or in close proximity to the mastoid canaliculus (a.k.a. Arnold's canal)). The second stimulation 122b of FIG. 1C may be applied to stimulate trigeminal fibers, in a non-invasive approach or in a minimally invasive approach, for example, by targeting the trigeminal ophthalmic branches. The trigeminal ophthalmic branches, in some non-limiting examples, may be targeted by positioning one or more electrodes at the forehead or below the eye, or by targeting the auriculotemporal nerve (ATN) (e.g., on the lateral aspect of the face, just in front of the ear, and/or on the upper portion of the auricle).

In some embodiments, VMS symptoms are diminished by delivering the first stimulation 122a to the ABVN and/or the second stimulation 122b to the ATN using electrodes positioned in and/or around the ear. The stimulation treatment, for example, may be provided at least once every other day and at least for five minutes per session to resolve or mitigate the condition. For example, the stimulation treatment may be provided once within each forty-eight-hour period, once within each twenty-four-hour period, once within each twelve-hour period, or otherwise as desired by the patient to mitigate discomfort. The length of the stimulation treatment, in some examples, may include at least five minutes, between five minutes and ten minutes, up to twenty minutes, up to thirty minutes, and/or as long as symptoms remain. In some cases in which the condition fails to become fully resolved, the therapy may be applied indefinitely to control the condition.

Dysmenorrhea

Dysmenorrhea, or pain due to menstrual cramps, can be divided into two aspects: the pain caused by a vasoconstriction produced by hyper contractility in the uterus (e.g., the initial trigger for the pain), and a potential central sensitization, which further increases the pain sensation. Thus, in some embodiments, a neurostimulation therapy designed to ease dysmenorrhea not only increases blood flow in the uterus but at the same time counteracts pain signaling at the central nervous system (CNS) level. An increase in parasympathetic activity at the uterus leads to vasodilation in this organ; thus, such an increase in parasympathetic activity can alleviate the above-mentioned ischemic scenario, thereby counteracting and diminishing cramping and pain. Endorphins can modulate pain signals in the CNS.

Figure 3A:
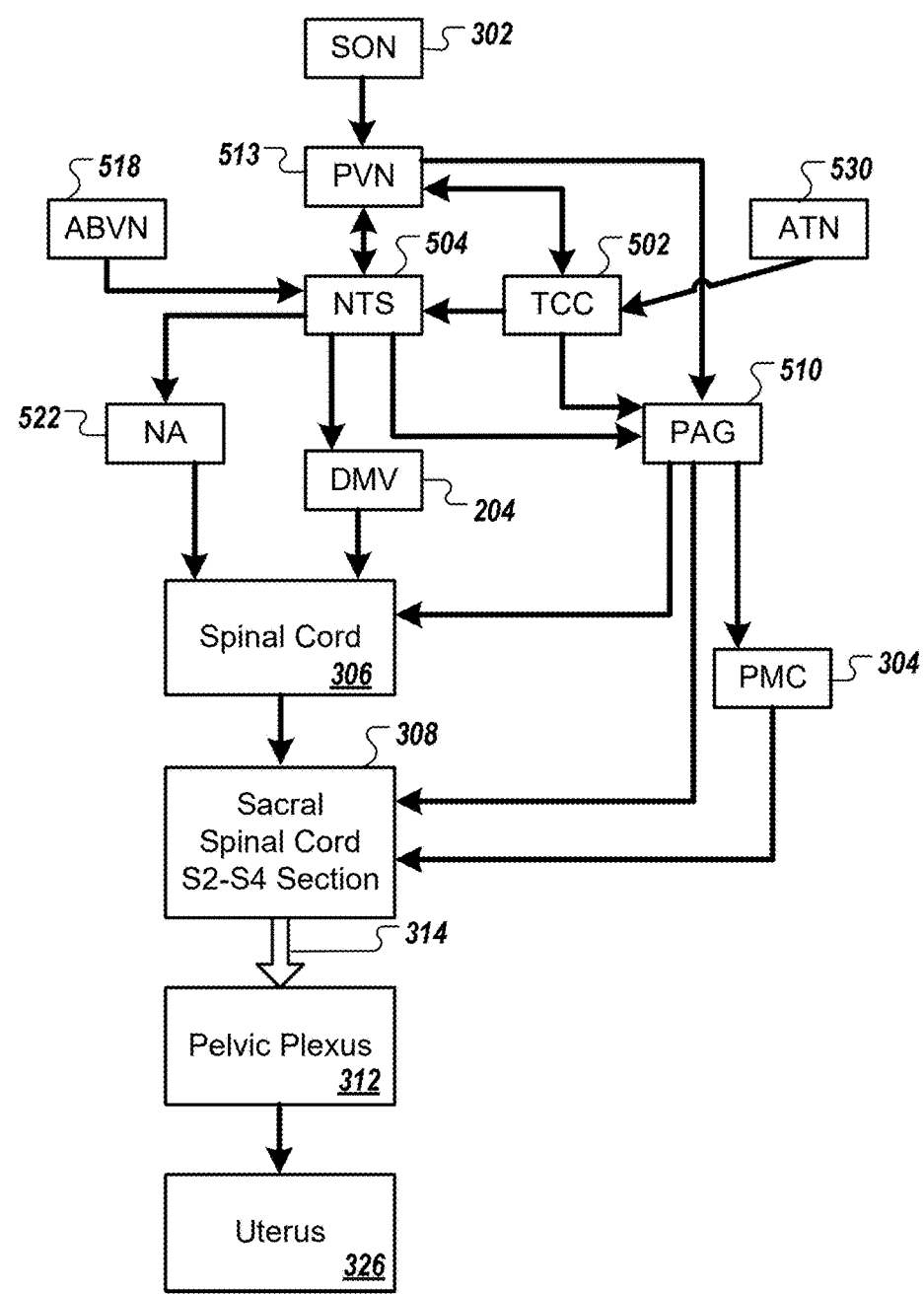
FIG. 3A is a block diagram of an example uterus parasympathetic pathway.

Turning to FIG. 3A, the parasympathetic innervation of the uterus involves a complex network of neural pathways originating from various regions of the central nervous system (CNS). This pathway begins in the hypothalamus, specifically in the paraventricular nucleus (PVN) 513 and supraoptic nucleus (SON) 302. These hypothalamic nuclei project to several brainstem structures, including the NTS 504, periaqueductal gray (PAG) 510, Pontine Micturition Center (PMC, also known as Barrington's nucleus) 304, dorsal motor nucleus of the vagus (DMV) 204, and nucleus ambiguus (NA) 522. The NTS 504 serves as an integrative center for autonomic function, receiving input from various sources and projecting to other autonomic control centers. The PAG 510 integrates information from higher centers and projects to both the PMC 304 and sacral spinal cord 308. The PMC 304 plays a vital role in coordinating micturition and has direct projections to sacral parasympathetic preganglionic neurons. The primary parasympathetic control of the uterus originates from the sacral spinal cord 308, specifically from the intermediolateral cell column (IML) in segments S2-S4. The cell bodies of preganglionic parasympathetic neurons located in the sacral IML give rise to axons that form the pelvic splanchnic nerves. These nerves carry preganglionic parasympathetic fibers to the pelvic ganglia (a.k.a. paracervical or Frankenhäuser's ganglia) which is in the pelvic plexus 312, where they synapse with postganglionic neurons. After synapsing in the pelvic ganglia, the post-ganglionic parasympathetic fibers, along with sympathetic and sensory fibers, form the uterovaginal plexus. The uterovaginal plexus 312 provides innervation to the uterus, cervix, and upper portion of the vagina. The postganglionic fibers then extend to the uterus 326 are generally referred to as uterovaginal branches. These branches synapse with the target tissue. The connections between these CNS structures and the sacral parasympathetic preganglionic neurons can be both monosynaptic and disynaptic. Monosynaptic connections exist from the PMC 304 and specific regions of the PAG 510 directly to sacral parasympathetic preganglionic neurons. Disynaptic connections include pathways from the hypothalamus (PVN 513, SON 302) and NTS 504 to sacral parasympathetic preganglionic neurons, likely relaying through the PAG 510 and/or PMC 304. The DMV 204 and NA 522, while primarily associated with parasympathetic control of thoracic and abdominal organs, also influence sacral parasympathetic activity. This influence occurs through several pathways: For example, there are bidirectional connections between the DMV 204 and NA 522 with the NTS 504, which in turn projects to the PAG 510 and PMC 304. There are also direct descending pathways to the spinal cord 306, including sacral regions 308, potentially involving relay stations in the reticular formation. In addition, the fact both DMV 204 and the NA 522 are part of the Central Autonomic Network (CAN) allows for activity in these two nuclei to exert modulatory effects on sacral parasympathetic activity through various polysynaptic pathways. The trigeminocervical complex (TCC) 502, formed by the caudal part of the trigeminal nucleus caudalis and the dorsal horns of the upper cervical spinal cord (C1-C3), also plays a significant role in modulating this parasympathetic outflow. The TCC 502 integrates nociceptive inputs from the face, head, and neck regions and has connections to several autonomic control centers, including direct projections to the NTS 504, allowing nociceptive information to influence autonomic regulation. The TCC 502 connections to the PAG 510 are important for pain modulation and autonomic responses. TCC 502 projections to hypothalamic nuclei, including the PVN 513, can modulate autonomic and neuroendocrine function. Furthermore, the TCC 502 provides indirect influence on the entire Central Autonomic Network (CAN) through its connections with the NTS 504, PAG 510, and hypothalamus. This intricate network of neural pathways allows for the integration of various sensory inputs, including nociceptive information from the head and neck regions, with autonomic control of pelvic organs, including the uterus 326.

There are several endorphinergic-producing brain regions. For example, turning to an example diagram of the central endorphin pathway 202 of FIG. 2, B-endorphins (BEND) 210 are produced by specialized neuronal populations which can be found in the ARC 512 as well as in the NTS 504. In fact, the ARC 512 is the largest producer of B-endorphins in the CNS. Activation of these brain regions or nuclei increases the release of B-endorphins 210, leading to brain interactions that diminish pain sensation. Activation of the NTS 504, for example, leads to ARC 512 activity. NTS 504 activation can be achieved via stimulation of vagal fibers (e.g., the ABVN 518) as well as trigeminal branches (e.g., the ATN 530). Applying electrostimulation in either a non-invasive manner or a minimally invasive manner to the skin located in close proximity to vagal and/or trigeminal neural fibers results in NTS 504 activity, which in turn can limit the pain sensation generated by menstrual cramps. An invasive approach, although less preferred, can also be used via implanted electrodes that, for example, wrap around the target nerves.

The uterus 326, as other pelvic organs, is enervated amongst other by the pelvic splanchnic nerves 314 (a.k.a. nervi erigentes). The pelvic splanchnic nerves 314 originate from the S2-S4 spinal branches and carry parasympathetic efferent fibers as well as visceral afferent ones. The parasympathetic outflow reaching these nerves has been traced up all the way to the hypothalamus, in some cases into the periaqueductal gray area (PAG) 510. Amongst other, the PAG 510 receives fibers from the TCC 502 and the NTS 504. The PAG 510 sends efferent fibers, amongst others, to the NTS 504, the dorsal motor nucleus of the vagus nerve (DMV) 204, and to the nucleus ambiguus (NA) 522.

There are both left and right pelvic splanchnic nerves as well as left and right ganglion and plexus. In the present document, we are not distinguishing between left and right activity, it should be understood that any reference to a certain nerve, ganglion, or plexus encompasses reference to both right and left when they exist.

In some embodiments, neurostimulation therapy for treatment of dysmenorrhea involves activating the uterus parasympathetic pathway 300. As described above, this pathway involves multiple areas including cortical, hypothalamic, and brainstem areas as well as sacral spinal cord regions 308 leading to an increase in parasympathetic outflow via the pelvic splanchnic nerve 314. Modulation of NTS 504 and TCC 502 activity results in a modulatory effect of the neural network described above. Activity in NTS 504 and TCC 502 can be achieved by stimulating respectively the ABVN 518 and the ATN 530 (as described above, TCC 502 activity influences NTS 504 activity). Thus, stimulation either of the ABVN 518 or the ATN 530 leads to an enhance parasympathetic response in the uterus 326. Furthermore, stimulation of both the ABVN 518 and the ATN 530 can provide a synergetic effect; thus, producing a stronger response.

Figure 7:
FIG. 7 is a block diagram of an example uterus vasodilation intervention pathway.

Furthermore, turning a uterus vasodilation intervention pathway 700 of FIG. 7, stimulation of the ABVN 518 and/or the ATN 530, in addition to increasing parasympathetic activity, leads to an increase in acetylcholine (ACh) release 702; in turn, and increase in ACh release 702 has a vasodilation effect that can contract an existing vasoconstriction scenario in the uterus 326 such as in the case of dysmenorrhea.

In accordance with the pathway 300 of FIG. 3A and/or the pathway 700 of FIG. 7, in some embodiments, NTS 504 activity for treatment of dysmenorrhea can be triggered via vagal stimulation, using either a non-invasive approach or a minimally invasive approach. Neurostimulation can be applied, in one example, targeting the cervical vagus along the lateral neck. In another example, the vagal nerve may be activated through ABVN 518 stimulation. The ABVN 518 may be stimulated in or around the auricle, such as, in some examples, at the cymba concha, the tragus, and/or at the base of the temporal bone (e.g., at or in close proximity to the mastoid canaliculus (a.k.a. Arnold's canal)). Trigeminal fibers may be stimulated, in a non-invasive approach or in a minimally invasive approach, for example, by targeting the trigeminal ophthalmic branches. The trigeminal ophthalmic branches, in some non-limiting examples, may be targeted positioning one or more electrodes at the forehead or below the eye, or by targeting the auriculotemporal nerve (ATN) 530 (e.g., on the lateral aspect of the face, just in front of the ear, and/or on the upper portion of the auricle). In addition to NTS 504 activity, activation of vagal and/or trigeminal central targets results in an overall increase in parasympathetic activity, including higher vagal descending activity. This vagal descending activity reaches the uterus resulting in the above-mentioned vasodilation in uterine vasculature, thereby easing vasoconstriction and increasing blood flow in the organ and leading to diminishing ischemic pain.

In some embodiments, dysmenorrhea symptoms are treated by delivering stimulation to the ABVN 518 and/or ATN 530 using electrodes positioned in and/or around the ear. The stimulation treatment, for example, may be provided at least once every other day and at least for five minutes per session to resolve or mitigate the condition. For example, the stimulation treatment may be provided once within each forty-eight-hour period, once within each twenty-four-hour period, once within each twelve-hour period, or otherwise as desired by the patient to manage discomfort. The length of the stimulation treatment, in some examples, may include at least five minutes, between five minutes and ten minutes, up to twenty minutes, up to thirty minutes during menses such that pelvic pain is diminished to at least to a manageable level. In some cases, some women may require constant therapy or repeated applications of at least five minutes so pelvic pain is diminished to at least to a manageable level.

In some embodiments, dysmenorrhea symptoms are managed through adjusting parasympathetic and/or sympathetic activity, thereby altering the parasympathetic/sympathetic (P/S) ratio. The autonomic nervous system is regulated by a complex network of neural structures spanning cortical, subcortical, and brainstem regions. At the cortical level, key areas include the insular cortex, anterior cingulate cortex, prefrontal cortex, and amygdala. These regions integrate emotional, cognitive, and visceral information, exerting top-down control over autonomic function. The insular cortex, in particular, plays a crucial role in modulating cardiovascular responses and influencing both sympathetic and parasympathetic activity.

Subcortically, the hypothalamus serves as a primary integration center for autonomic control. Key hypothalamic nuclei include the paraventricular nucleus (PVN) 513, dorsomedial nucleus (DMH), and lateral hypothalamic area (LHA). The PVN 513 integrates various inputs and coordinates autonomic responses, generally increasing sympathetic outflow when activated. The DMH is involved in stress responses and cardiovascular regulation, primarily enhancing sympathetic activity, while the LHA influences feeding behavior and arousal, typically increasing parasympathetic tone.

In the brainstem, several nuclei play critical roles in autonomic regulation. The rostral ventrolateral medulla (RVLM) serves as the primary source of excitatory drive to sympathetic preganglionic neurons, while the caudal ventrolateral medulla (CVLM) provides inhibitory input to the RVLM, thus modulating sympathetic activity. The nucleus tractus solitarius (NTS) 504 receives and integrates visceral afferent information, influencing both sympathetic and parasympathetic activity.

Figure 6:
FIG. 6 is a block diagram of an example P/S ratio enhancing pathway.

Turning to FIG. 6, an example parasympathetic to sympathetic activity ratio stimulation pathway 600 is illustrated. Parasympathetic outflow is primarily mediated by the nucleus ambiguus (NA) 522 and the dorsal motor nucleus of the vagus (DMV) 204. The NA 522 is the major source of parasympathetic control to the heart, while the DMV 204 provides parasympathetic innervation to subdiaphragmatic organs.

The LC's role in producing and delivering NE throughout the brain is particularly important in managing fatigue states. The LC-noradrenergic system is fundamental in maintaining alertness and combating fatigue through its effects on arousal and attention networks in the brain. LC activity is closely linked to arousal and wakefulness states, with decreased LC activity being associated with increased fatigue. See Sara, S. J., and Bouret, S. "Orienting and reorienting: the locus coeruleus mediates cognition through arousal." Neuron 76.1 (2012): 130-141. Importantly, the NTS has direct projections to the LC, and activation of the NTS via vagal and/or trigeminal stimulation can trigger LC activity. Therefore, therapeutic activation of the NTS can lead to increased LC activity and consequently to increased NE availability, providing an additional mechanism for fatigue reduction. This NTS-LC pathway activation can be achieved via stimulation of vagal and/or trigeminal branches, as these neural networks have strong projections to the NTS.

The periaqueductal gray (PAG) 510 is another crucial structure in autonomic regulation, involved in pain modulation, autonomic control, and defensive behaviors. Different columns of the PAG 510 mediate distinct autonomic responses, influencing both sympathetic and parasympathetic activity. The trigeminocervical complex (TCC) 502, while primarily associated with headache pathophysiology, can also influence autonomic responses, particularly in the craniofacial region.

Two important modulatory systems, the locus coeruleus (LC) 508 and the raphe nuclei (RN) 506, exert widespread influences on autonomic function. The LC 508, a major source of noradrenergic projections throughout the brain, influences arousal, attention, and stress responses, generally enhancing sympathetic activity. The raphe nuclei 506, through their serotonergic projections, modulate various autonomic functions including thermoregulation, cardiovascular control, and respiratory function, influencing both sympathetic and parasympathetic activity.

At the spinal level, sympathetic outflow is mediated by the intermediolateral cell column (IML) from T1 to L2, while parasympathetic outflow to pelvic organs originates from the sacral parasympathetic nucleus (S2-S4).

From top-to-bottom, the neural pathways providing a modulatory effect on sympathetic activity begin at cortical areas to the hypothalamus (e.g., PVN 513) to brainstem areas such as the rostral ventrolateral medulla (RVLM) 604 from which connections go to the spine 602*b* and from there to the sympathetic chain ganglia, from which it reaches its target organs. As for the neural parasympathetic pathways, similar to the sympathetic ones, connections from cortical regions reach to the hypothalamus (e.g., PVN) 513, then brainstem areas, such as the NTS 504, DMV 204, NA 522 (NTS 504 projects to DMV 204 and NA 522) and the cranial parasympathetic nerves followed by the parasympathetic sacral nerves. In the case of the parasympathetic system, the projection to the target organs is accomplished by the preganglionic neuronal projections exiting the spine 602*a,b* (i.e., parasympathetic cranial and parasympathetic sacral nerves) which in turn synapse at different ganglion that are close to the target organ. From those parasympathetic ganglia, postganglionic neurons arise and reach the target organ. The parasympathetic cranial nerves include cranial nerves III, VII, IX, and X; respectively oculomotor, facial, glosso-pharyngeal, and vagus nerves. The parasympathetic sacral nerves include the sacral spinal nerves S2-S4 as well as the pelvic splanchnic nerves.

It is interesting to note that with the exception of the vagus nerve, many, if not most, other cranial parasympathetic nerves and post ganglionic fibers are carried out via a trigeminal nerve branch.

Autonomic balance is achieved through the intricate interplay of these neural structures. During stress responses, increased activity in the amygdala, LC 508, and PAG 510 leads to enhanced sympathetic outflow via the hypothalamus 513 and RVLM 604. Conversely, during rest and digestion, increased activity in the NA 522 and DMV 204 promotes parasympathetic dominance.

The PAG 510, with its distinct columns, can elicit various autonomic patterns associated with different behavioral responses, such as fight-or-flight or freezing behaviors. The raphe nuclei 506, through their serotonergic projections, can modulate these responses and influence autonomic balance in a context-dependent manner.

The balance between parasympathetic and sympathetic activity, which is sometimes used/provided as an activity ratio; in other words, the parasympathetic/sympathetic ratio (P/S) is continuously adjusted based on internal and external stimuli, maintaining homeostasis and allowing appropriate responses to environmental challenges. This balance is achieved through the intricate interactions between all the aforementioned neural structures, with each playing a specific role in modulating autonomic function. For example, the prefrontal cortex exerts inhibitory control over autonomic responses, helping to balance sympathetic and parasympathetic activity. The anterior cingulate cortex is involved in autonomic arousal and stress responses, primarily enhancing sympathetic activity. The amygdala, particularly important in emotional processing, can enhance sympathetic activity during emotional and stress responses.

Additional neural structures involved in maintaining homeostasis and allowing appropriate responses to environmental challenges include the A5 Noradrenergic Cell Group (A5) 608, which is located in the pons and involved in sympathetic regulation of cardiovascular and respiratory functions.

In the brainstem, the NTS 504 serves as an integration center for visceral afferent information, influencing both sympathetic and parasympathetic activity based on input from various sensory systems. The RVLM 604 and caudal ventrolateral medulla (CVLM) 606 play crucial roles in moment-to-moment blood pressure regulation, with the RVLM 604 providing excitatory drive to sympathetic neurons and the CVLM 606 modulating this activity through inhibitory inputs.

The LC 508, through its widespread production and delivery of NE, (a.k.a., noradrenergic projections), can rapidly influence autonomic function across multiple brain regions, generally promoting arousal and sympathetic activation. The raphe nuclei, with their serotonergic projections, provide a more modulatory influence, affecting various autonomic functions including thermoregulation and cardiovascular control.

As is evident from the illustration of FIG. 6, these systems do not operate in isolation but rather form a highly interconnected network. For instance, the PAG 510 has connections with the hypothalamus 513, amygdala, and brainstem autonomic centers, allowing it to coordinate complex behavioral and autonomic responses. Similarly, the TCC, while primarily involved in headache pathophysiology, has connections with the PAG 510 and other autonomic centers, thus influencing autonomic responses.

Autonomic balance is maintained through a sophisticated interplay of cortical, subcortical, and brainstem structures, each contributing to the fine-tuning of sympathetic and parasympathetic activity.

Thus, the P/S ratio can be increased by applying electrostimulation in a non-invasive manner with non-piercing electrodes to the skin located in close proximity to vagal and/or trigeminal neural fibers. The same is true using a minimally invasive approach such as utilizing needles. An invasive approach, although less preferred, can also be used via implanted electrodes that, for example, wrap around the target nerves. Neurostimulation can be applied, in one example, targeting the cervical vagus along the lateral neck. In another example, the vagal nerve may be activated through ABVN stimulation. The ABVN may be stimulated in or around the auricle, such as, in some examples, at the cymba concha, the tragus, and/or at the base of the temporal bone (e.g., at or in close proximity to the mastoid canaliculus (a.k.a. Arnold's canal)). Trigeminal fibers may be stimulated, in a non-invasive approach or in a minimally invasive approach, for example, by targeting the trigeminal ophthalmic branches. The trigeminal ophthalmic branches, in some non-limiting examples, may be targeted by positioning one or more electrodes at the forehead or below the eye, or by targeting the auriculotemporal nerve (ATN) (e.g., on the lateral aspect of the face, just in front of the ear, and/or on the upper portion of the auricle).

Figure 3B:
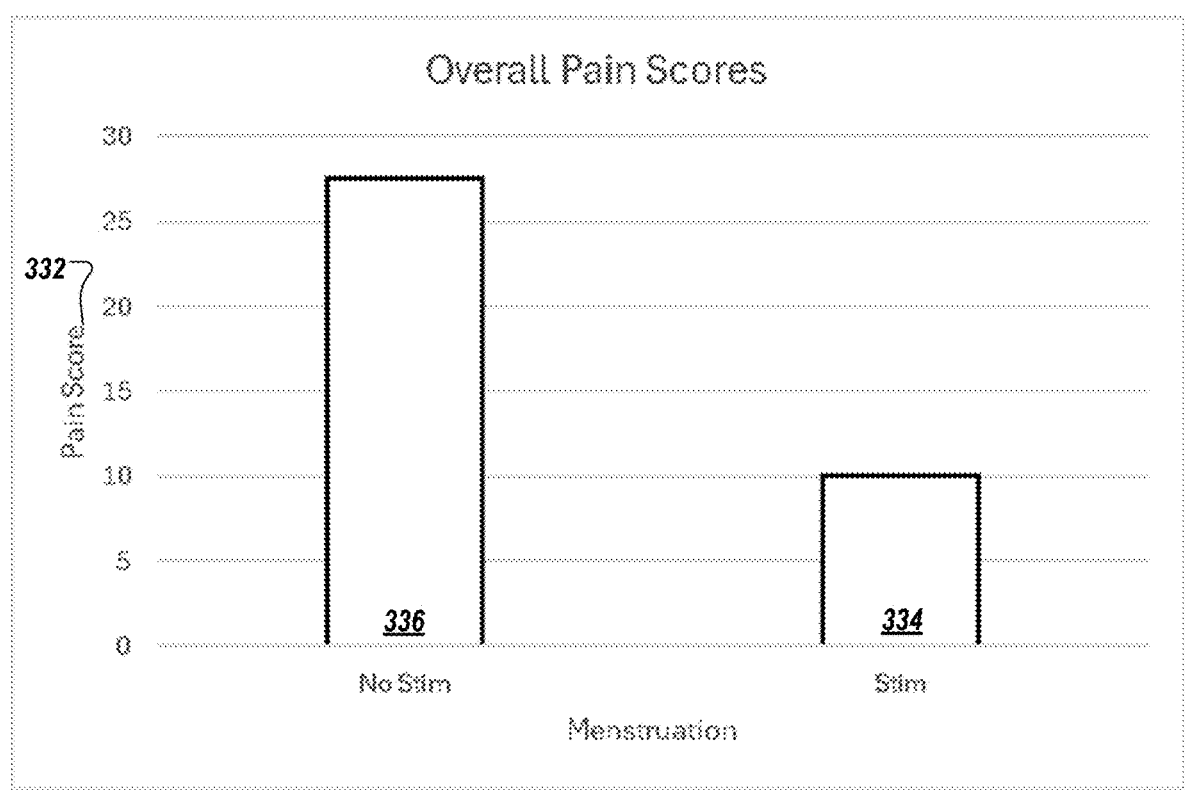
FIG. 3B is a graph demonstrating example outcomes related to applying stimulation via the pathway of FIG. 3A.

Turning to FIG. 3B, a graph demonstrates example outcomes 330 related to applying neurostimulation as discussed above to manage pain due to dysmenorrhea. A group of women were treated with auricular neurostimulation during menstruation, two stimulation sessions per day (e.g., one toward the beginning of the day and the other toward the end of the day) with each stimulation session lasting about an hour. Each woman was provided a standard survey form that is used to derive a pain score 332. Assessments were performed twice for each woman; one menstrual cycle without stimulation and one menstrual cycle with stimulation being applied. As illustrated, there was an average pain reduction of approximately 63% when stimulation was applied 334 vs. when no stimulation was delivered 336 (from 27 to 10, i.e., a 17-point reduction out of 27). Thus, the pain level of the test group of women 334 who received neurostimulation therapy was less than half that, on average, than the control group of women 336 experienced.

Preeclampsia

Evidence suggests preeclampsia is caused by vasoconstriction in uteroplacental tissue subsequently causing placental ischemia followed by the release of hypertensive substances into the maternal circulation, including pro-inflammatory factors. The above is accompanied by an increased sympathetic activity and thus a decrease in parasympathetic/sympathetic ("P/S") ratio.

Activation of neural centers leading to spleen activity has been shown to produce an anti-inflammatory response including a decrease of pro-inflammatory factors as well as an increase in anti-inflammatory factors. Turning to FIG. 4, activation of vagal fibers directly or indirectly (e.g., the vagus nerve 556), for example via activation of the NTS 504, results in activating celiac ganglion 422, leading to spleen 546 activation, and thereby triggering the anti-inflammatory response. In particular, the anti-inflammatory pathway 400 may be activated by stimulating the ABVN 518 and/or the ATN 530 which, as stated before, have projections to the NTS 504. These projections elicit cholinergic anti-inflammatory effects via efferent pathways, mostly via the vagus nerve 556. Systemic anti-inflammatory effects occur when the vagus nerve 556 mediates spleen 546 function, thereby reducing the amount of pro-inflammatory cytokines 402 available in circulating blood 404. In addition, a local anti-inflammatory effect occurs at organs reached by the efferent pathways, such as at the uterus 326.

Additionally, activation of the NTS 504 as well as other centers can lead to an increase in parasympathetic tone which, in turn, results in an increase of P/S ratio. An increase in P/S ratio and/or an increase in anti-inflammatory activity can result in an anti-preeclampsia response. See the description of FIG. 6, above, for additional details regarding adjusting the P/S ratio. Therefore, activation of the NTS 504 can be used as a novel preeclampsia treatment. As mentioned earlier, NTS 405 activity can be driven by stimulation of the vagal and/or the trigeminal neural networks, for example via stimulating the ABVN 518 and/or the ATN 530.

Thus, the P/S ratio can be increased by applying electro-stimulation in a non-invasive manner with non-piercing electrodes to the skin located in close proximity to vagal and/or trigeminal neural fibers. The same is true using a minimally invasive approach such as utilizing needles. An invasive approach, although less preferred, can also be used via implanted electrodes that, for example, wrap around the target nerves. Neurostimulation can be applied, in one example, targeting the cervical vagus along the lateral neck. In another example, the vagal nerve may be activated through ABVN stimulation. The ABVN may be stimulated in or around the auricle, such as, in some examples, at the cymba concha, the tragus, and/or at the base of the temporal bone (e.g., at or in close proximity to the mastoid canaliculus (a.k.a. Arnold's canal)). Trigeminal fibers may be stimulated, in a non-invasive approach or in a minimally invasive approach, for example, by targeting the trigeminal ophthalmic branches. The trigeminal ophthalmic branches, in some non-limiting examples, may be targeted by positioning one or more electrodes at the forehead or below the eye, or by targeting the auriculotemporal nerve (ATN) (e.g., on the lateral aspect of the face, just in front of the ear, and/or on the upper portion of the auricle).

In some embodiments, preeclampsia symptoms are treated by delivering stimulation to the ABVN and/or ATN using electrodes positioned in and/or around the ear. Stimulation may be applied, for example, at least one time per forty-eight-hour period and for at least five minutes per session. For example, the stimulation treatment may be provided once within each forty-eight-hour period, once within each twenty-four-hour period, once within each twelve-hour period, etc. The length of the stimulation treatment, in some examples, may include at least five minutes, between five minutes and ten minutes, up to twenty minutes, up to thirty minutes, or longer. Sessions may be continued while the condition is present or while the probability of suffering from preeclampsia is present as determined by a health care professional (HCP).

In some implementations, prior to each treatment session, a systolic blood pressure or a diastolic blood pressure is measured to confirm treatment is appropriate. For example, each session may be conducted after confirming that the subject's systolic and/or diastolic blood pressure is above a clinically significant level. The clinically significant level, for example, may be set by a health care professional. In illustration, the clinically significant level may be a diastolic blood pressure level of at least 90 mm Hg and/or a systolic blood pressure level of at least 140 mm Hg. In another example, one or more sessions may be conducted during a period of time when the subject's blood pressure is under control and at a clinically acceptable level (e.g., when systolic blood pressure (SBP) is below 140 mmHg). In this manner, for example, a healthy blood pressure may be maintained by applying some treatments after the subject's blood pressure has dropped within a desirable range (e.g., at or below the clinically significant level). In certain embodiments, a base therapeutic schedule may be applied to a subject diagnosed with preeclampsia, with additional sessions prompted/provided based on blood pressure elevation. In illustration, an individual's blood pressure may be monitored periodically (e.g., every five minutes, every ten minutes, every twenty minutes, etc.), such as by a wearable health tracking device, and an additional therapeutic session may be suggested and/or triggered upon a rise in blood pressure above a threshold level (e.g., the clinically significant level or an additional amount above the clinically significant level). The predetermined treatment schedule, for example, may be defined by a health professional. To determine blood pressure levels and/or stability of blood pressure level, in some embodiments, the systolic and/or diastolic blood pressure levels of the individual may be measured on at least two occasions at least four hours apart.

To monitor the subject's responsiveness to treatment, in some embodiments, a urine protein may be periodically measured. A urine protein/creatinine ratio of 0.3 or greater and/or at least 300 mg of protein in a 24-hour urine sample, in some examples, may be indicative of ongoing preeclampsia. In illustration, two urine measurements taken six hours apart may be used to monitor ongoing symptoms of preeclampsia.

Postural Orthostatic Tachycardia Syndrome (POTS)

The pathophysiology of POTS is not yet well understood, however, it is clear that in most POTS cases there is an autonomic imbalance in which the parasympathetic/sympathetic activity ratio (P/S) is diminished. This can be due to sympathetic hyperactivity and/or parasympathetic hypoactivity. The P/S ratio may be increased by increasing parasympathetic tone, which can be achieved via brainstem activity, in particular at the NTS, as discussed above in relation to FIG. 6. As mentioned earlier, NTS activity can be driven by stimulation of the vagal and/or the trigeminal neural network.

In some embodiments, methods and systems for treating POTS include increasing the P/S ratio by applying electro-stimulation in a non-invasive manner with non-piercing electrodes to the skin located in close proximity to vagal and/or trigeminal neural fibers. The vagal and/or trigeminal neural fibers may be stimulated, in other embodiments, using a minimally invasive approach such as utilizing needles. An invasive approach, although less preferred, can also be used via implanted electrodes that, for example, wrap around the target nerves. Neurostimulation can be applied, in one example, targeting the cervical vagus along the lateral neck. In another example, the vagal nerve may be activated through ABVN stimulation. The ABVN may be stimulated in or around the auricle, such as, in some examples, at the cymba concha, the tragus, and/or at the base of the temporal bone (e.g., at or in close proximity to the mastoid canaliculus (a.k.a. Arnold's canal)). Trigeminal fibers may be stimulated, in a non-invasive approach or in a minimally invasive approach, for example, by targeting the trigeminal ophthalmic branches. The trigeminal ophthalmic branches, in some non-limiting examples, may be targeted by positioning one or more electrodes at the forehead or below the eye, or by targeting the auriculotemporal nerve (ATN) (e.g., on the lateral aspect of the face, just in front of the ear, and/or on the upper portion of the auricle).

In some embodiments, POTS symptoms are treated by providing ABVN and/or ATN stimulation in and/or around the ear. Auricular neurostimulation therapy may be provided, in an example, at least one time per day and at least for seven minutes per session such that symptoms diminish to a manageable level in everyday activities. For example, the stimulation treatment may be provided once within each twenty-four-hour period, once within each twelve-hour period, or more frequently in at least an initial phase of treatment. The length of the stimulation treatment, in some examples, may include at least seven minutes, between seven minutes and ten minutes, up to twenty minutes, up to thirty minutes, and/or longer. As POTS is a chronic condition, after a period of daily therapy application at a first session length, therapy can be then applied on a less frequent basis and/or for a shorter duration per session, for example every other day or every third day provided that symptoms remain under control or at a manageable level. Therapy application can continue to become less frequent and/or of shorter duration as symptoms subside or are no longer present. However, neurostimulation application frequency and/or session length can be increased if one or more symptoms return and/or become more prevalent.

Polycystic Ovary Syndrome (PCOS)

The root cause of PCOS is not yet fully understood; however, it is clear that women suffering from PCOS present an automimic imbalance (a.k.a. dysautonomia) in which the sympathetic and parasympathetic systems are respectively hyper- and hypoactive affecting the hypothalamic pituitary ovarian axis. Currently, there is no treatment to remedy PCOS. As such, healthcare professionals try to control the symptoms using multiple treatments. Reestablishing autonomic balance can be used as a new treatment option for PCOS, as increasing the P/S ratio can improve PCOS symptoms. Modifying the P/S ratio, for example, is discussed above in relation to FIG. 6. As in the POTS case described above, the P/S ratio can be increased by increasing parasympathetic tone, which can be achieved via brainstem activity in particular at the NTS. As mentioned earlier, NTS activity can be driven by stimulation of the vagal and/or the trigeminal neural network.

In one aspect, systems and methods for treating PCOS involve increasing the P/S ratio by applying electrostimulation in a non-invasive manner with non-piercing electrodes to the skin located in close proximity to vagal and/or trigeminal neural fibers. The P/S ratio may be similarly increased using a minimally invasive approach such as utilizing needles. An invasive approach, although less preferred, can also be used via implanted electrodes that, for example, wrap around the target nerves. Neurostimulation can be applied, in one example, targeting the cervical vagus along the lateral neck. In another example, the vagal nerve may be activated through ABVN stimulation. The ABVN may be stimulated in or around the auricle, such as, in some examples, at the cymba concha, the tragus, and/or at the base of the temporal bone (e.g., at or in close proximity to the mastoid canaliculus (a.k.a. Arnold's canal)). Trigeminal fibers may be stimulated, in a non-invasive approach or in a minimally invasive approach, for example, by targeting the trigeminal ophthalmic branches. The trigeminal ophthalmic branches, in some non-limiting examples, may be targeted by positioning one or more electrodes at the forehead or below the eye, or by targeting the auriculotemporal nerve (ATN) (e.g., on the lateral aspect of the face, just in front of the ear, and/or on the upper portion of the auricle).

In some embodiments, treatments for reducing or minimizing PCOS involve providing ABVN and/or ATN stimulation in and/or around the ear. Auricular neurostimulation therapy may be provided, in an example, at least once every other day and at least for five minutes per session such until the condition is mitigated if not resolved. For example, the stimulation treatment may be provided once within each forty-eight-hour period, once within each twenty-four-hour period, once within each twelve-hour period, etc. The length of the stimulation treatment, in some examples, may include at least five minutes, between five minutes and ten minutes, up to twenty minutes, up to thirty minutes, and/or as long as symptoms remain. In some cases in which the condition fails to become fully resolved, the therapy may be applied indefinitely to control the condition. The session duration and/or frequency of treatment may be adjusted as needed to mitigate symptoms.

Endometriosis and Adenomyosis

Several recent studies have shed light regarding the nature of endometrial lesions; these studies point to evidence suggesting that endometrial lesions are wounds undergoing repeated tissue injury and repair along with menstrual cyclic bleeding. As such these lesions can be considered dynamic lesions, i.e., they are not set as one can say they are constantly changing as they repair and reoccur. Under these conditions, changes that can positively affect the constant lesion-regeneration cycle can prove beneficial as it would not only allow the lesions to diminish but it could also get to a point in which no more lesions are generated.

A recent study showed that, compared to regular human epithelial cells, endometriotic epithelial cells had a lower count of the α7 nicotinic acetylcholine receptors (α7nAChR), furthermore, α7nAChR agonist significantly diminished the proliferation of endometriotic lesions in a preclinical setting. See Hao, Meihua, Xishi Liu, and Sun-Wei Guo. "Activation of α7 nicotinic acetylcholine receptor retards the development of endometriosis." Reproductive Biology and Endocrinology 20.1 (2022): 85.

In one aspect, a neurostimulation therapy for endometriosis involves activation of parasympathetic centers to increase acetylcholine (ACh), which is the natural agonist of the α7nAChR, thereby diminishing the proliferation of endometriotic lesions and combatting the lesion producing cycle of endometriosis. Turning to FIG. 3A, the uterus 326, as other pelvic organs, is enervated amongst other by the pelvic splanchnic nerves (a.k.a. nervi erigentes). The pelvic splanchnic nerves originate from the S2-S4 spinal branches 308 and carry parasympathetic efferent fibers as well as visceral afferent ones. The parasympathetic outflow reaching these nerves has been traced up all the way to the brainstem (via direct and indirect pathways), in some cases into the periaqueductal gray area (PAG) 510. Amongst other, the PAG 510 receives fibers from the TCC 502 and the NTS 504 and sends efferent fibers, amongst others, to the NTS 504, the dorsal motor nucleus of the vagus nerve (DMV) 204, and to the nucleus ambiguus (NA) 522.

Turning to FIG. 7, parasympathetic activity in the uterus 326 can be modulated by the activity at the NTS 504 as well as in the TCC 502; therefore, in one example, increasing the activity in the NTS 504 and the TCC 502 can be used to increase parasympathetic outflow into the uterus 326; consequently, increasing ACh release 702 in the uterus 326. Increasing the release of ACh 702 in the uterus 326 results in the higher activation of the existing α7nAChRs, thereby helping to minimize the endometriosis lesions. Further, in a recent study, researchers comparing normal and adenomyotic human tissue found that, as in the case of endometriosis, the levels of α7nAChR were significantly reduced in adenomyotic lesions. As stated before, larger availability of ACh 702 translates into higher activity in the existing α7nAChRs and as such can compensate for the lower count of these receptors and mitigate adenomyotic lesions as well.

In some implementations, methods and systems for treating endometriosis and/or adenomyosis involve stimulation of vagal fibers as well as trigeminal branches to activate both the NTS 504 and the TCC 502. For example, applying electrostimulation in a non-invasive manner with non-piercing electrodes to the skin located in close proximity to vagal and/or trigeminal neural fibers can result in NTS 504 and TCC 502 activity, thus progressively diminishing endometriosis lesions via an increase in uterus parasympathetic activity. In the circumstance of adenomyosis, in another example, applying non-invasive electrostimulation may slow or cease the progress of enlargement of the uterus. Further, certain blood-based biomarker tests, such as, in some examples, sFRP-4, BIGF, HGF.aAB, or S100-A12, may be performed to detect pathology (or lack thereof). The blood-based biomarker tests, for example, may be used in conjunction with trans-vaginal ultrasound, MRI, or a manual exam to evaluate the effectiveness of neurostimulation treatment. Finally, since the neurostimulation is directed to increasing activity levels of α7nAChR via an increase in ACh availability, evaluation of local ACh levels may be used to track effectiveness of treatment. Activation of vagal and/or trigeminal central targets results in an overall increase in parasympathetic activity. The same is true using a minimally invasive approach such as utilizing needles. An invasive approach, although less preferred, can also be used via implanted electrodes that, for example, wrap around the target nerves. Neurostimulation can be applied, in one example, targeting the cervical vagus along the lateral neck. In another example, the vagal nerve may be activated through ABVN 518 stimulation. The ABVN 518 may be stimulated in or around the auricle, such as, in some examples, at the cymba concha, the tragus, and/or at the base of the temporal bone (e.g., at or in close proximity to the mastoid canaliculus (a.k.a. Arnold's canal)). Trigeminal fibers may be stimulated, in a non-invasive approach or in a minimally invasive approach, for example, by targeting the trigeminal ophthalmic branches. The trigeminal ophthalmic branches, in some non-limiting examples, may be targeted by positioning one or more electrodes at the forehead or below the eye, or by targeting the auriculotemporal nerve (ATN) 530 (e.g., on the lateral aspect of the face, just in front of the ear, and/or on the upper portion of the auricle).

In some embodiments, endometriosis and/or adenomyosis are diminished by providing ABVN 518 and/or ATN 530 stimulation in and/or around the ear. Neurostimulation may be applied, for example, at least once every other day and for at least five minutes per session until the condition is resolved. For example, the stimulation treatment may be provided once within each forty-eight-hour period, once within each twenty-four-hour period, once within each twelve-hour period, or otherwise as desired by the patient to mitigate discomfort. The length of the stimulation treatment, in some examples, may include at least five minutes, between five minutes and ten minutes, up to twenty minutes, up to thirty minutes, and/or as long as symptoms remain. In circumstances in which the condition may not be fully resolved, the therapy may be applied indefinitely to control the condition.

Abnormal Uterine Bleeding

Abnormal uterine bleeding (AUB), including heavy menstrual bleeding (HMB), which in turn includes menorrhagia, is a condition affecting one in four women of reproductive age. This bleeding can be the result of a particular condition such as a bleeding disorder (e.g., hemophilia, Von Willibrand disease (vWD), or other) or it may be the result of no particular condition or an unknown condition(s). Although fatalities from AUB, including HMB, are rare, in some cases, if left untreated it can lead to cancer predisposition. HMB can lead women to a severe anemic condition which could in turn lead to shortness of breath and increase the risk of cardiac complications. HMB is very common, and although it is estimated that a fourth of the women of reproductive age suffer from it, about a third of reproductive age women actually seek treatment for what they consider to be a heavier than desired menstrual bleeding. HMB may produce lethargy and sleepiness in those who suffer from it.

Thus, new interventions that can help reduce the amount of blood loss in HMB and, generally, in those experiencing AUB are extremely desired and would be welcome by women and doctors alike, even if they are used as adjuvants.

Hemostasis, the process by which bleeding is stopped, is generally triggered by molecules that become exposed to circulating blood at a site of vascular injury. Sub-endothelial collagen (SEndC) and Tissue Factor (TF, aka coagulation Factor 3 or fIII) are examples of such molecules. While circulating platelets (i.e., thrombocytes) bind to exposed SEndC, TF binds to a particular circulating molecule called coagulation Factor 7 (fVII). The interaction between TF and fVII leads to the activation of fVII (fVIIa) and to the formation of the TF-fVIIa complex, which is called the Extrinsic Tenase (i.e., Extrinsic Xase). This TF-fVIIa complex initiates what is known as the coagulation cascade by activating coagulation Factor 10 (fX) and coagulation Factor 9 (fIX) into fXa and fIXa respectively (see below). Platelets adhering directly or indirectly to SEndC start to aggregate and form the initial plug to stop the bleeding. This plug is known as the platelet plug or thrombus. The platelet plug is then reinforced by the adherence and crosslinking of fibrin. The process leading to the formation of the platelet plug is commonly referred to as primary hemostasis whereas the process leading to the reinforcement of it by crosslinked fibrin (i.e., activated coagulation factor 1 or fIa) is known as secondary hemostasis. Platelets are anucleate blood cells mainly produced in bone marrow from megakaryocytes. Under normal conditions about 100 billion platelets are produced daily, leading to a concentration in blood that ranges between 150 to 400 million per milliliter. Platelets enter the vasculature circuit and, in humans, circulate for approximately 7 to 10 days before being removed by the liver and the spleen. Interestingly, as they circulate, they pool in the spleen where about a third of all circulating platelets are located at any given time. In humans, platelets transit time through the spleen is approximately 30 minutes.

Platelets contain, amongst others, mitochondria and two types of granules, the alpha granules (αG) and the dense or delta granules (δG). Ionized calcium (Ca2+ aka coagulation Factor 4 or fIV), a key component for coagulation, is stored inside the platelet at least within the mitochondria, the Dense Tubular System (DTS), as well as within the delta granules. Platelets circulate in the blood in an inactivated state and as such they do not aggregate; however, platelets become activated when they bind to exposed SEndC following an injury.

Platelets bind to SEndC directly via either the GP VI or the GP Ia/IIa receptors or indirectly through von Willebrand factor (vWF) via GP Ib-V-IX receptor. An activated platelet undergoes a shape change and secretes through its membrane the contents of its granules. The contents of the alpha granules include, among other components, fibrinogen (a.k.a. coagulation factor 1 or fI), platelet-derived growth factor (PDGF), vWF, TGF beta, coagulating Factor 5 (fV), platelet factor 4 (Pf4), and insulin-like growth factor 1 (IGF1). Delta granules (δG) contain, among other components, Ca2+, ADP, ATP, and serotonin (5-HT). Activated platelets promote changes to membrane receptors GP IIb/IIIa (aka integrin αIIbβ3) such that these receptors can bind to vWF as well as to fibrinogen. In addition, Thromboxane A2 (TxA2) is secreted from activated platelets. TxA2, and ADP activate circulating platelets which begin to aggregate with other activated platelets via GP IIb/IIIa-vWF-GP IIb/IIIa and GP IIb/IIIa-fibrinogen-GP IIb/IIIa bridges. This aggregation gives rise to platelet accumulation at the injury site generating the aforementioned platelet plug. This platelet plug, although weak, is the first step in limiting and eventually stopping blood from leaving the vascular system. Clot retraction is greatly influenced by the presence of the GP IIb/IIIa receptor on the platelet surface. Clot retraction assists in healing the wound by bringing the separated edges of the wound closer and closer together until the wound is healed. Thus, by promoting changes to the GP IIb/IIIa receptor, subjects that undergo therapy as described herein will enjoy the further benefit of accelerated time to heal.

As also mentioned earlier, the plug is then reinforced by fibrin fibers and further by the crosslinking of them by activated coagulation Factor 13 (fXIIIa). Fibrin is produced when circulating as well as platelet-secreted fibrinogen is converted into fibrin by thrombin (i.e., activated coagulation Factor2 or fIIa). In turn, thrombin is produced by cleavage from circulating prothrombin (a.k.a. coagulation factor 2-fII). Thrombin can be produced from prothrombin in relatively small amounts by fXa bound to platelet surfaces. Thrombin is not only able to turn fibrinogen into fibrin, but it can also activate other platelets as well as convert fV, coagulation Factor VIII (fVIII), coagulation Factor XI (fXI), and coagulation Factor 13 (fXIII) into their activated forms (fVa, fVIIIa, fXIa, fXIIIa respectively). fVa binds to fXa on the platelet surface in a Ca2+ dependent manner to form prothrombinase (fXa-fVa complex). The prothrombinase complex is capable of converting large quantities of prothrombin into thrombin. In fact, the prothrombinase complex cleaves thrombin from prothrombin at a rate that is hundreds of thousands of times faster (e.g., approximately 250,000 times) than fXa alone. Consequently, the presence of prothrombinase on the platelet surface greatly accelerates the coagulation process.

As stated before, fX can be activated into fXa by the Extrinsic Tenase; however, fX can also be activated by the Intrinsic Tenase, which is composed of fVIIIa and fIXa. In order for the Intrinsic Tenase to be assembled, both fVIII and fIX need to be activated. Thrombin can activate fVIII, and the Extrinsic Tenase and fXIa can activate fIX.

Figure 18:
FIG. 18 is a block diagram of example hemostatic pathways.

The pathway in which fXa is activated by the Extrinsic Tenase is generally known as the Extrinsic Pathway, and that in which fXa is activated by the Intrinsic Tenase is called the Intrinsic Pathway. The coagulation steps after the activation of fXa until the fibrin crosslinking by fXIIIa are termed the Common Pathway. As it can be appreciated from the text as well as from FIG. 18, which depicts the hemostatic pathways 1800, the role of thrombin is essential for hemostasis to take place.

Important to note is the remarkable quantitative difference between the Intrinsic Pathway 1802 and Extrinsic Pathway 1804. Under normal circumstances, compared to the Extrinsic Pathway 1804, thrombin 1806 is produced between 50 to 100 times faster via the Intrinsic Pathway 1802. Thus, it would be reasonable to state that under normal conditions the Extrinsic Pathway 1804 initiates the hemostatic process, but it is the Intrinsic Pathway 1802 that gets it to the finish line.

Platelets are not homogeneous; they exhibit marked differences which become evident after platelet activation during hemostasis. One of the most consequential differences amongst platelets subpopulations is that some activated platelets become procoagulant (although under debate, some refer to them as procoagulant collagen- and thrombin-activated or COAT platelets) while others activate into noncoagulating platelets (pro-aggregatory platelets). Whereas most of the thrombin 1806 is produced by procoagulant platelets, noncoagulating platelets are more prone to aggregate; thus, both types are needed for proper coagulation. Although there is large variability from subject to subject, on average, only 30% of activated platelets become procoagulant platelets.

In many or possibly all cases, procoagulant platelets swell and their phospholipid membrane becomes more negative due to exposure of phosphatidylserine (PS) on their membrane surface. Platelet membranes becoming more negative results in a significant increase in the binding affinity of prothrombinase to them; thus, prothrombinase is much more likely to bind to procoagulant platelets (pCP) than to non-coagulating (nCP) ones. Since, as mentioned before, prothrombinase 1808 can produce thrombin 1806 up to two hundred and fifty thousand times (250,000 times) faster than fXa alone, it is clear that most of the thrombin 1806 at or near the injury site will be produced on pCP.

Given the hemostatic processes discussed above, it is evident that even small increases in the pCP/nCP ratio can increase the rate of thrombin production at or near the bleeding site, thus accelerating platelet and fXIII activation as well as fibrin production. Thus, in addition to leading to faster platelet aggregation, increases in thrombin generation also leads to increases in the rate of fibrin binding and crosslinking 1810 which altogether promotes shorter bleeding times and lower bleeding volumes.

Further, faster/higher production of thrombin 1806 at the bleeding site can compensate deficits and limitations in the hemostasis process (e.g., bleeding/coagulation disorders), such as, for example, a lower production or a lack of Intrinsic Tenase 1812 production due to deficiencies or lower than normal (including complete lack of) fVIII, fIX, or fXI, which is respectively the case in Hemophilia A, Hemophilia B, and Hemophilia C. One manner in which this compensation may occur is by locally increasing the ratio of procoagulant/anticoagulant activity at or near the bleeding site.

A strong activation is necessary for a platelet to activate as a procoagulant platelet (pCP); however, this is not sufficient. Experiments using double agonist (e.g., collagen and thrombin) have been shown to produce a small percentage of platelet activation into procoagulant types. Some have suggested that the COAT acronym is inaccurate since not only is activation by both collagen and thrombin insufficient to provide a considerable boost in platelet activation into procoagulant types, but it is also not unique. It is not unique in the sense that a very large concentration of thrombin can also activate platelets into procoagulant types. Several elements have been identified as contributing factors to determining whether or not, upon activation, a platelet becomes procoagulant. Some of these elements include platelet age, size, number of mitochondria, number as well as content of granules, and baseline Ca2+ concentration. Interestingly, under similar circumstances, younger platelets are more likely to become procoagulant than older ones (as stated earlier, in humans, platelets circulate for about 7 to 10 days before being removed by the liver and/or spleen).

Data from a recent study by Abbasian and colleagues showed that the cytosolic Ca2+ concentration ([Ca2+]cyt) in pCP was at least 50 times higher than the [Ca2+]cyt in nCP (>100 nM vs. 1-2 nM). See Abbasian, Nima, et al. "Supramaximal calcium signaling triggers procoagulant platelet formation." Blood Advances 4.1 (2020): 154-164. Most platelets can activate as pCP if treated with Ca2+; however, in general, most platelets activate as nPC if stimulated with some platelet activators. This suggests that [Ca2+] cyt is one, if not the most significant, factor in determining if a platelet activates as a pCP or as a nCP.

Platelets have several transmembrane Ca2+ channels which allow Ca2+ exchange between extracellular and intracellular spaces (see table below). More than one of these channels or a combination of them could be activated to allow a net positive Ca2+ influx, thus incrementing the total amount of Ca2+ in the platelet. Within the platelet, this Ca2+ is usually taken by one or various mechanisms into internal storages, amongst which are the mitochondria, the dense tubular system (DTS), lysosomes, and the δG. A high [Ca2+] cyt could lead to platelet activation, which if it happens at a location other than at an injury site, may lead to an undesired thrombotic event. Thus, it is important that Ca2+ is sequestered into internal (e.g., intracellular) storages such that it is only released into the cytosolic space upon an injury-related activation. This could be achieved in different ways; for example, by inducing an influx of Ca2+ into the platelet by activating one of the transmembrane Ca2+ channels and temporarily or transiently blocking or partially blocking the mechanisms responsible for the release of Ca2+ from internal storages into the cytosolic space. This rise in baseline Ca2+ (e.g., total intracellular pre-activation Ca2+ not in the cytosolic space) can increase the likelihood of higher [Ca2+] cyt upon activation, thereby incrementing the overall probability for platelets to activate as pCP, leading to a higher coagulation potential. In the event of an injury, a higher coagulation potential translates, on an individual basis, to a higher thrombin production at the injury site. A higher than otherwise production of thrombin at an injury site translates into a faster and localized platelet activation as well as fibrin adhesion and crosslinking onto the thrombus. Therefore, a higher coagulation potential can result in a faster coagulation process leading to lower bleeding volumes and shorter bleeding times.

TABLE 1

| Platelet Transmembrane Calcium Channels Platelet Transmembrane Calcium Channel Table | |
| --- | --- |
| Channel | Calcium flow |
| α7-Nicotinic Acetylcholine Receptor (nAChRα7) | IN |
| calcium-release activated calcium modulator 1 (CRACM1 or Orai1) | IN |
| Canonical Transient Receptor Potential 6 (TRPC6) | IN |
| Purinergic receptor, P2X1 | IN |
| Na$^+$/Ca$^{2+}$ exchanger | IN |
| plasma membrane Ca$^{2+}$ ATPases (PMCAs) | OUT |

Platelets that have undergone changes that increase their hemostatic capabilities, such as increased coagulation potential, are referred to herein as platelets with enhanced function. The enhancement of platelet function can be achieved through various mechanisms described herein, including modulating autonomic nervous system activity to influence platelet priming in the spleen. The increased coagulation potential of these enhanced-function platelets can be assessed by various methods including, amongst others, shortened bleeding time, decreased bleeding volume, changes in platelet surface protein expression, clotting time, and/or clot strength measurements.

As shown by Schedel and colleagues, platelets express the α7-Nicotinic Acetylcholine Receptor (nAChRα7). See Schedel, Angelika, et al. "Human platelets express functional α7-nicotinic acetylcholine receptors." Arteriosclerosis, thrombosis, and vascular biology 31.4 (2011): 928-934. Since the autonomic nervous system (ANS) can control the release of Acetylcholine (ACh), and given that the nAChRα7 is a transmembrane Ca$^{2+}$ channel, the presence of nAChRα7 on the platelet membrane suggests that platelet Ca$^{2+}$ influx can be modulated by the ANS. Further, since Bennett, et al. showed that ACh inhibits platelet activation, it follows that ACh can be used to increase Ca$^{2+}$ via the nAChRα7 while preventing platelet activation. See Bennett J A, Ture S K, Schmidt R A, Mastrangelo M A, Cameron S J, Terry L E, Yule D I, Morrell C N, Lowenstein C J. Acetylcholine Inhibits Platelet Activation. J Pharmacol Exp Ther. 2019 May; 369 (2): 182-187.

Interestingly, the sympathetic and parasympathetic fibers interact at the celiac ganglia, where both can influence the activity of postganglionic sympathetic fibers enervating the spleen. In particular, sympathetic preganglionic efferent fibers (SPgF) normally coming from the T5-T9 spinal cord levels leave the spine as the spinal root that becomes the greater splanchnic nerve and synapse onto postganglionic neurons at the celiac ganglion. The SPgF release ACh as they synapse on their target at the celiac ganglia. Fibers leaving the celiac ganglia form what is known as the celiac plexus, fibers from which continue as the splenic plexus. The splenic nerve, which arises from fibers in the splenic plexus, enervates the spleen. The activity of the SPgF is modulated, amongst other things, by activity in the RVLM, which in turn is modulated by activity in both the TCC and the LC. It is worth noting that the ABVN also connects to trigeminal regions, in particular to the trigeminal spinal nucleus, which for purposes of the present document is considered part of the TCC. Consequently, activation of SPgf via, amongst others, activity in the TCC and/or in the LC and/or the activation of vagal efferent fibers (VEF) can modulate the production of $Ca^{2+}$ enriched platelets via a common pathway following their interaction at the celiac ganglia.

Figure 17A:
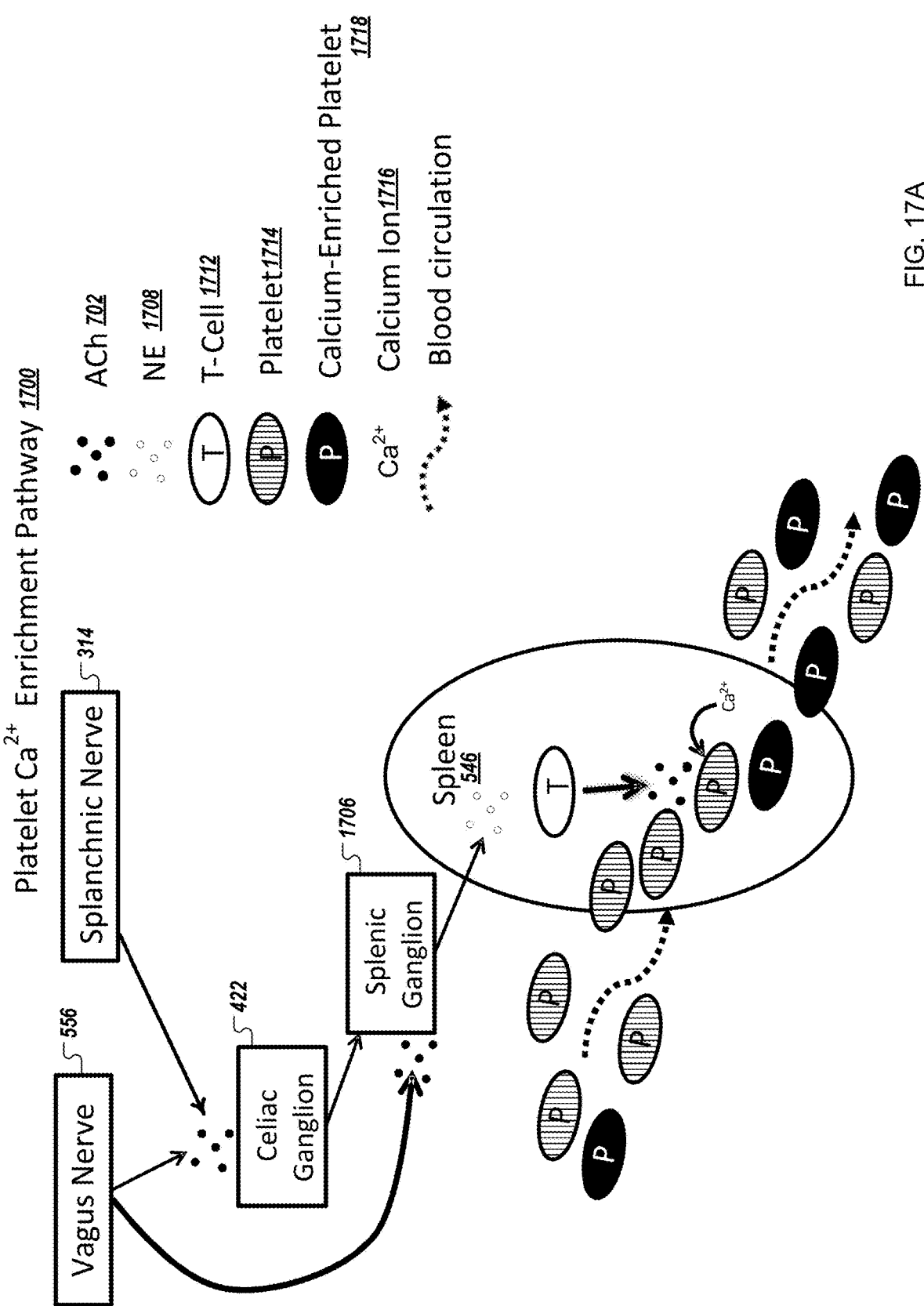
FIG. 17A is a block diagram of an example platelet calcium-enrichment pathway.

Turning to FIG. 17A, an example block diagram of a platelet $Ca^{2+}$ enrichment pathway 1700 is illustrated. Acetylcholine (ACh) 702, a natural agonist of the nAChRα7, is an important neurotransmitter that modulates many aspects in the ANS. Increasing activity in the parasympathetic branch of the ANS (e.g., the parasympathetic nervous system—PNS), for example by activating vagal efferent fibers of the vagus nerve 556, can trigger the release of ACh 702 in the celiac ganglion 422 and/or in the splenic ganglion 1706. The same is true when increasing the activity of the splanchnic nerves 314 synapsing on the celiac ganglion 422, as they too release ACh 702. Innervation of the spleen 546 is carried out via neural connections between the splenic ganglion 1706 and their targets in the spleen 546, where norepinephrine (NE) 1708 is released. Interestingly, Rosas-Ballina showed that NE 1708 released in the spleen 546 activates T-cells 1712 which in turn releases ACh 702. See Rosas-Ballina et al. Acetylcholine-synthesizing T cells relay neural signals in a vagus nerve circuit. Science. 2011 Oct. 7; 334(6052):98-101. doi: 10.1126/science.1209985. Epub 2011 Sep. 15. PMID: 21921156; PMCID: PMC4548937. This ACh 702, upon reaching the nAChRα7 on the platelets 1714 which are slowly circulating through the spleen 546, can trigger a $Ca^{2+}$ 1716 influx into the platelets 1714, effectively increasing their baseline $Ca^{2+}$ 1716 and resulting in calcium-enriched platelets 1718, which may also be referred to herein as primed platelets. This detailed description refers to the celiac ganglion 422 and to the splenic ganglion 1706; however, the splenic ganglion 1706 is sometimes considered an extension of the celiac ganglion 422. Further, it is understood that many ganglia form what is called a plexus (e.g., plexus 1706). As such, for the purpose of the description herein, plexus and ganglion are interchangeable.

Figure 17B:
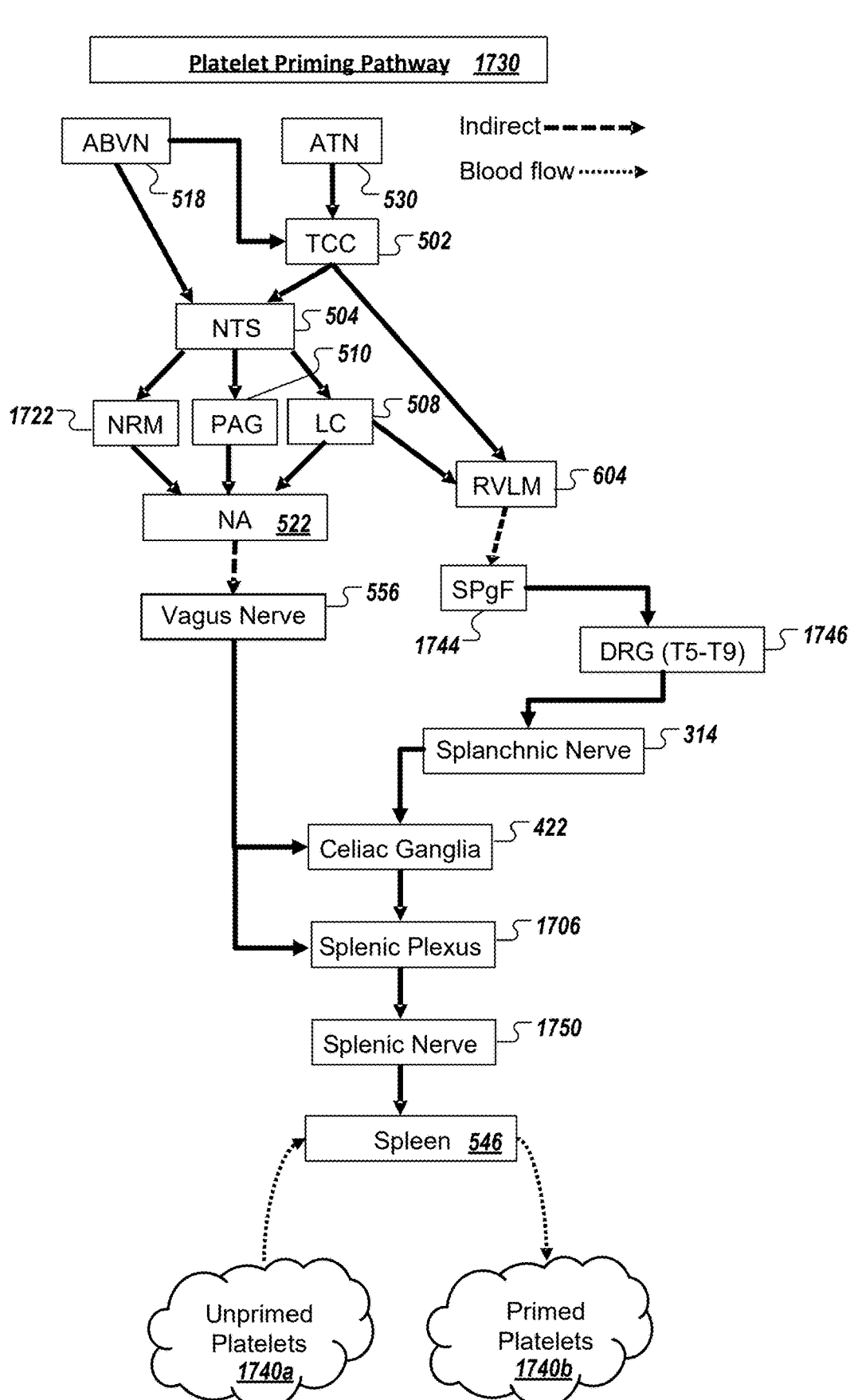
FIG. 17B is a block diagram of an example platelet priming pathway.

Turning to FIG. 17B, in some embodiments, platelets are primed via activation of a Platelet Priming Pathway 1730 which stimulates activity in the spleen 546. In particular, the ABVN 518 and/or the ATN 530 may be stimulated which have projections to the NTS 504. As illustrated, the TCC 502 receives afferent connections from the ATN 530 and projects to the NTS 504 as well as to the RVLM 604, while the ABVN 518 projects directly to the NTS 504.

As seen in FIG. 17B, certain platelet priming pathways also involve other nuclei or regions such as Locus Coeruleus (LC) 508, Periaqueductal Gray (PAG) 510, and nucleus raphe magnus (NRM) 1722. Each of these nuclei or regions feed, in turn, to the nucleus ambiguous (NA) 522 which provides a pathway to the vagus nerve 556. Other regions also feeding the vagus nerve 556 are the dorsal motor nucleus of the vagus (DMV) (not illustrated) as well as the spinal trigeminal nucleus (herein considered part of the TCC 502). The indirect stimulation of the vagus nerve 556 via the various pathways allows the vagus nerve 556 to enervate the celiac ganglia 422 and/or the splenic plexus 1706. The splenic nerve 1750, which arises from fibers in the splenic plexus 1706, enervates the spleen 546, thereby increasing platelet priming in the spleen 546, resulting in more unprimed platelets 1740a being converted to primed platelets 1740b. For example, stimulation using a low mid-range pulse at a low frequency on the Arnold's nerve, and/or a low mid-range pulse at a high frequency on the ATN 530 for a short duration may lead to a noticeable increase in primed platelets, which, for example, could be assessed by a decrease in PT.

In another path illustrated in FIG. 17B, the LC 508 and TCC 502 each provide a pathway to the RVLM 604 which provides a pathway for indirectly stimulating the sympathetic preganglionic efferent fibers (SPgF) 1744, which exit the spine via the dorsal root ganglion (DRG) at the T5-T9 level 1746 to form the greater splanchnic nerve 314 leading to the stimulation of postganglionic nerves at the celiac ganglia 422, further triggering splanchnic nerve 314 activity. Since the splanchnic nerve 314 feeds to the celiac ganglia 422, as described in relation to the vagus nerve-related pathways above, the indirect stimulation of the SPgF 1744 via the various pathways illustrated and described increases platelet priming in the spleen 546, resulting in more unprimed platelets 1740a being converted to primed platelets 1740b. As with the pathways via the vagus nerve 556, stimulation using a low mid-range pulse at a low frequency on the Arnold's nerve, and/or a low mid-range pulse at a high frequency on the ATN 530 for a short duration may lead to a noticeable increase in primed platelets, which, for example, could be assessed by a decrease in PT.

Returning to FIG. 17A, given that platelets with higher baseline $Ca^{2+}$ 1716 are more likely to activate as pCP, and thus increase the overall coagulation potential of the subject; it is evident that any situation in which a higher coagulation potential is desired will benefit from a method which, when applied to a subject, results in a net influx of $Ca^{2+}$ 1716 into the platelets 1714. Increasing the activity in VEF 556, as stated above, can trigger a cascade of events leading to a net influx of $Ca^{2+}$ 1716 into platelets 1714 while they are transiting through the spleen 546.

Stimulations for generating one or more of the responses described herein, such as generating a pressor response, a trigemino-parasympathetic response, and/or an increase in coagulation potential (CPot), in some embodiments, are applied periodically, e.g., in repetitive patterns. In some examples, the stimulations may be applied once every five minutes, once time every ten minutes, once every thirty minutes, once every hour, up to eight times per day, or once per day. The duration may vary based in part on frequency of the periodic stimulation. In some examples, stimulations may be applied once every ten minutes for a short duration, once every hour for a medium duration, or once per day for a long duration (see Table 4 for example duration ranges). In another embodiment, in order to reduce total blood loss and/or total monthly bleeding days, a female suffering from HMB/menorrhagia, including those with any coagulation disorder, could, for example, start stimulation a few days before starting her menstrual period and continue stimulation until the end of menstruation. In such a case, stimulation could be applied, for example, once daily or once every other day for a very short or a short period of time. Other schedules are possible based on, in some examples, convenience, comfort, strength of desired effect, and/or potential severity of the outcome (e.g., likelihood of harm to the patient due to lack of/inadequate prophylactic treatment).

Irregular Menstrual Bleeding

Irregular menstrual bleeding is common in individuals diagnosed with polycystic ovary syndrome, although irregular menstrual bleeding has many causes, including perimenopause. In some embodiments, methods and systems for treating irregular menstrual bleeding include increasing the P/S ratio by applying electrostimulation in a non-invasive manner with non-piercing electrodes to the skin located in close proximity to vagal and/or trigeminal neural fibers. The vagal and/or trigeminal neural fibers may be stimulated, in other embodiments, using a minimally invasive approach such as utilizing needles. An invasive approach, although less preferred, can also be used via implanted electrodes that, for example, wrap around the target nerves. Neurostimulation can be applied, in one example, targeting the cervical vagus along the lateral neck. In another example, the vagal nerve may be activated through ABVN stimulation. The ABVN may be stimulated in or around the auricle, such as, in some examples, at the cymba concha, the tragus, and/or at the base of the temporal bone (e.g., at or in close proximity to the mastoid canaliculus). Trigeminal fibers may be stimulated, in a non-invasive approach or in a minimally invasive approach, for example, by targeting the trigeminal ophthalmic branches. The trigeminal ophthalmic branches, in some non-limiting examples, may be targeted by positioning one or more electrodes at the forehead or below the eye, or by targeting the auriculotemporal nerve (ATN) (e.g., on the lateral aspect of the face, just in front of the ear, and/or on the upper portion of the auricle).

In some embodiments, irregular menstrual cycles are treated by providing ABVN and/or ATN stimulation in and/or around the ear. Auricular neurostimulation therapy may be provided, in an example, at least one time per day and at least for seven minutes per session such that symptoms diminish to a manageable level in everyday activities. For example, the stimulation treatment may be provided once within each twenty-four-hour period, once within each twelve-hour period, or more frequently in at least an initial phase of treatment. The length of the stimulation treatment, in some examples, may include at least seven minutes, between seven minutes and ten minutes, up to twenty minutes, up to thirty minutes, and/or longer.

Figure 15A:
FIG. 15A is a graph of example stimulation results representing reduction in bleeding volume.
Figure 15A:
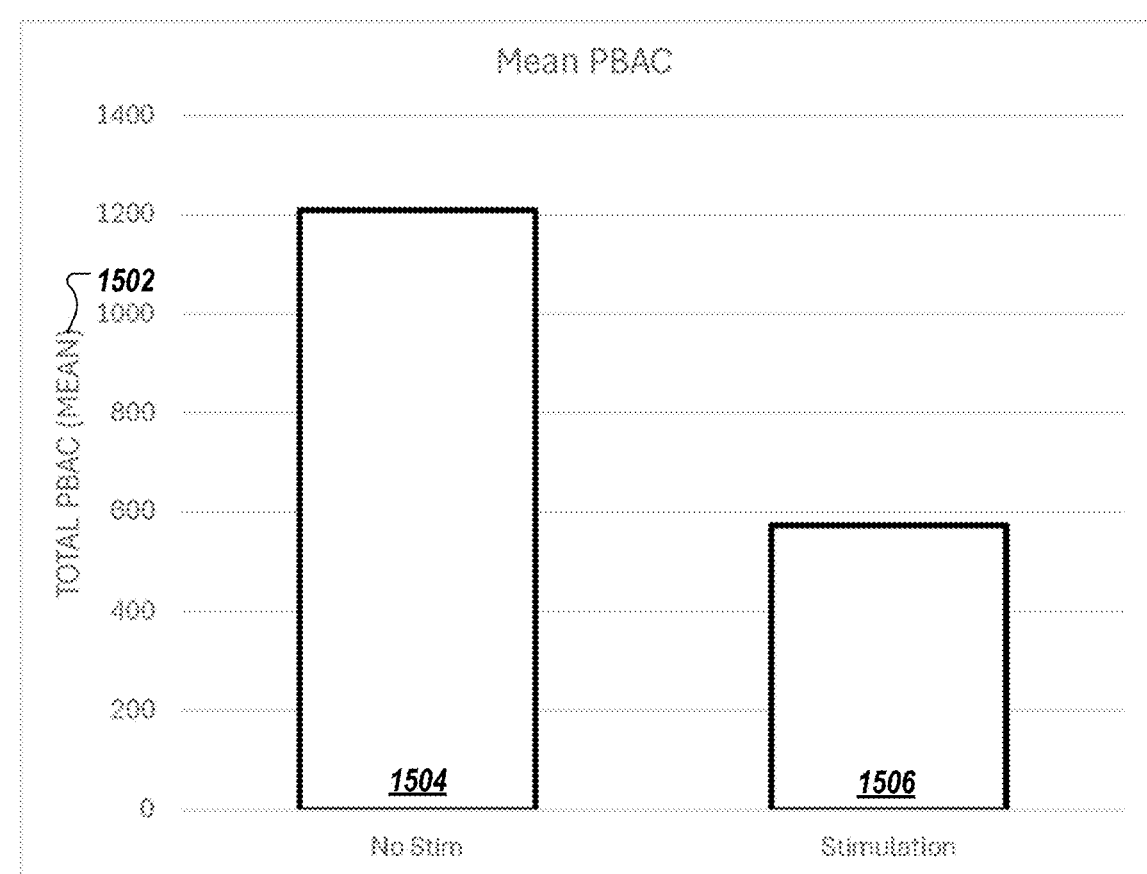
Figure 15B:
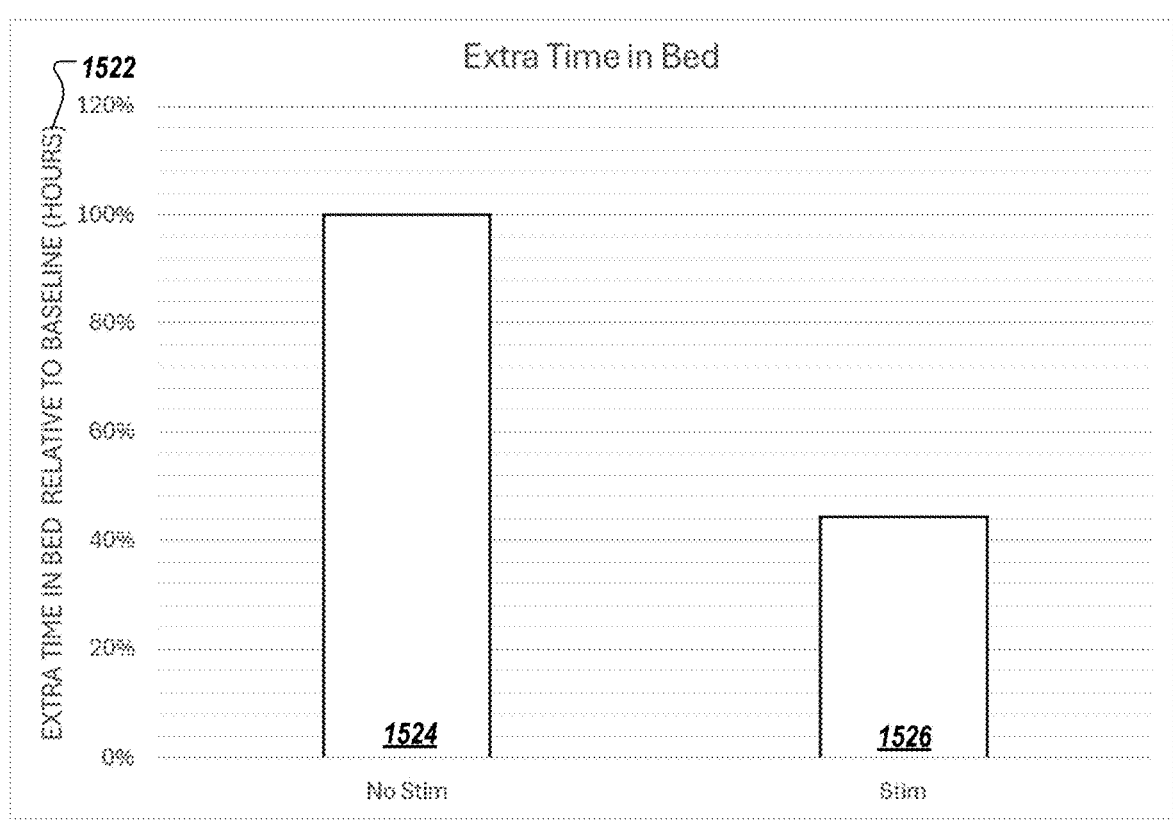
FIG. 15B is a graph of example stimulation results representing reduction of time spent in bed.

Human Trial Results in Neurostimulation Therapy for Treating Menstruating Subjects The inventors have produced the first human data using non-invasive neuromodulation showing a meaningful reduction of blood loss during menstruation, including a decrease in menstruation days and accompanied by a decrease in sleepiness as well as menstrual pain (see FIG. 3B). During menstruation, a group of women were provided with a menstrual chart and scoring system referred to as the Pictorial Blood Loss Assessment Chart (PBAC) for tracking approximate menstrual volume each day. The PBAC is a tool used by clinicians to measure response of menorrhagia to different forms of treatments. FIG. 15A and FIG. 15B, respectively, show the PBAC scores and the extra time spent in bed for two different menstrual cycles, one in which stimulation was not delivered, and a second one in which stimulation was delivered for 1 hour twice a day starting from when the menstrual period started. Turning to FIG. 15A, a graph illustrates example stimulation results 1500, the results demonstrating a 53% average reduction in total PBAC score 1502 (e.g., the PBAC score is a bit under 600 for the stimulation group 1504 compared to a score that is touch above 1200 for the no stimulation group 1506). This significant reduction in total PBAC score demonstrates a high reduction in blood loss. Turning to FIG. 15B, a graph illustrates example inactivity results 1520 representing extra hours spent in bed (e.g., outside of typical sleeping duration) during menstruation (e.g., due to fatigue, overwhelming pain, discomfort, etc.). In comparison with the extra time in bed 1522 spent during the menstrual cycle without stimulation 1524, when benefitting from stimulation sessions twice per day, the women undergoing neurostimulation therapy 1526 experienced approximately a 56% reduction in extra hrs. spent in bed as compared to their prior menstrual cycle in which no stimulation was delivered.

Figure 16:
FIG. 16 is a graph of example stimulation results representing reduction in menstrual cycle symptom severity.
Figure 16:
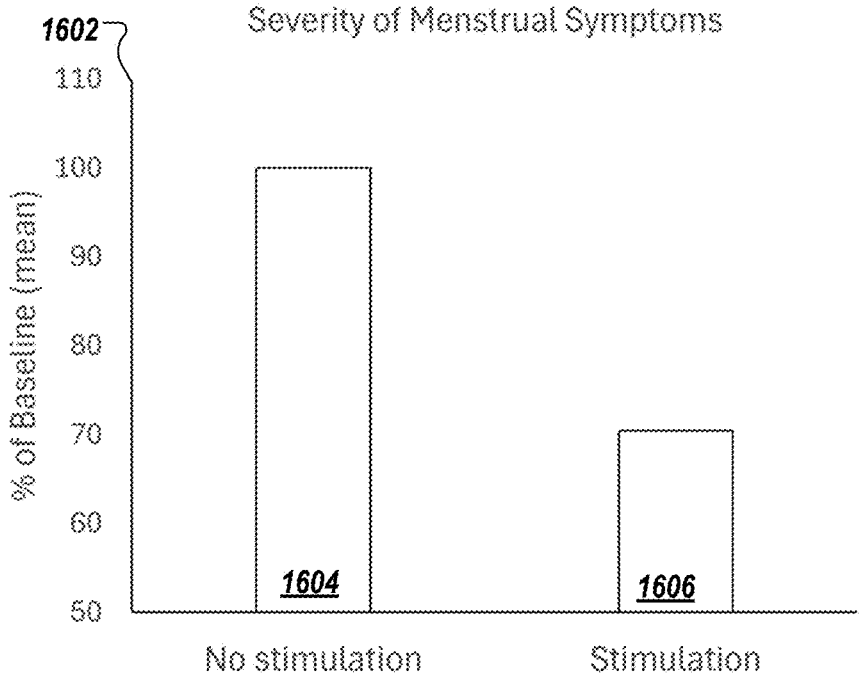

Further validating and expanding upon the previously reported pain reduction and decreased bed rest time, a comprehensive assessment of menstrual symptom severity was conducted using the Cox Menstrual Symptom Scale (CMSS). The CMSS assessment, which evaluates both frequency and severity across a set of eighteen distinct symptoms, including both physical and psychological manifestations, demonstrates that the therapeutic benefits of neurostimulation extend beyond pain management to address the full spectrum of menstrual symptoms. As illustrated in FIG. 16, in accordance with feedback provided by participants using the CMSS, neurostimulation therapy resulted in a substantial reduction in overall symptom severity. When comparing menstrual cycles with stimulation 1606 to baseline cycles without stimulation 1604, as illustrated in a graph 1600, the average severity of menstrual symptoms decreased to approximately 70% of baseline levels 1602, representing a 30% reduction in overall symptom severity. This finding complements our earlier observations of a 63% reduction in pain scores (FIG. 3B) and 56% reduction in additional time spent in bed (FIG. 15B), providing a more complete picture of the therapy's broad impact across multiple symptom domains.

Figure 15C:
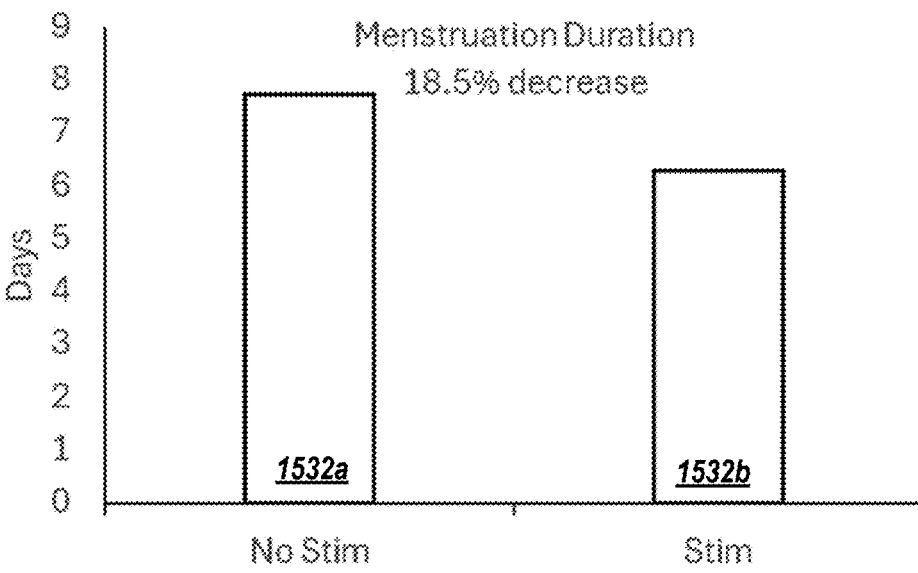
FIG. 15C is a graph of example stimulation results representing reduction in bleeding days.

FIG. 15C illustrates a graph 1530 presenting example stimulation results showing reduction in menstruation duration for women suffering from heavy menstrual bleeding (HMB). The graph compares the average duration of menstruation in days between a no stimulation subject group 1532a and a stimulation subject group 1532b. Subjects receiving neurostimulation therapy 1532b experienced an 18.5% decrease in menstruation duration, from approximately 7.7 days without stimulation to 6.3 days with stimulation. This reduction in bleeding duration, combined with the previously reported reduction in blood loss volume described in relation to FIG. 15A, demonstrates the therapy's effectiveness in treating HMB through multiple outcome measures.

FIG. 20A through FIG. 20E illustrate graphs of example stimulation results representing relative improvement in health-related quality of life in menstruating subjects treated using neurostimulation therapy as described herein. The data was collected using the 36-item short form health survey (SF-36) questionnaire, a validated health-related quality of life (HRQOL) assessment tool scored from 0 to 100, with higher scores indicating better health status.

Figure 20A:
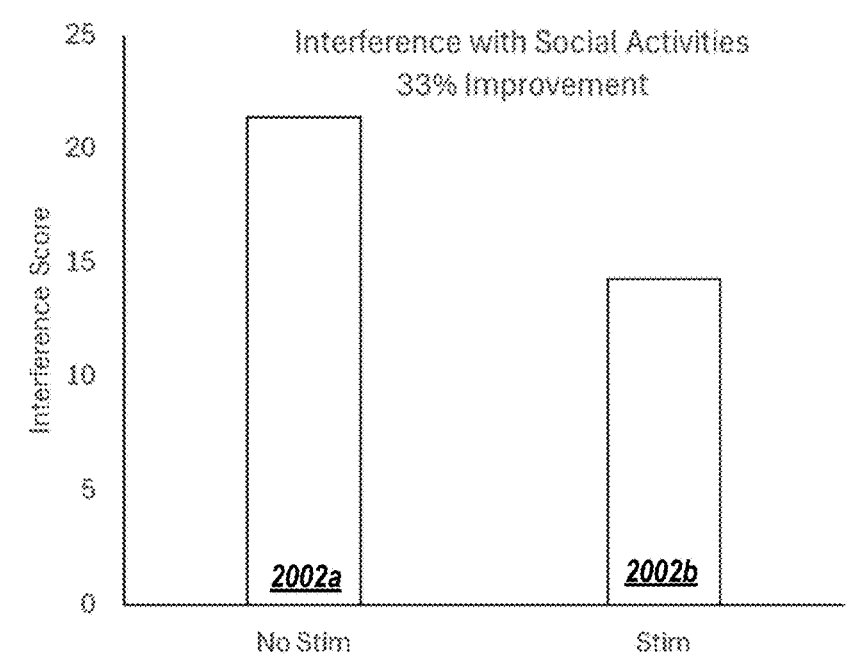
FIG. 20A through FIG. 20E illustrate graphs of stimulation results representing improvements in menstrual-related symptoms achieved with neurostimulation.

Turning to FIG. 20A, a graph 2000 illustrates interference scores as a distance from optimal health (score of 100), where a lower score indicates less interference with social activities. As illustrated, when subjects received neurostimulation therapy 2002b there was a 33% improvement in social activity interference compared to when stimulation was not applied 2002b, demonstrating the therapy's effectiveness in improving social functioning during menstruation.

Figure 20B:
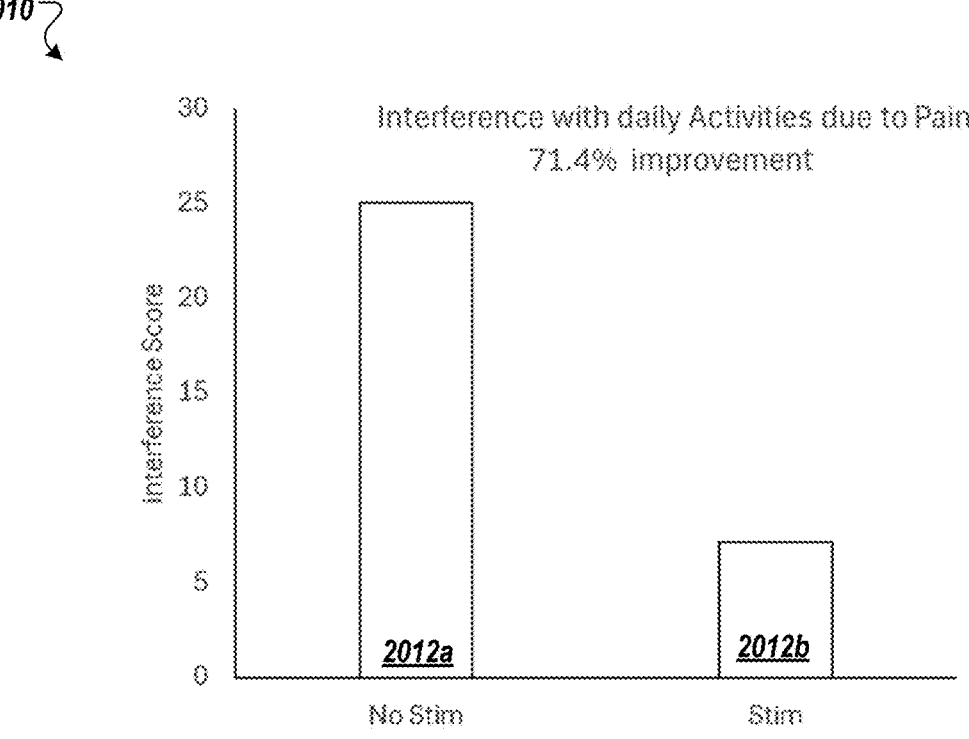

FIG. 20B illustrates a graph 2010 demonstrating example stimulation results showing reduction in pain-related interference with daily activities. Using the same SF-36 scoring methodology, where the values represent the distance from optimal health (score of 100), when subjects received neurostimulation therapy 2012b, they experienced a remarkable 71.4% improvement in their ability to perform daily activities compared to when stimulation was not applied 2012a. This substantial improvement suggests that the neurostimulation therapy effectively mitigates pain-related limitations in daily functioning during menstruation.

Figure 20C:
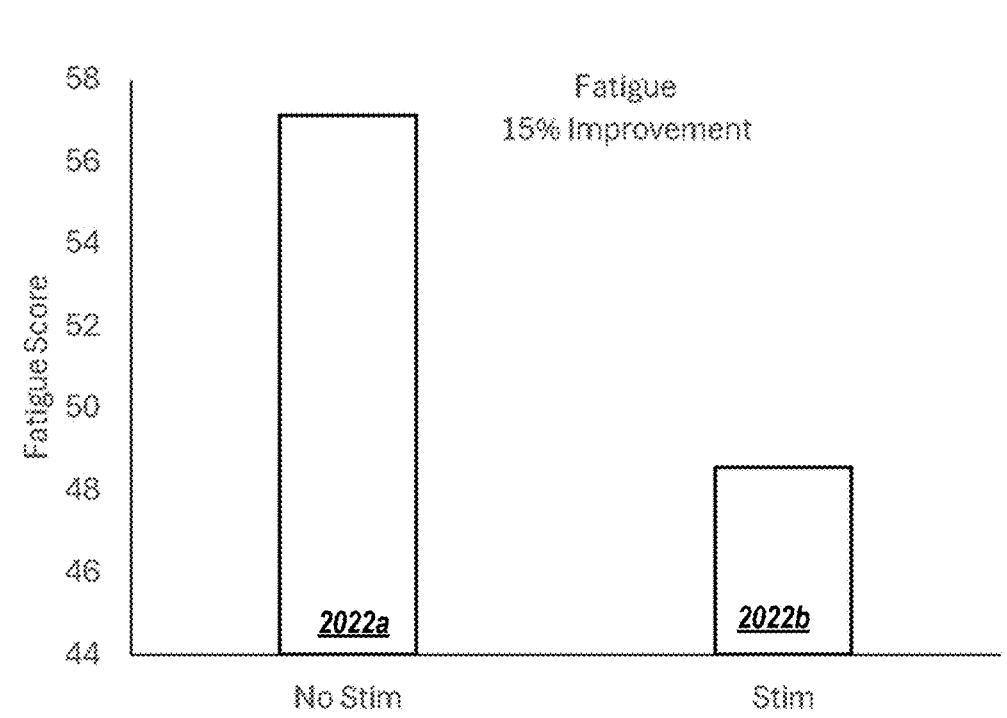

FIG. 20C illustrates a graph 2020 presenting example stimulation results demonstrating improvement in fatigue levels. The graph shows fatigue scores derived from the SF-36 questionnaire, where the values represent distance from optimal energy levels (score of 100). When subjects received neurostimulation therapy 2022*b* they showed a 15% improvement in fatigue levels compared to when no stimulation was applied 2022*a*, supporting the earlier discussion regarding the therapy's ability to modulate fatigue through NTS-LC pathway activation and subsequent increases in NE availability.

Figure 20D:
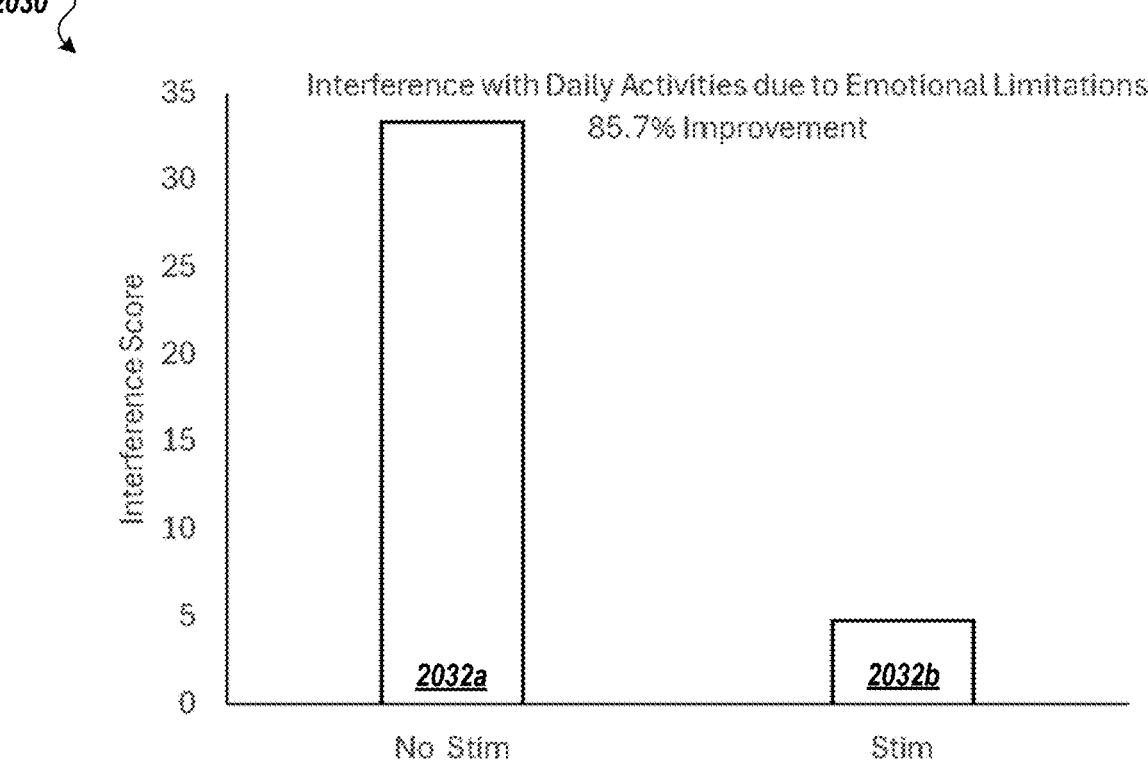

FIG. 20D illustrates a graph 2030 presenting example stimulation results showing reduction in emotional limitation interference with daily activities. Using the SF-36 questionnaire scoring methodology, where values represent distance from optimal health (score of 100), when subjects received neurostimulation therapy 2032*b*, they demonstrated a substantial 85.7% improvement in emotional-related interference compared to when no stimulation was applied 2032*a*. This marked improvement suggests that the neurostimulation therapy effectively addresses the emotional aspects of menstruation-related symptoms, likely through modulation of serotonergic pathways and autonomic balance.

Figure 20E:
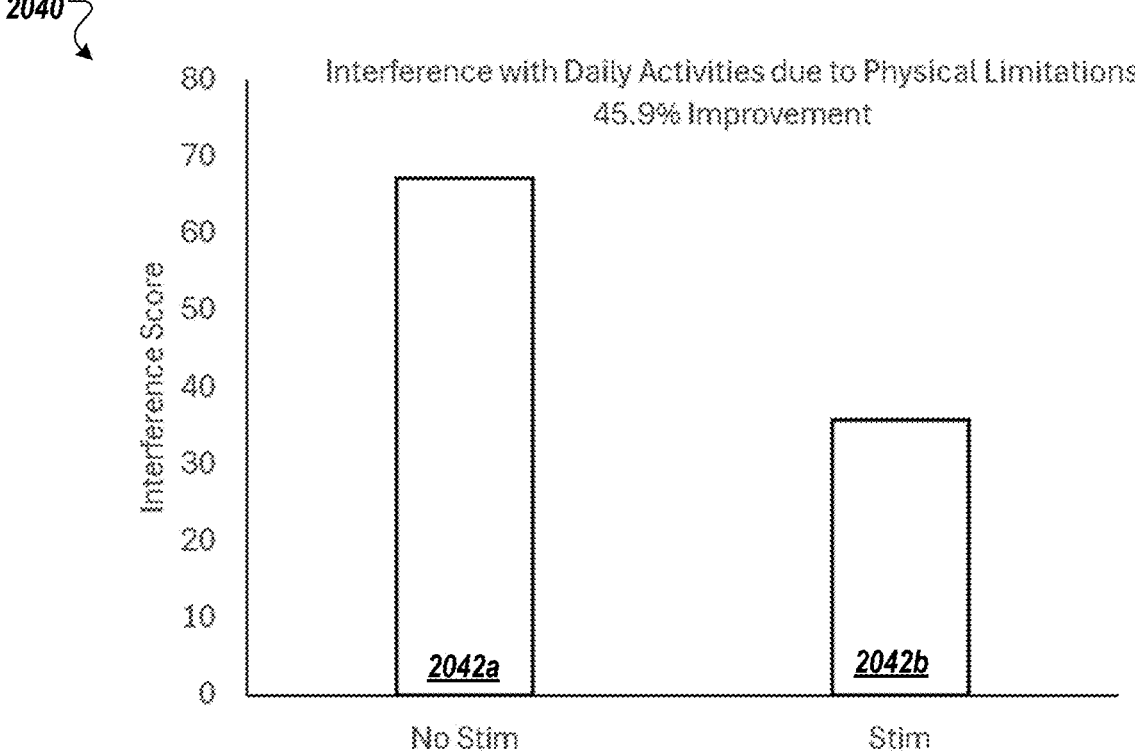

FIG. 20E illustrates a graph 2040 of example stimulation results demonstrating improvement in physical limitation interference with daily activities. The data, collected using the SF-36 questionnaire where values represent distance from optimal health (score of 100), shows that when subjects received neurostimulation therapy 2042*b*, they experienced a 45.9% improvement in physical limitation interference compared to when no stimulation was applied 2042*a*. This significant reduction in physical limitations demonstrates the therapy's effectiveness in addressing the physical symptoms associated with menstruation.

Example Stimulation Parameters

In some embodiments, stimulation pulses are delivered in pulse patterns. Individual pulses in the pattern may vary in frequency and/or pulse width. Patterns may be repeated in stimulation cycles. The pulse pattern, for example, may be designed in part to ramp up stimulation, establishing a comfort level in the wearer to the feel of the stimulation. In another example, the pulse pattern may be designed in part to alternate stimulation between stimulation sites where two or more sites are being stimulated during therapy. In examples involving multiple stimulation sites, the stimulation pattern may be designed such that stimulating frequencies are not the same in all sites at which stimulation is being delivered.

In some embodiments involving electrical stimulation utilizing either percutaneous or transcutaneous (i.e., non-penetrating) electrodes, the stimulation frequencies vary within a set of ranges. For example, the stimulation frequencies applied in a stimulation pattern may include a first or low frequency within a range of about 1 to 30 Hz, a second or mid-range frequency within a range of about 30 to 70 Hz, a third or high frequency within a range of about 70 to 150 Hz; and/or a fourth or very high frequency within a range of about 150 to 300 Hz.

TABLE 2

| Electrical therapy: Frequency Table | |
| --- | --- |
| Frequency designation | Range in Hz |
| Low frequency | 1-30 |
| Mid-range frequency | 30-70 |
| High frequency | 70-150 |
| Very high frequency | 150-300 |

TABLE 4

| Example Stimulation Durations Stimulation Duration Table | |
| --- | --- |
| Very Short Duration | 1-5 min. |
| Short Duration | 5-15 min. |
| Medium Duration | 15-60 min. |
| Long Duration | 1-5 hrs. |
| Very Long Duration | 5-24+ hrs. |

TABLE 5

| Example Treatment Periods Treatment Period Table | |
| --- | --- |
| Brief Period | <5 min. |
| Very Short Period | 5-15 min. |
| Short Period | 15-60 min. |
| Medium Period | 1-5 hrs. |
| Long Period | 5-24 hrs. |
| Very Long Period | 1-7 days |
| Extremely Long Period | 7-30+ Days |

In one embodiment, a stimulation frequency is varied between 2 Hz and 100 Hz. In yet another embodiment, the pulse width can be adjusted from between 20 and 1000 microseconds to further allow therapy customization. Stimulation frequency is an important differentiator between neural networks; for example, using a high frequency has been shown to be beneficial in activating the desired trigeminal system features; in contrast, a low frequency is preferred in activating the desired vagal features. Thus, in a preferred embodiment, a combination of low frequency and high frequency is applied respectively to activate vagal and trigeminal branches in accordance with various embodiments described herein. In yet another embodiment, a variable frequency (e.g., stimulating at a non-constant frequency) can be used at one or more of the electrodes. The variable frequency can be a sweep, and/or a random/pseudo-random frequency variability around a central frequency (e.g., 15 Hz+/−1.5 Hz, or 100 Hz+/−10 Hz). Varying the stimulation frequency in a random or pseudo-random way can help to prevent neural accommodation, and in some cases achieve qualitatively different results. In a particular case, it may produce the opposite effect of that produced using a single frequency. For example, in some cases the P/S ratio may be increased using a single frequency but decreased using the same frequency as the center frequency of a pseudo-random varying frequency around that center frequency.

When using electrical stimulation, different combinations of pulse widths can be used at each electrode. Pulse widths, in some examples, may range from one or more of the following: first or short pulse widths within a range of about 10 to 50 microseconds, or more particularly between 10 to 20 microseconds, 20 to 30 microseconds, 30 to 40 microseconds, 40 to 50 microseconds; second or low mid-range pulse widths within a range of about 50 to 250 microseconds, or more particularly between 50 to 70 microseconds, 70 to 90 microseconds, 90 to 110 microseconds, 110 to 130 microseconds, 130 to 150 microseconds, 150 to 170 microseconds, 170 to 190 microseconds, 190 to 210 microseconds, 210 to 230 microseconds, or 230 to 250 microseconds; third or high mid-range pulse widths within a range of about 250 to 550 microseconds, or more particularly between 250 to 270 microseconds, 270 to 290 microseconds, 290 to 310 microseconds, 310 to 330 microseconds, 330 to 350 microseconds, 350 to 370 microseconds, 370 to 390 microseconds, 390 to 410 microseconds, 410 to 430 microseconds, 430 to 450 microseconds, 450 to 470 microseconds, 470 to 490 microseconds, 490 to 510 microseconds, 510 to 530 microseconds, or 530 to 550 microseconds; fourth or long pulse widths within a range of about 550 to 1000 microseconds, or more particularly between 550 to 600 microseconds, 600 to 650 microseconds, 650 to 700 microseconds, 700 to 750 microseconds, 750 to 800 microseconds, 800 to 850 microseconds, 850 to 900 microseconds, 900 to 950 microseconds, or 950 to 1000 microseconds; and/or a fifth or very long pulse widths within a range of about 1000 to 4000 microseconds or more particularly between 1000 to 1250 microseconds, 1250 to 1500 microseconds, 1500 to 1750 microseconds, 1750 to 2000 microseconds, 2000 to 2250 microseconds, 2250 to 2500 microseconds, 2500 to 2750 microseconds, 2750 to 3000 microseconds, 3000 to 3250 microseconds, 3250 to 3500 microseconds, 3500 to 3750 microseconds, 3750 to 4000 microseconds. Different embodiments can use different ranges of pulse widths at one or more of the electrodes. The selection of the stimulation pulse width depends on the desired target fiber as well as the output intensity. For example, given a similar intensity, activation of C type fibers generally requires a longer pulse width than activation of a myelinated Aβ fiber. In a preferred embodiment, the use of a low mid-range pulse is used in order to preferably activate myelinated fibers.

TABLE 3

| Electrical Therapy: Pulse Width Table | |
| --- | --- |
| Pulse width designation | Range in microseconds |
| Very short pulse | 10-50 |
| Short pulse | 50-150 |
| Low mid-range pulse | 151-350 |
| High mid-range pulse | 351-550 |
| Long pulse | 551-1000 |
| Very long pulse | 1001-4000 |

Activity on the VEF can be modulated by electrical stimulation at various sites. For example, the vagus nerve ascends inside the carotid sheath along the neck (e.g., cervical vagus) where it can be non-invasively stimulated in a transcutaneous way, for example using patch electrodes or a device such as the one described by U.S. Pat. No. 10,207, 106 to Simon et al. The cervical vagus can also be stimulated invasively using an implanted electrode powered externally, or using a fully implantable system such as the system described in U.S. Pat. No. 8,571,654 to Libbus et al. The implantable system, for example, may provide low frequency stimulation (e.g., 1 to 30 Hz) to the cervical vagus and/or descending vagal pathways. These same invasive/implantable methods can be used to stimulate the splenic nerve and thus increase spleen activity. Other methods of stimulation can be used such as, in some examples, ultrasound, which can also be used to directly activate the spleen (see, e.g., U.S. Patent Application Publication No. 2011/0190668 to Mishelevich), or light (see, e.g., U.S. Pat. No. 8,562,658 to Shoham et al.).

Activity on the VEF can also be modulated by stimulating the auricular branch of the vagus nerve (ABVN) and/or by stimulating a branch of the trigeminal nerve. Each of these pathways activate neurons in the Nucleus of the Solitary Track (NTS) which directly and indirectly increases VEF activity. Trigeminal nerves approach the subcutaneous region at several locations in the face; for example, the auriculotemporal nerve (ATN), the Supraorbital nerve, Supratrochlear nerve, Infratrochlear nerve, Palpebral branch of lacrimal nerve, External nasal nerve, Infraorbital nerve, Zygomaticofacial nerve, Zygomaticotemporal nerve, Mental nerve, and Buccal nerve are potential trigeminal targets to deliver transcutaneous stimulation. A device placing electrodes such that any of these branches is stimulated can be used activate the VEF. For example, a device such as the one described by U.S. Pat. No. 10,207,106 to Simon et al. could be utilized to stimulate a branch of the vagus nerve. In a similar manner, the device described by U.S. Pat. No. 8,914,123 to Rigaux can be used to stimulate a branch of the trigeminal nerve. Further, although cumbersome, both devices could be used simultaneously or in an alternating manner to elicit a vagal, a trigeminal, or a trigemino-vagal response. The ABVN can be stimulated at the auricle, the preferential targets for this purpose being the cymba concha, the concha, the tragus and/or inside the ear canal, as well as behind the ear in or around the mastoid canaliculus (McS); a.k.a. Arnold's canal. The ATN can be stimulated in or around the auricle; for example immediately rostral to the auricle on top of and/or above the temporomandibular joint (TMJ). The ABVN as well as the trigeminal nerve branches can be activated individually, simultaneously, or sequentially, such as in an interleaved manner. Further, these nerves can be stimulated invasively using percutaneous electrodes (e.g., as described by U.S. Pat. No. 8,942,814 to Szeles) or as in U.S. Patent Application Publication No. 2018/0200522 to Taca Jr.) or non-invasively using transcutaneous electrodes (e.g., as described by U.S. Pat. No. 11,351,370 to Covalin et al., incorporated herein by reference in its entirety).

Figure 10A:
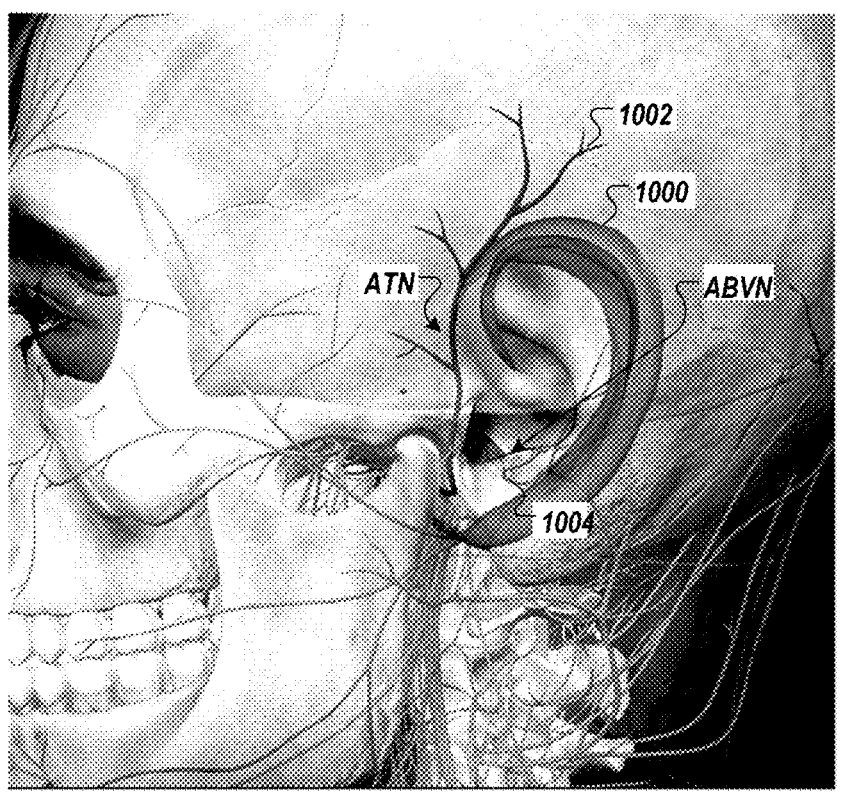
FIG. 10A through FIG. 10D, FIG. 11, and FIG. 12 illustrate example target nerve regions for directing therapy using a wearable auricular neurostimulator (WANS) apparatus.
Figure 10B:
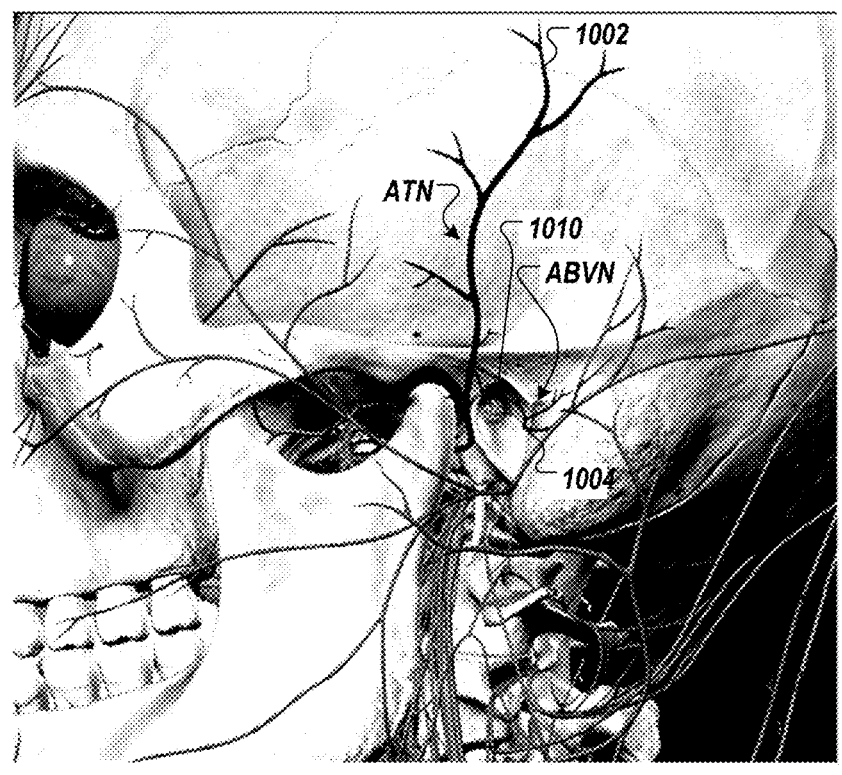

Turning to FIG. 10A and FIG. 10B, for example, ATN 1002 is illustrated in relation to an ear 1000 of a person (FIG. 10A), running generally in front of the ear 1000, as well as in relation, skeletally (FIG. 10B), to an ear canal 1010. In an illustrative example, an electrode may be positioned in proximity to the temporomandibular joint.

Figure 10C:
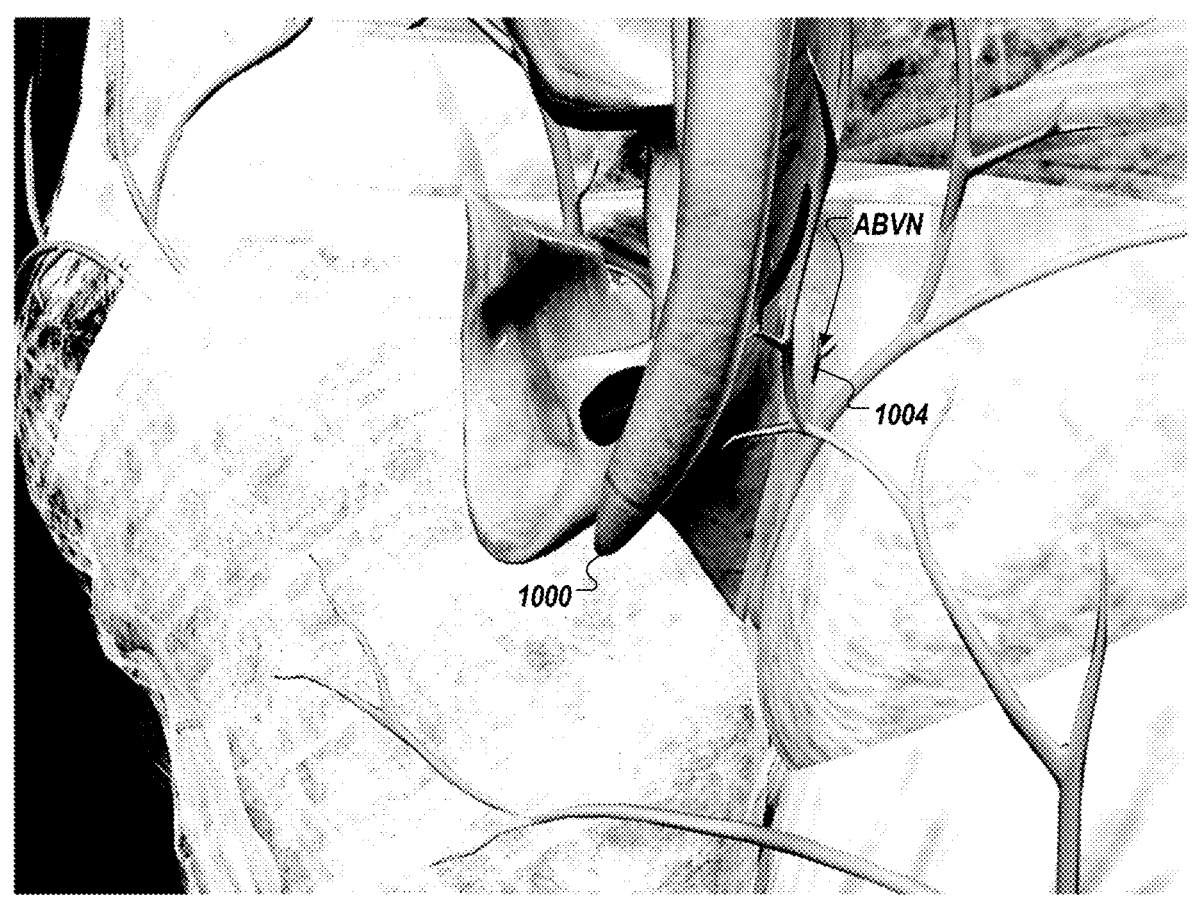
Figure 10D:
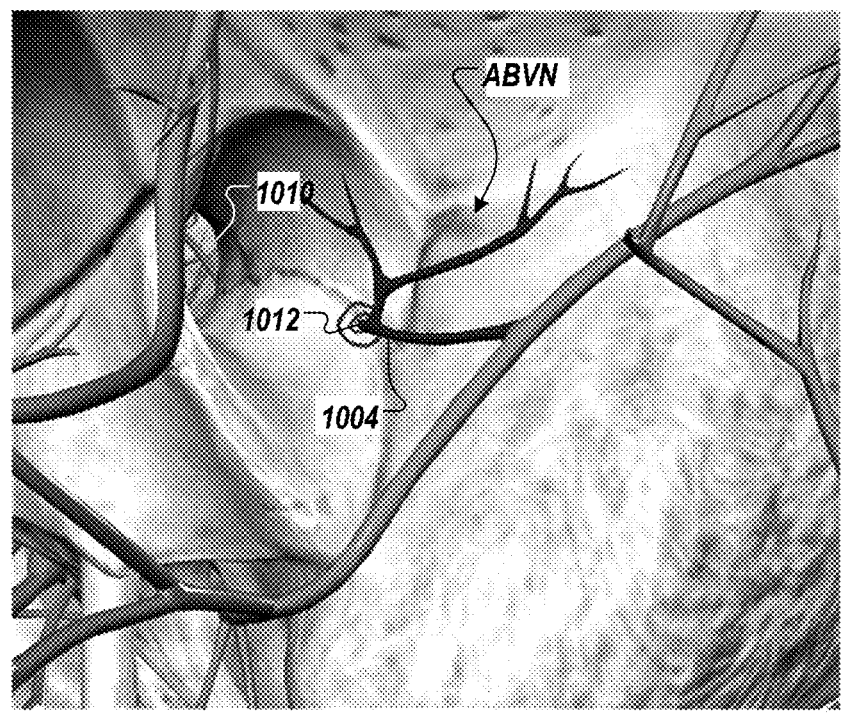
Figure 11:
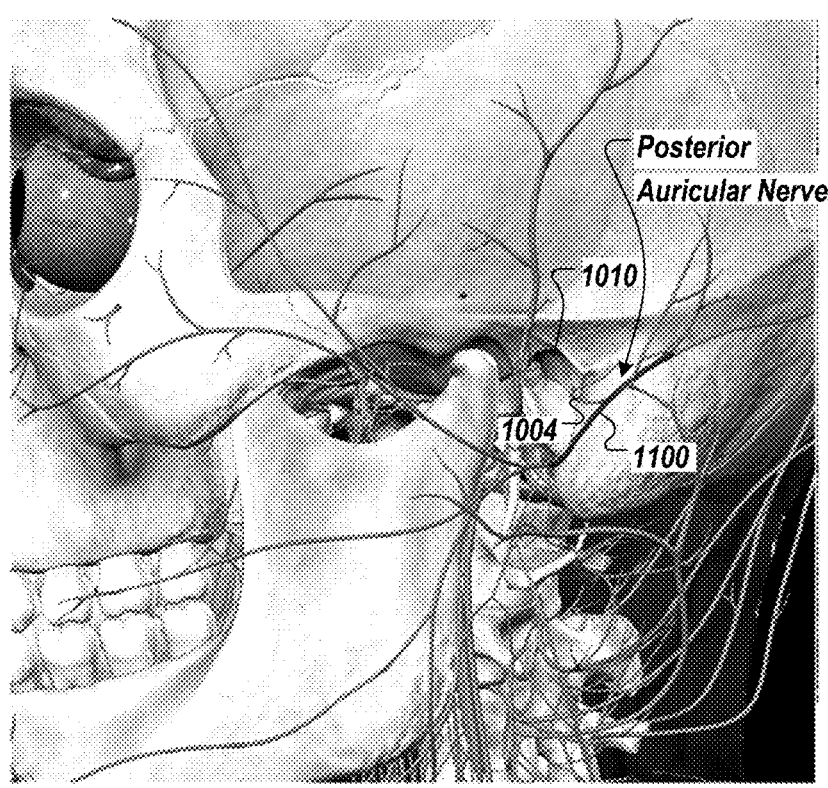

In some embodiments, an electrode of a neurostimulation device as described herein is configured to contact skin of a wearer in a region of nerve structures of the auricular branch of the vagus nerve (ABVN) and/or nerve structure connected to the ABVN such that delivery of therapeutic stimulations via the electrode modulates ABVN activity. As shown in FIG. 10A through FIG. 10D for example, ABVN 1004 is illustrated as it surfaces (FIG. 10D) through the mastoid canaliculus (MsC) 1012 (a.k.a., Arnold's canal) and in relation to the ear 1000 (FIG. 10A), in relation to the ear canal 1010 (FIG. 10B) and in relation to the back of the ear (FIG. 10C). Turning to FIG. 11, posterior auricular nerve 1100 meets a branch of the ABVN, providing another target for ABVN stimulation. In an illustrative example, an electrode in electrical communication with the conductive adhesive region may be positioned in proximity to the MsC.

Figure 12:
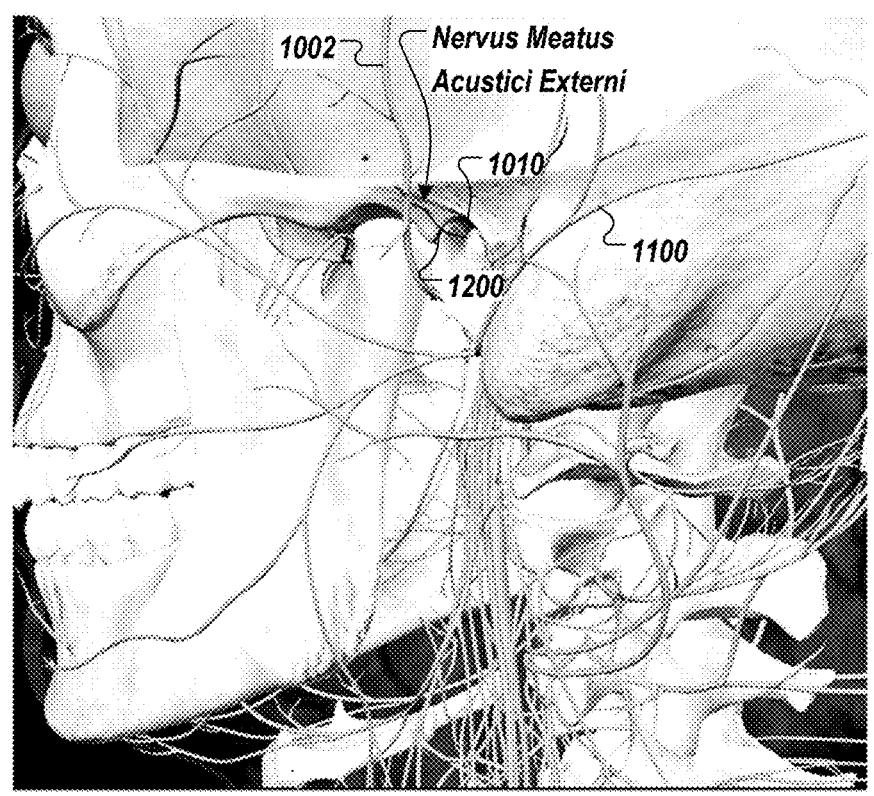

Turning to FIG. 12, an electrode, for example, may be positioned to stimulate the nervus meatus acustici externi branch 1200 of the ATN 1002. In other embodiments, in order to stimulate branches of the ABVN, the conductive adhesive region is positioned on the concha, on the cymba concha, or on the tragus.

Example Devices and Stimulation Paths

Figures 8A, 8B, 8C, 8D:
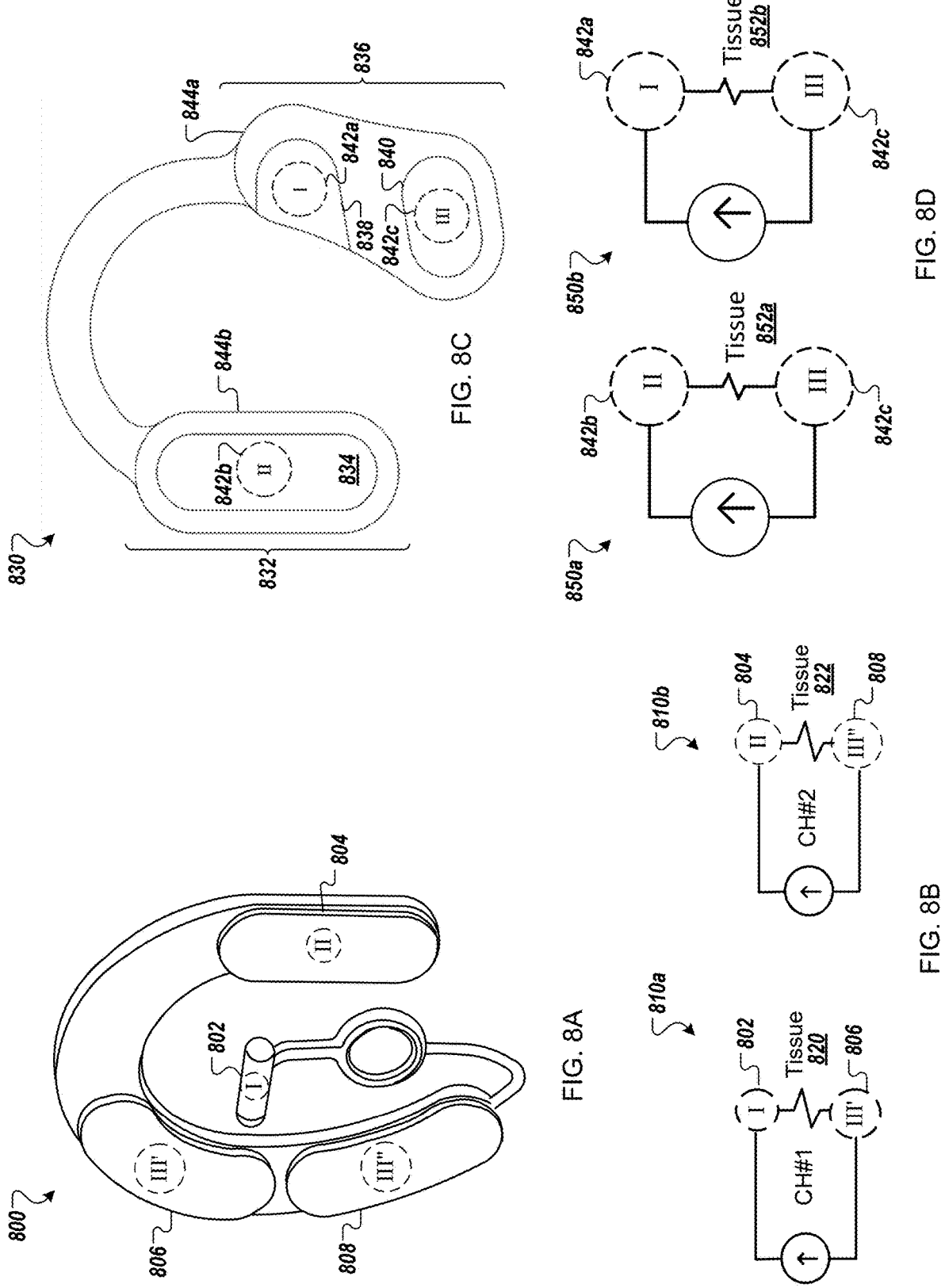
FIG. 8A and FIG. 8B are diagrams representing of an electrode configuration and an equivalent circuit for providing therapy according to a first example.
FIG. 8C and FIG. 8D are diagrams representing of an electrode configuration and an equivalent circuit for providing therapy according to a second example.

Turning to FIG. 8C, a WANS apparatus 830 includes a forward portion 832 including a conductive adhesive region 834 with a surrounding non-conductive adhesive region 844b and a rear portion 836 including conductive adhesive regions 838 and 840 with a surrounding non-conductive adhesive region 844a. The non-conductive adhesive regions 844a, 844b, for example, may provide extra adhesion for a robust skin/conductive adhesive contact. The conductive adhesive region 834 of the forward portion 832, for example, corresponds to a second electrode (II) 842b. Turning to the rear portion 836, the conductive adhesive region 838 corresponds to a first electrode (I) 842a, and the conductive adhesive region 840 corresponds to a third electrode (III) 842c. In some embodiments, the electrodes 842a-c and their corresponding conductive adhesive regions 834, 838, and 840 each have a similar shape and area. In other embodiments, the shape and/or surface area of each of the electrodes 842a-c and/or their corresponding conductive adhesive regions 834, 838, and 840 may differ, for example based on the underlying target nerve structures and/or the shape of the anatomy on which the electrodes 842a-c and their corresponding conductive adhesive regions 834, 838, and 840 are configured to be positioned.

The conductive adhesive region 834, in some implementations, is configured to contact skin of a wearer in a region of nerve structures of the auriculotemporal nerve (ATN) and/or nerve structures connected to the ATN, such that delivery of therapeutic stimulation via the conductive adhesive region 834 modulates ATN activity. Turning to FIG. 10A and FIG. 10B, for example, ATN 1002 is illustrated in relation to an ear 1000 of a person (FIG. 10A), running generally in front of the ear 1000, as well as in relation, skeletally (FIG. 10B), to an ear canal 1010. In an illustrative example, an electrode in electrical communication with the conductive adhesive region 834 may be positioned in proximity to the temporomandibular joint.

In some embodiments, the conductive adhesive region 838 is configured to contact skin of a wearer in a region of nerve structures of the auricular branch of the vagus nerve (ABVN) and/or nerve structure connected to the ABVN such that delivery of therapeutic stimulations via the conductive adhesive region 838 modulates ABVN activity. As shown in FIG. 10A through FIG. 10D for example, ABVN 1004 is illustrated as it surfaces (FIG. 10D) through the mastoid canaliculus (MsC) 1012 (a.k.a., Arnold's canal) and in relation to the ear 1000 (FIG. 10A), in relation to the ear canal 1010 (FIG. 10B) and in relation to the back of the ear (FIG. 10C). Turning to FIG. 11, posterior auricular nerve 1100 meets a branch of the ABVN, providing another target for ABVN stimulation. In an illustrative example, an electrode in electrical communication with the conductive adhesive region 838 may be positioned in proximity to the MsC.

The conductive adhesive region 840, in some embodiments, is configured to contact skin of the patient as a return electrode, thereby forming an electrical circuit across the tissue with the electrodes corresponding to each of the forward conductive adhesive region 834 and the rear conductive adhesive region 836. Although illustrated as a single return electrode (e.g., third electrode 842c) provided for both electrodes 842a and 842b corresponding to adhesive region 838 and adhesive region 834, in other embodiments, a different, separate return electrode may be provided for each electrode 842a, 842b. In further embodiments, three or more return electrode paths may be provided for the two positive electrodes. Other combinations are possible.

Figure 8E:
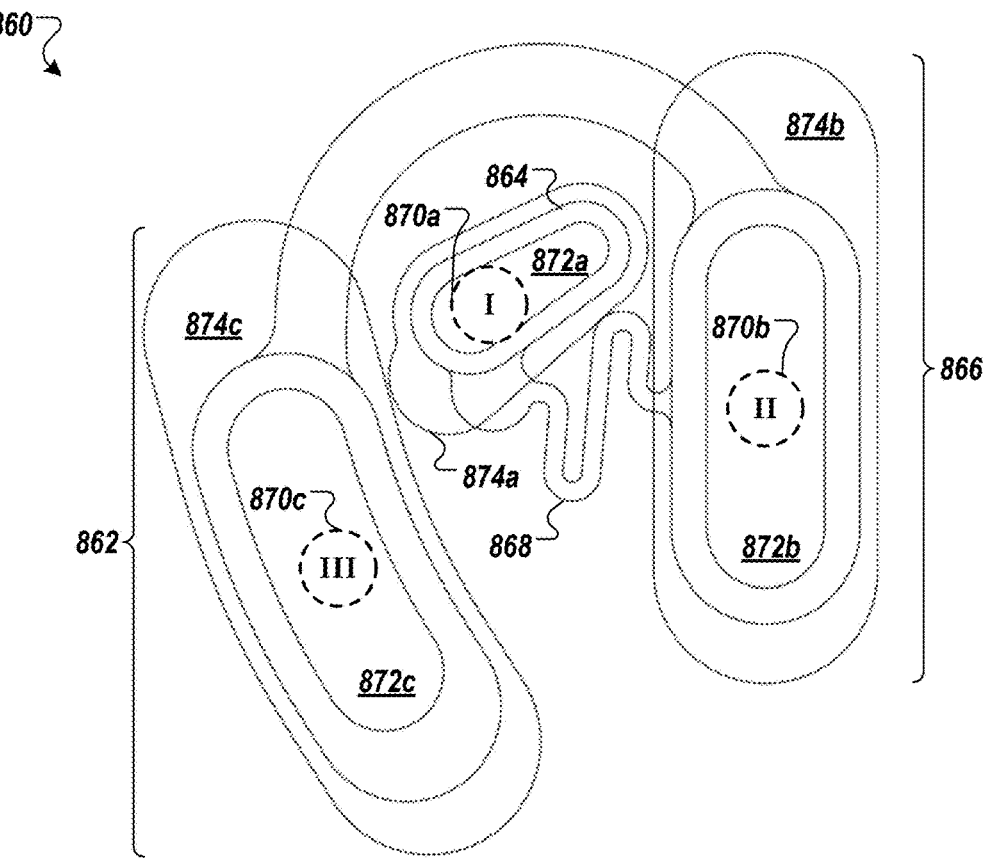
FIG. 8E and FIG. 8F are diagrams representing of an electrode configuration and an equivalent circuit for providing therapy according to a third example.

Turning to FIG. 8E, a wearable auricular neurostimulator (WANS) 860 includes a forward portion 866, a rear portion 862, and an on-ear portion 864, each portion including at least one electrode (e.g., electrodes 870a, 870b, and 870c). When donned by a wearer, the WANS 860 may be wrapped around the ear such that forward portion 866 is disposed in front of the ear and the rear portion 862 is disposed behind the ear. The on-ear portion 864, connected to the forward portion 866 by a flexible connector 868, may be frictionally and/or adhesively retained in a cymba region of the ear.

To increase engagement of the WANS 860 with tissue of the wearer and/or to enhance electrical communication between the tissue and the electrodes 870a-c, in some embodiments, each electrode 870a-c is disposed in electrical communication with a corresponding conductive adhesive region 872a-c. The conductive adhesive regions 872a-c may create an electrical communication path from an electrode positioned in or on the WANS 860 to skin of the wearer. To protect and maintain cleanliness of the conductive adhesive regions 872a-c prior to wearing, in some implementations, the WANS 860 is provided with one or more liners, such as the liners 874a-c. To provide robust skin contact, in some implementations, the conductive adhesive regions 872a-c are surrounded by one or more non-conductive adhesive regions. In some embodiments, the electrodes 870a-c and their corresponding conductive adhesive regions 872a-c have a similar shape and area. In other embodiments, the size and/or shape varies electrode-to-electrode and/or adhesive region-to-adhesive region, for example based on the targeted underlying nerve structures and/or the topography of the anatomy on which the particular electrode and adhesive region are configured to be positioned.

The conductive adhesive region 872a may be provided to create an electrical communication path from the electrode 870a positioned on the on-ear portion 864 of the WANS 860 to skin of the wearer in an anterior part of the ear canal. Turning to FIG. 12, such an electrode, for example, may be positioned to stimulate the nervus meatus acustici externi branch 1200 of the ATN 1002. In other embodiments, in order to stimulate branches of the ABVN, the conductive adhesive region 872a is positioned on the concha, on the cymba concha, or on the tragus.

Turning to FIG. 8E, a wearable auricular neurostimulator (WANS) 860 includes a forward portion 866, a rear portion 862, and an on-ear portion 864, each portion including at least one electrode (e.g., electrodes 870a, 870b, and 870c). When donned by a wearer, the WANS 860 may be wrapped around the ear such that forward portion 866 is disposed in front of the ear and the rear portion 862 is disposed behind the ear. The on-ear portion 864, connected to the forward portion 866 by a flexible connector 868, may be frictionally and/or adhesively retained in a cymba region of the ear.

To increase engagement of the WANS 860 with tissue of the wearer and/or to enhance electrical communication between the tissue and the electrodes 870a-c, in some embodiments, each electrode 870a-c is disposed in electrical communication with a corresponding conductive adhesive region 872a-c. The conductive adhesive regions 872a-c may create an electrical communication path from an electrode positioned in or on the WANS 860 to skin of the wearer. To protect and maintain cleanliness of the conductive adhesive regions 872a-c prior to wearing, in some implementations, the WANS 860 is provided with one or more liners, such as the liners 874a-c. To provide robust skin contact, in some implementations, the conductive adhesive regions 872a-c are surrounded by one or more non-conductive adhesive regions. In some embodiments, the electrodes 870*a-c* and their corresponding conductive adhesive regions 872*a-c* have a similar shape and area. In other embodiments, the size and/or shape varies electrode-to-electrode and/or adhesive region-to-adhesive region, for example based on the targeted underlying nerve structures and/or the topography of the anatomy on which the particular electrode and adhesive region are configured to be positioned.

The conductive adhesive region 872*a* may be provided to create an electrical communication path from the electrode 870*a* positioned on the on-ear portion 864 of the WANS 860 to skin of the wearer in an anterior part of the ear canal. Turning to FIG. 12, such an electrode, for example, may be positioned to stimulate the nervus meatus acustici externi branch 1200 of the ATN 1002. In other embodiments, in order to stimulate branches of the ABVN, the conductive adhesive region 872*a* is positioned on the concha, on the cymba concha, or on the tragus.

Turning to FIG. 8A and FIG. 8B, in a preferred embodiment, stimulation may be provided transcutaneously using an auricular stimulation device 800. The auricular stimulation device 800 is shown having electrodes 802, 804, 806, and 808. The electrodes 802, 804, 806, and 808, for example, may be configured to form corresponding circuits 810*a* and 810*b* according to an example. In an example, equivalent circuit 810*a* may be formed by electrode 802 and electrode 806 which are configured to stimulate tissue portion 820. In this example, tissue portion 820 is positioned to target the cymba conchae region which is enervated by branches of the auricular branch of the vagus nerve and the region behind the ear which is enervated by branches of the great auricular nerve and branches of the lesser occipital nerve. In an example, equivalent circuit 810*b* may be formed by electrode 804 and electrode 808 which are configured to stimulate tissue portion 822. In this example, tissue portion 822 may be positioned to target the region rostral to the ear under which the Auriculotemporal nerve transmits and gives out branches, as well as the region behind the ear which is enervated by branches of the great auricular nerve and branches of the lesser occipital nerve.

In an example, the tissue portion 820 can be the concha, the cybma concha, or a portion of both, which allows for ABVN stimulation and is stimulated at approximately 5 Hz or at 15 Hz, or at 30 Hz. In an example, the tissue portion 820 can be disposed in a region of the trigeminal nerve which is stimulated at approximately 80 Hz, or at 100 Hz or at 120 Hz or at 150 Hz.

In an example, equivalent circuit 810*a* is stimulated by a first channel and equivalent circuit 810*b* is stimulated by a second channel.

Turning to FIG. 8C and FIG. 8D, in some embodiments, stimulation may be provided transcutaneously using the electrodes 842*a*, 842*b*, and 842*c* of the auricular stimulation device 830. The electrodes 842*a*, 842*b*, and 842*c*, for example, may be configured to form corresponding circuits 850*a* and 850*b*.

In a first example, equivalent circuit 850*a* may be formed by electrode 842*b* and electrode 842*c* which are configured to stimulate tissue portion 852*a*. In this example, tissue portion 852*a* may be positioned to target the ATN in or around the area rostral to the auricle in proximity to the TMJ. For example, the equivalent circuit 850*a* may be designed to deliver stimulations to modulate activity in the VEF.

In a second example, equivalent circuit 850*b* may be formed by electrode 842*a* and electrode 842*c* which are configured to stimulate tissue portion 852*b*. In this example, tissue portion 852*b* may be positioned to modulate activity in the VEF by stimulating the AVBN in or around the McS.

In yet another example, to achieve a synergetic outcome, both the AVBN and the ATN are stimulated respectively in or around the McS and in or around the area rostral to the auricle in proximity to the TMJ. In this scenario, for example, both the AVBN and the ATN may be stimulated approximately at the same time in an interleaved manner. In illustration, each of electrodes 842*a* and 842*b* may be multiplexed with electrode 842*c* to form a circuit and forced current on to tissue 852*a* and tissue 852*b* in an alternating fashion. In another example, the AVBN and the ATN may be stimulated simultaneously.

In some embodiments, equivalent circuit 850*a* is stimulated by a first channel and equivalent circuit 850*b* is stimulated by a second channel.

Figure 8F:
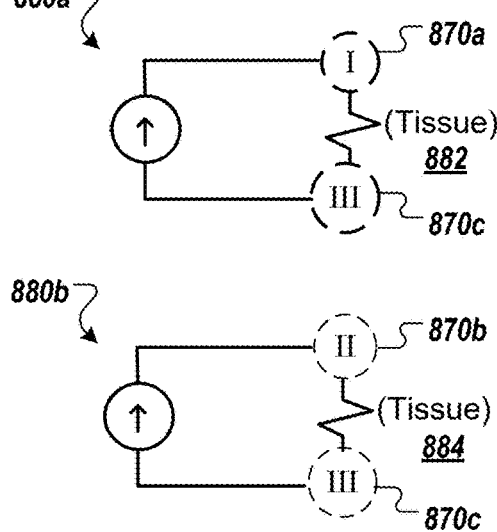

Turning to FIG. 8E and FIG. 8F, the auricular stimulation device 860 is shown having electrodes 870*a*, 870*b*, and 870*c*. The electrodes 870*a*, 870*b*, and 870*c*, for example, may be configured to form corresponding circuits 880*a* and 880*b* according to an example. In an example, equivalent circuit 880*a* may be formed by electrode 870*a* and electrode 870*c* which are configured to stimulate tissue portion 882. In this example, tissue portion 882 may be positioned to target the cymba conchae region which is enervated by branches of the auricular branch of the vagus nerve (e.g., positioned for stimulation by the first electrode 870*a*) and the region behind the ear (e.g., positioned for stimulation by the third electrode 870*c*) which is enervated by branches of the great auricular nerve and branches of the lesser occipital nerve. In a second example, equivalent circuit 880*b* may be formed by electrode 870*b* and electrode 870*c* which are configured to stimulate tissue portion 884. In this example, tissue portion 884 may be positioned to target the region rostral to the ear (e.g., positioned for stimulation by the second electrode 870*b*) which is enervated by the auriculotemporal nerve as well as the region behind the ear (e.g., positioned for stimulation by the third electrode 870*c*) which is enervated by branches of the great auricular nerve and branches of the lesser occipital nerve.

In some embodiments, the tissue portion 882 is a tissue region of the concha, the cymba concha, or a portion of both, which is stimulated at approximately 5 Hz or at 15 Hz, or at 30 Hz. In some embodiments, the tissue portion 884 is disposed in a region of the trigeminal nerve which is stimulated at approximately 80 Hz, or at 100 Hz or at 120 Hz or at 150 Hz.

In some embodiments, equivalent circuit 882 is stimulated by a first channel and equivalent circuit 884 is stimulated by a second channel. The first and second channels may be activated simultaneously and/or in an interleaved manner.

Example Hardware Systems

Figure 9:
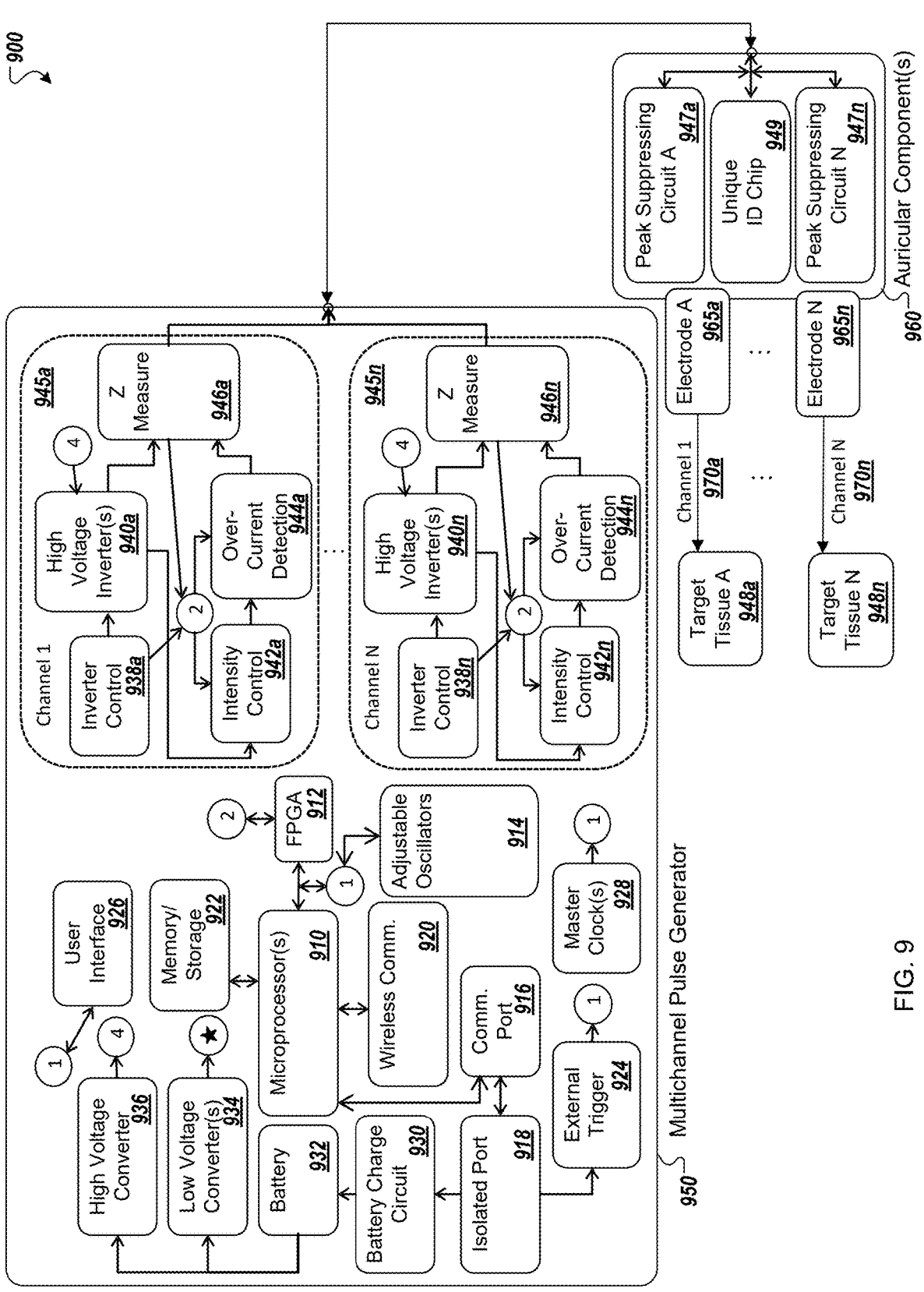
FIG. 9 is a block diagram of components of an example pulse generator in communication with an example auricular therapy device.

Turning to FIG. 9, a block diagram 900 of example components of a pulse generator 950 in communication with example components of an auricular component 960 is shown. The multichannel pulse generator circuit 950, in some embodiments, has at least one microcontroller or a microprocessor 910 with at least one core. When multiple microcontrollers or multiple cores are present, for example, one may control the wireless communication 920 and other core(s) may be dedicated to control the therapy. In some implementations, a low power programmable logic circuitry (e.g., field programmable gate array (FPGA) or programmable logic device (PLD)) 912 is also provided. For example, the microcontroller 910 may be configured to switch into a low power mode as frequently as possible while the programmable logic circuitry 912 controls therapy delivery.

In some embodiments, an inverter circuit 945*a-n* is used to generate biphasic/bipolar pulses. In some embodiments, one inverter circuit 945*a-n* is used per channel 970*a-n*, while in other embodiments, a single inverter circuit 945 is used for multiple channels 970*a-n*. Each channel 9*a-n*, for example, may target a different anatomical area (e.g., tissue region) 948*a-n*. A high voltage compliance (e.g., >50V, in other embodiments >70V, and yet in others >90V) may be used to ensure there is enough margin on the electrical potential to generate current demanded by the intensity control 942*a-n* of each inverter circuit 945*a-n* by providing one or more high voltage inverters 940*a-n* per inverter circuit 945*a-n*. In order to enhance safety, in some embodiments, an over current detection circuit 944*a-n* is provided in each inverter circuit 945*a-n*. In some embodiments, an impedance measuring circuit 946*a-n* is provided in each inverter circuit 945*a-n*. The impedance measuring circuit 946*a-n*, for example, may support tracking impedance over time to identify failure of sufficient therapy delivery. In some examples, therapy delivery may be compromised when the electrodes are not in contact or in good contact with the target tissue 948*a-n*, when a cable or connector between the multichannel pulse generator 950 is disconnected from one of the auricular component(s) 960, or where the electrodes have deteriorated or are defective. Monitoring impedance over time provides the added advantage that the condition of the contact electrode can be followed; thus allowing the controller to alert the user when the contact electrodes are close to their end of life or no longer viable. The FPGA 912 may control the inverter circuits 945*a-n* and receive feedback from an inverter control component 938*a-n*.

In some implementations, a battery 932 is used to power the pulse generator 950. The battery 932, for example, may power components of the pulse generator 950 and/or the auricular component(s) 960 via a one or more low voltage converters 934. Further, the pulse generator 950 may include a high voltage converter 936, coupled to one or more high voltage inverters 940*a*-940*n*, for delivery electrical stimulation therapy via the one or more channels 945*a-n*.

In some embodiments, an isolated port 918, such as a universal serial bus (USB) is used to charge the battery 932. In other embodiments, charging of the battery is accomplished wirelessly using induction coupling (not shown). The battery 932 may be charged via battery charge circuit 930.

In some implementations, the isolated port 918 is used to communicate with the microcontroller(s) 910 (e.g., via a communications port 916). The communication can be both ways, such that instructions or entire new code can be uploaded to the microcontroller(s) 910 and information stored in a memory 922 may be downloaded. In some embodiments, the memory 922 or additional memory can be added to the circuitry as an external component (e.g., in wireless or wired communication with the pulse generator 950). For example, the isolated port 918 (e.g., USB) may be used to connect memory to the pulse generator 950. In other embodiments, at least portions of the memory 922 may be internal to the microcontroller(s) 910. In some embodiments, the FPGA 912 may also have internal memory.

In some embodiments, an external trigger circuit 924 is included, such that the stimulation can be started and/or stopped via an external signal. In some embodiments, the external trigger signal can be passed through the isolated port 918; in yet other embodiments a modified USB configuration (i.e., not using the standard USB pin configuration) can be used to pass the trigger signal. Using a modified USB configuration will force a custom USB cable to be used, thus ensuring that an external trigger cannot be provided by mistake using an off-the-shelf USB cable. In a further example, the external trigger signal may be wirelessly transmitted (e.g., by Bluetooth) from a separate source.

In some embodiments, a hardware user interface is provided for interacting with the multichannel pulse generator 950 via user interface circuitry 926. In an example, the user interface circuitry 926 can include of buttons, LEDs, haptic (e.g., piezoelectric) devices such as buzzers, and/or a display, or a combination of any of them. In some embodiments, the user interface circuitry 926 includes signal processing components for interpreting user interface commands delivered via an external device (e.g., through the wireless communications 920). The external device, in some examples, may be a smart phone app, a tablet computer, or a medical monitoring device (e.g., in a hospital setting).

In some embodiments, an external master clock 928 is used to drive the microcontroller(s) 910 and/or the FPGA 912. In other embodiments the clock(s) of the components can be internal or integrated or co-packaged with the microcontroller(s) 910 and/or the FPGA 912. In some embodiments, one or more oscillators, including in some cases adjustable oscillators 914 are used to set pulse parameters such as, for example, frequency and/or pulse width.

In some embodiments, the auricular component 960 is made from a thin flex PCB or printed electronics, such that it is light weight and can be easily bent to accommodate different anatomies. In some embodiments, the auricular component 960 has more than one channel. The auricular component 960, or each channel thereof, may include a peak suppressing circuit 947*a-n* and electrodes 965*a-n* to contact the skin at the location of the target tissue 948*a-n*. In some embodiments, the auricular component(s) 960 includes a unique chip identifier or unique ID chip 949. The unique ID chip can be used to track usage as well as to prevent other non-authorized circuits from connecting to the multichannel pulse generator 950. At least one auricular component(s) 960 is connected to the multichannel pulse generator 950.

In some embodiments, the auricular component 960 is made from a thin flex PCB or printed electronics, such that it is light weight and can be easily bent to accommodate different anatomies. In some embodiments, the auricular component 960 has more than one channel. The auricular component 960, or each channel thereof, may include a peak suppressing circuit 947*a-n* and electrodes 965*a-n* to contact the skin at the location of the target tissue 948*a-n*. In some embodiments, the auricular component(s) 960 includes a unique chip identifier or unique ID chip 949. The unique ID chip can be used to track usage as well as to prevent other non-authorized circuits from connecting to the multichannel pulse generator 950. At least one auricular component(s) 960 is connected to the multichannel pulse generator 950.

In some embodiments, methods and systems of the present disclosure involve mechanical delivery of neurostimulation by one or more mechanical stimulation elements positioned on or implanted in a subject. In a first example, one or more target nerves, nerve plexuses, and/or ganglion may be stimulated by acoustic stimulation. The acoustic stimulation may be delivered by a transcutaneous ultrasonic device, such as a focused ultrasound (FUS) device, a peripheral focused ultrasound (pFUS) device, or a confocal ultrasound (CFU) device. In another embodiment, a small ultrasonic transducer can be implanted and wrap around a nerve using a cuff electrode. The one or more mechanical stimulation elements, for example, may be one or more acoustic transducers positioned against skin of a patient in proximity to one or more neural targets, such as it was previously discussed for electrostimulation of vagal and trigeminal branches (e.g., ABVN, ATN, etc.). Ultrasound can also be applied in a manner that stimulates an organ. For example, spleen activity can be increased via transcutaneous ultrasonic stimulation of the spleen. A percutaneous ultrasonic device may deliver acoustic stimulation, such as an ultrasound-powered piezoelectric neurostimulation device. In a second example, one or more target nerves, nerve plexuses, and/or ganglion may be stimulated by magnetic stimulation. The magnetic stimulation may be delivered by a non-invasive magnetic stimulator, such as a transcranial magnetic stimulation (TMS) device. An implanted magnetic stimulator, such as a micro-magnetic stimulation (μMS) device, may deliver the magnetic stimulation percutaneously. In a third example, one or more target nerves, nerve plexuses, and/or ganglion may be stimulated by vibrational stimulation. The vibrational stimulation may be delivered, for example, by an electromechanical vibrational stimulation device held against facial skin of a subject. The one or more mechanical stimulators may be one or more mechanical transducers configured to deliver vibrational neurostimulation therapy to one or more neural targets in proximity to the region of facial skin. Mechanical vibration may be applied to skin areas in close proximity to target nerves, such as described earlier for electrical stimulation (e.g., ABVN, ATN, etc.). Vibratory stimulation can be applied using a type of mechanical vibrator, such as a flat flexible piezoelectric sheet (e.g. the Kemet piezoelectric film haptic actuator by KEMET Corporation of Fort Lauderdale, FL) at frequencies ranging between 100 and 1000 Hz, and more preferably at frequencies between 300 and 600 Hz.

Figure 13:
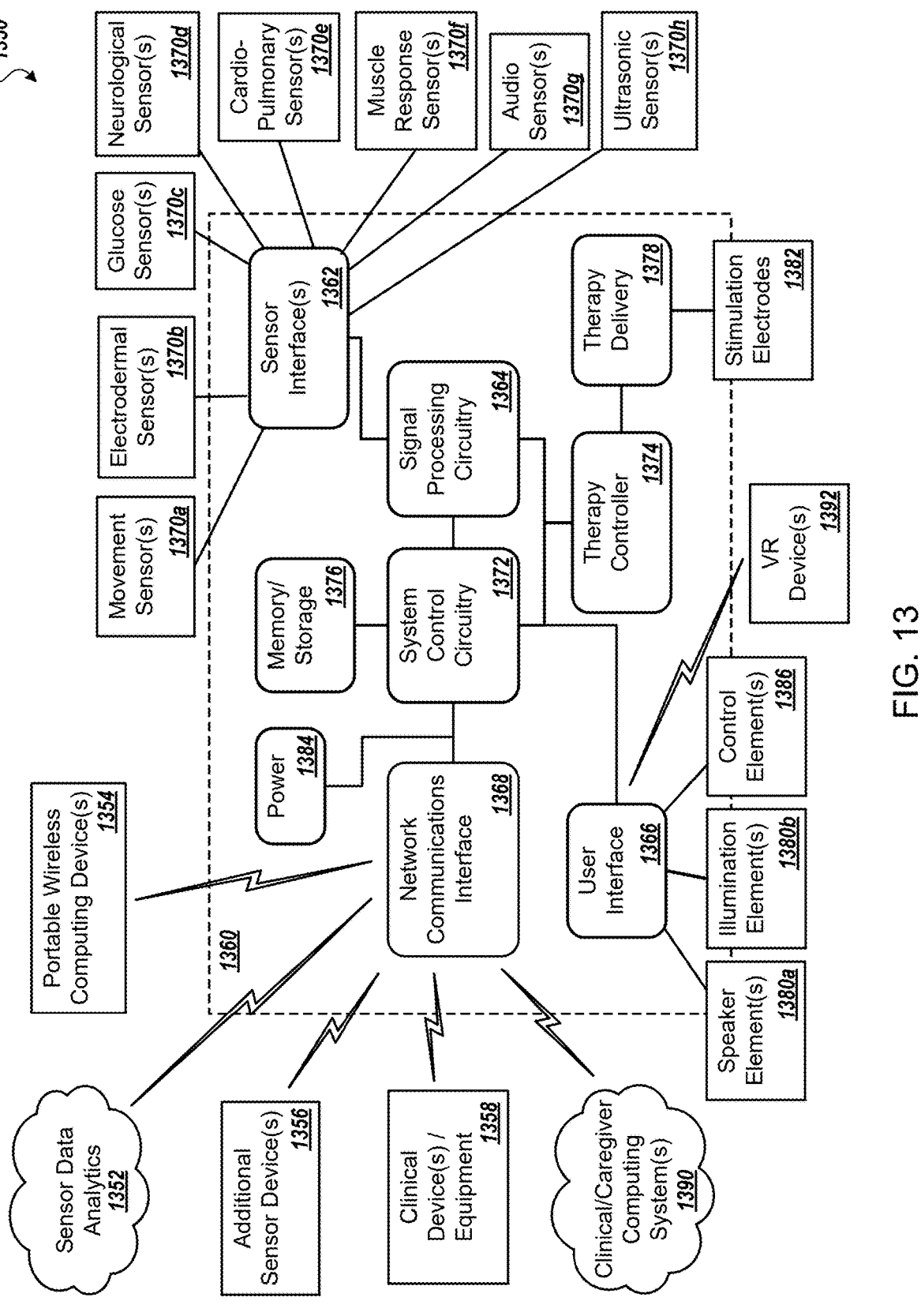
FIG. 13 illustrates an example system including a treatment device, sensor(s), and sensor signal conditioning and/or analysis circuitry.

In some embodiments, methods and systems of the present disclosure use feedback to monitor and/or modify the therapy. Turning to FIG. 13, an environment 1350 and system 1360 for using feedback in neurostimulation is illustrated. The environment 1350 and/or the system 1360 may incorporate elements of various treatment devices described herein. Further, the environment 1350 may include peripheral devices 1354, 1358, 1356, 1390 and/or a network system 1332. Additionally, the system 1360 may include aspects of a multichannel pulse generator, described in detail below. The environment 1350 and system 1360, for example, may be used to analyze sensor data in real-time, allowing for closed loop neurostimulation based on feedback data related to the wearer of a neurostimulation device. In another example, feedback monitoring can be used to alert the patient, a caregiver, and/or a clinical resource regarding therapy progress and/or a problem with the therapy. For example, a caregiver or clinician may be contacted, at clinical/caregiver computing system(s) 1390, in the event that therapy is not being adequately delivered and/or if the treatment device has been removed.

In some implementations, the system 1360 is activated at least in part by initiating delivery of power via power control circuitry 1384 to the system 1360. One or more control elements 1386, for example, may provide the ability for a wearer or patient to activate the system 1360 and/or to set initial therapeutic parameters. In certain embodiments, therapy may be remotely activated and/or adjusted through an external device, such as a portable computing device 1354.

In some implementations, one or more sensor interfaces 1362 of the system 1360 obtain feedback from one or more sensors 1370. Various sensors 1370, for example, may be provided for monitoring one or more symptoms being treated by the therapy, such as, in some examples, symptoms of stress and/or anxiety, pain, nausea, fatigue, inflammation, and/or disorientation/dizziness. In another example, certain sensors 1370 may be provided to monitor for activities or actions of the wearer to coordinate therapeutic stimulation with the activity/action. In some examples, the sensors 1370 may include one or more movement sensors 1370a (e.g., motion sensors, accelerometers, and/or gyroscopes) for monitoring movement activity (e.g., tremors, physiologic movement), one or more electrodermal sensors 1370b including, in some cases, electrochemical sensors for monitoring electrodermal activity (e.g., sweating, cortisol, etc.), one or more glucose sensors 1370c for monitoring glucose level, one or more neurological sensors 1370d for monitoring neurological activity (e.g., via electroencephalogram (EEG) sensing electrodes), one or more cardio-pulmonary sensors 1370e for monitoring cardio-pulmonary activity (e.g., electrocardiogram (EKG) sensing electrodes, heart rate sensor(s), blood pressure (systolic, diastolic and mean) sensor(s), etc.), and/or muscle response sensor(s) 1370f for monitoring muscle response activity (e.g., electromyography (EMG) sensors). The sensors 1370, in another example, may include one or more audio sensors 1370g (e.g., microphones, bone conduction microphones, vibrational sensors, etc.) for obtaining sound signals (e.g., verbalizations and/or utterances, breathing sounds, heart sounds, etc.). In an additional example, the sensors 1370 may include one or more ultrasonic sensors 1370h for measuring deep tissue signals such as, in some examples, central blood pressure, cerebral blood flow velocity (CBFV), heart rate, and/or cardiac output.

Skin conductance (SC), also known as electrodermal activity (EDA), provides a direct and reliable measure of sympathetic nervous system activity, as sweat gland activity is exclusively controlled by sympathetic innervation. Under controlled environmental conditions (temperature 20-25° C., humidity 45-55%), normal tonic (baseline) SC values typically range from 2-20 microsiemens (μS), with common baseline readings between 5-10 μS. In this context, the terms "tonic" and "phasic" refer to a state of sympathetic activity; with tonic measurements reflecting the current general sympathetic arousal tone, and phasic referring to a rapid change in SC responses reflecting acute sympathetic activation.

Table 6, below, illustrates normal ranges for various SC measurements. Both tonic (baseline) and phasic (response) SC measurements can be effectively monitored using modern wearable sensors, providing continuous assessment of sympathetic activation. SC measurements can be obtained using various devices, from research-grade systems to wearable sensors. Research-grade options include dedicated psychophysiology systems (e.g., Biopac GSR 100C, ADInstruments GSR Amp) and specialized EDA monitors (e.g., ProComp by Thought Technology Ltd. of Montreal, Canada). Consumer and clinical wearable options include the E4 wristband by Empatica Inc. of Boston, MA, Shimmer3 GSR+ Unit by Shimmer Wearable Sensor Technology of Dublin, IE, and various emerging wearable devices designed for continuous SC monitoring.

TABLE 6

| Electrodermal Activity Measurements Electrodermal Activity | | |
| --- | --- | --- |
| Skin Conductance | Normal Range | Units |
| Tonic SC (Adults) | 2-20 | µS |
| Tonic SC (Children 5-10) | 5-25 | µS |
| Tonic SC (Adolescents 11-17) | 3-22 | µS |
| Tonic SC (Elderly 60+) | 1-15 | µS |
| Baseline SC (typical) | 5-10 | µS |
| Phasic Response Amplitude | 0.1-1.0 | µS |
| Phasic Response Frequency | 1-3 | responses/minute |
| Response Latency | 1-3 | seconds |
| Recovery Time | 2-10 | seconds |

The sensors 1370 may be in wired and/or wireless communication with the sensor interface(s) 1362 of the system 1360. Certain sensors 1370, for example, may be integrated into the earpiece and/or concha apparatus of an ear-mounted neurostimulation devices such as various devices described in the present disclosure. One or more sensors 1370, in another example, may be integrated into a pulse generator for neurostimulation therapy delivery. Further to the example, periodic monitoring may be achieved through prompting the wearer to touch one or more electrodes on the system 1360 (e.g., electrodes built into a surface of the pulse generator) or otherwise interact with a component of the system 1360 such as the pulse generator (e.g., hold the pulse generator extended away from the body to monitor tremors using a motion detector in the pulse generator). The prompting, for example, may be supplied via a user interface 1366 by one or more speaker elements 1380a (e.g., a verbal command) and/or one or more illumination element(s) 1380b (e.g., an LCD display, LED display, 7-segment digital display, and/or LED indicator(s) next to printed information on a surface of the system 1360).

In some implementations, the user interface 1366 is used to deliver a portion of the therapy to the wearer. For example, the system 1360 may coordinate neurostimulation therapy with a Virtual Reality (VR) device 1392. The VR device 1392, in some examples, may deliver audio, visual, and/or haptic output coinciding with the goals of a particular therapy. In example, to reduce stress and anxiety, the system may configure the VR device 1392 to provide relaxing audio and/or visual output to the wearer during neurostimulation therapy. In another example, to overcome PTSD, phobias, cravings, and/or other addiction-related triggers, the VR device 1392 may be configured to present triggering audio and/or visual content during neurostimulation therapy. Although illustrated as being a separate VR device 1392, in other embodiments, neurostimulation electrodes are built into the VR device (e.g., a VR headset) as a virtual reality-enabled neurostimulation therapy device.

In some implementations, feedback data gathered by the system 1360, such as sensor feedback, may be supplied by a pulse generator to one or more of the peripheral devices 1354, 1390. The feedback, for example, may include sensor signals related to symptoms of the patient being treated by the system 1360. A clinical user monitoring sensor metrics related to these signals may manually adjust the delivery of therapy accordingly using the one or more adjustable controls provided by the application. Further, in some implementations, the feedback may be used by one of the peripheral devices 1354, 1390 to generate a notification for review by the patient, a caregiver, or a clinician. The notification, for example, may include a low power notification, a device removed notification, or a malfunction notification. In an illustrative example, the system 1360 may monitor impedance measurements allowing closed loop neurostimulation. The notifications regarding removal or malfunction, for example, may be issued upon determining that the impedance measurements are indicative of lack of a proper contact between one or more electrodes of the treatment device and tissue on or surrounding the patient's ear. The notifications, for example, may be delivered to the patient and/or one or more third parties via an application executing on one of the peripheral devices 1354, 1390. For example, the application may issue an audible alarm, present a visual notification, or generate a haptic output on the peripheral device 1354, 1390. Further, in some embodiments, the application may issue a notification via a communication means, such as sending an email, text message, or other electronic message to one or more authorized users, such as a patient, caregiver, and/or clinician.

Conversely, in some implementations, a cloud platform having sensor data analytics 1352 accessible via the network may receive the feedback, review present metrics, and relay instructions to the pulse generator (e.g., via a Wi-Fi network or indirectly via a local portable device 1354). The pulse generator, in a further example, may gather feedback from one or more fitness monitor and/or health monitor devices 1354, 1390, analyze the feedback, and determine whether to adjust treatment accordingly.

In other implementations, the pulse generator is included in the auricular component of a treatment device; that is, the pulse generator and auricular component may be co-located such that the need for an extension cable to connect them is not necessary. The auricular component and pulse generator may be wirelessly connected to an electronic device (for example a personal computer, a tablet or a phone) 1354, 1390 and/or to a remote server 1352. In turn, in some embodiments, the electronic device 1354, 1390 is also wirelessly connected to the remote server 1352.

In some implementations, the system 1360 includes at least one isolated port for wired communication with the peripheral device(s) 1354, 1390. The isolated port, in some examples, may be a universal serial bus (USB) connection (e.g., a mini-USB connection, a micro-USB connection, a USB-C port, etc.), an Ethernet port, or a Serial ATA (SATA) connector. The isolated port, for example, may be included in the pulse generator for updating a software version running on the pulse generator or for reprogramming treatment settings of the pulse generator. The isolated port(s) may be connected to the network communications interface 1368 for enabling communications between a peripheral device 1354, 1390 and the system 1360 via the isolated port. The network communications interface 1368 may couple the isolated port to the system control circuitry 1372. For example, the network communications interface 1368 may establish a direct (e.g., wired) communication link with one of the peripheral device(s) 1354, 1390 to transfer data from a memory 1376 to the peripheral device 1354, 1390.

Further, a wireless radio frequency (RF) antenna (e.g., transmitter or transmitter/receiver), in some implementations, is included in the network communications interface 1368. The RF antenna can be in wireless communication with the peripheral device(s) 1354, 1358 directly or via the network. The RF antenna, in combination with processing circuitry for generating wireless communications may function as a broadcast antenna, providing information to any RF receiver in a receiving region of the system 1360. For example, the RF antenna may broadcast sensor data, sensor metrics, alerts, alarms, or other operating information for receipt by one or more peripheral devices 1354, 1390. In other implementations, the RF antenna, in combination with additional processing circuitry, may establish a wireless communication link with a particular peripheral device 1354, 1390. The wireless communication link, in some embodiments, is a secure wireless communication link (e.g., HIPAA-compliant) for sharing patient data with the peripheral device(s) 1354, 1390. The wireless communication link may be used to receive control settings from a peripheral device 1354, 1390 for controlling the functionality of the pulse generator, for example.

In some implementations, sensor data is received via a network communications interface 1368 from the one or more portable wireless computing devices 1354. In some examples, sensor elements of a common smart phone, smart glasses, smart rings, and/or smart watch (e.g., accelerometer, gyroscope, microphone, image sensor (e.g., cameras), heart rate monitor, oxygen saturation, blood pressure, glucose sensor, etc.) may be used by an application designed to interoperate with the system 1360 to supply sensor data to the system 1360. In illustration, imaging (e.g., video) of pupillary changes (e.g., pupillary dilation) may be captured by a smart phone or smart glasses and used by the system 1360 as feedback for making therapy adjustments. The pupillometry measurements, for example, can be used as a measure of attention, alertness, or wakefulness (or the lack thereof). Thus, the feedback may be used to adjust therapy to maintain a desired level of attention, alertness, and/or wakefulness.

In some implementations, sensor data is received via the network communications interface 1368 from one or more additional sensor devices 1356. The additional sensor devices 1356, in some examples, can include fitness monitors and/or activity trackers (e.g., for providing data similar to that collected by the movement sensor(s) 1370a, the electrodermal sensor(s) 1370b, and/or the cardio-pulmonary sensor(s) 1370e), home health monitoring devices (e.g., digital smart blood pressure cuffs for providing data similar to that collected by the cardio-pulmonary sensor(s) 1370e, digital smart thermometers, etc.), and/or remote patient monitoring devices (e.g., glucometer for providing data similar to that collected by the glucose sensor(s) 1370c, pulse oximeter, wearable heart monitors such as a Holter monitor for providing data similar to that collected by the cardio-pulmonary sensor(s) 1370e, etc.).

Sensor data, in some implementations, is received via the network communications interface 1368 from one or more clinical devices and/or equipment 1358. In illustration, imaging techniques such as magnetic resonance imaging (MRI) and/or functional MRI (fMRI) could be used to adjust the therapy in a clinical setting for a given user. In other examples, data similar to that collected by the neurological sensor(s) 1370d, cardio-pulmonary sensor(s) 1370e, glucose sensor(s) 1370c, and/or muscle response sensor(s) 1370f may be provided by various clinical equipment 1358.

In some embodiments, the type of monitoring used by the system 1360 and/or reliance on (e.g., trust in) various incoming sensor data may be based, in part, on a treatment setting. For example, neurological data captured by sensors such as the neurological sensor(s) 1370d may be easier to capture in a hospital setting, while certain cardio-pulmonary data captured by sensors such as the cardio-pulmonary sensor(s) 1370e (e.g., heart rate monitoring) may be achieved by capturing signals from a pulse oximeter and/or heart rate monitor built into the earpiece or another sensor (e.g., additional sensor devices 1356) built into a low budget health monitoring device such as a fitness monitoring device or smart watch.

In some implementations, the sensor interface(s) 1362 collects signals from the sensor(s) 1370 and provides the signals to signal processing circuitry 1364. The signal processing circuitry 1364, for example, may include one or more filters (e.g., a bandpass filter), amplifiers, and/or other circuitry to remove noise, isolate valid incoming signals, and/or increase signal strength. In some embodiments, the signal processing circuitry 1364 converts an analog signal to digital signal components.

In some implementations, sensor signals from the sensors 1370, portable wireless computing device(s) 1354, additional sensor device(s) 1356 and/or clinical device(s)/equipment 1358 are provided to system control circuitry 1372 for data analysis. The system control circuitry 1372, in some examples, may perform thresholding, pattern analysis, and/or variation over time analysis to recognize physiological, biological, and/or physical behaviors of a wearer of the therapeutic stimulation device corresponding to adjustments in treatment. For example, sensor data may be collected in a memory or temporary data storage region 1376 for analyzing sensor data over a predetermined period of time. The period of time may differ, in some examples, based on the type of therapy provided, the type of data analyzed, and/or the therapeutic goal. The adjustments in treatment, in some examples, can include initiating treatment, ceasing treatment, and/or adjusting one or more treatment parameters (e.g., voltage, frequency, stimulation pattern, stimulation location(s), etc.).

In some implementations, the system control circuitry 1372 provides sensor data to an external sensor data analytics system 1352 via the network communications interface 1368. The sensor data analytics system 1352, in some examples, can include an edge router, a cloud computing platform, and/or one or more networked servers configured to analyze sensor data to identify circumstances that trigger an adjustment in treatment. The analysis, in some embodiments, involves biometric fingerprint analysis where the physiological, biological, and/or physical behaviors captured in the sensor data are analyzed in view of baseline or historic physiological, biological, and/or physical behaviors of the particular wearer.

In some implementations, based on analysis of the sensor data by the system control circuitry 1372 and/or the sensor data analytics system 1352, therapy parameter adjustments are provided to a therapy controller 1374 for adjusting stimulation parameters delivered via therapy delivery circuitry 1378 (e.g., pulse generator circuitry) to a set of stimulation electrodes 1382. Therapy delivery circuitry 1378 and stimulation electrodes 1382 are discussed in greater detail above with reference to FIG. 9.

In a first illustrative example, upon reduction or removal of one or more symptoms, a therapeutic output may be similarly reduced or ceased. Conversely, upon increase or addition of one or more symptoms, the therapeutic output may be similarly activated or adjusted (increased, expanded upon, etc.).

In another illustrative example, feedback related to electrodermal activity could be used to monitor and detect the speed or timing of a symptom and/or therapeutic outcome. In an example, the electrodermal activity could be sensed by electrodermal sensors 1370b. For example, an electrodermal patch with one or more electrodermal sensors 1370b can be used to estimate the individual's stress levels by assessing cortisol levels in sweat.

In an example, the one or more movement detectors 1370a may be configured to detect a tremor and/or physiologic movement. In an aspect, the tremor and/or the physiologic movement can be indicative of the underlying condition and/or the treatment to the underlying condition. In an example, the tremor and/or physiologic movement can be indicative of symptoms associated with substance withdrawal. In another example, movement and movement serial combinations can be used to assess the outcome of a training protocol aimed at restoring performance of these movements.

In a further example, feedback from glucose sensors 1370c can be used to modulate the therapy. People suffering from diabetes 2 lack the ability to control glucose levels, and vagal stimulation has been shown to decrease hyperglycemia. Therefore, assessing glucose levels can be used to trigger stimulation to increase glycemic control.

In an additional example, neurological sensor(s) 1370d and/or cardio-pulmonary sensors 1370e may be used to assess heart rate and heart rate variability (HRV) and/or electrodermal activity, to determine the activity of the autonomic nervous system in general and/or the relative activity of the sympathetic and parasympathetic branches of the autonomic nervous system (e.g., the P/S ratio), and to modulate the therapy. Autonomic nervous activity can be indicative of symptoms associated with substance withdrawal. In an aspect, the treatment device can be used to provide therapy for treating cardiac conditions such as atrial fibrillation and heart failure. In an example, therapy can be provided for modulation of the autonomic nervous system. In some implementations, the treatment device can be used to provide therapy to balance a ratio between any combinations of the autonomic nervous system, the parasympathetic nervous system, and the sympathetic nervous system.

Heart Rate Variability (HRV) analysis is a well-established method for assessing autonomic nervous system function through measurement of variations in consecutive heartbeat intervals. Both time and frequency domain methods provide valuable information about autonomic regulation. Frequency domain measurements include Low Frequency (LF: 0.04-0.15 Hz) with normal values of 500-2000 $ms^2$, High Frequency (HF: 0.15-0.40 Hz) ranging from 100-900 $ms^2$, and their ratio (LF/HF) typically falling between 1.5-2.0. Additional frequency domain parameters include normalized units for both LF and HF (30-65 n.u.) and Very Low Frequency (VLF: 5-50 $ms^2$), with total power typically ranging from 1000-3000 $ms^2$. Time domain measurements include several well-documented parameters: the Standard Deviation of Normal-to-Normal intervals (SDNN) typically ranges from 141±39 ms, the Standard Deviation of 5-minute NN interval means (SDANN) averages 127±35 ms, and the percentage of successive RR intervals that differ by more than 50 ms (pNN50) normally falls between 3-30%. Table 7, below, provides HRV measurements and associated ranges.

While both domains provide valuable information, time domain measurements are particularly suited for wearable, dynamic applications. They require less computational power, provide immediate results, and are more robust to movement artifacts and missing data-all critical factors in wearable applications. Among time domain measures, RMSSD (Root Mean Square of Successive Differences) offers distinct advantages: it specifically reflects parasympathetic activity, provides reliable results in short-term recordings, requires minimal processing delay, and maintains accuracy during varying respiratory patterns.

HRV measurements can be obtained using various commercially available devices, ranging from medical-grade ECG systems to consumer devices. Medical-grade options include Holter monitors and dedicated HRV analysis systems (e.g., MP160 by Biopac Systems Inc. of Goleta, CA, PowerLab by ADInstruments of Sydney, Australia). Consumer-grade devices include chest straps (e.g., Polar H10 Heart Rate Monitor by Polar Electro Oy of Kempele, Finland), smartwatches (e.g., Apple Watch by Apple Inc. of Cupertino, CA, Garmin smartwatches by Garmin Ltd. of Schaffhausen, Switzerland), and specialized HRV monitors (e.g., Elite HRV of Gloucester, MA, Oura Ring by Oura Health Ltd. of Oulu, Finland).

In some embodiments, physiological signals are used as feedback to start and stop treatment based on autonomic nervous system functionality assessment (e.g., P/S ratio assessment) using sensor measurements. When using HRV alone, RMSSD thresholds may be employed. Table 8, below, illustrates example initiation and termination thresholds using RMSSD measurements. In an illustrative example, therapy may be initiated when the subject's RMSSD value measures below age-specific thresholds (e.g., <20 ms for young adults). Further to the example, a therapeutic session (e.g., five or more minutes of neurostimulation therapy delivery) and/or a therapeutic period (e.g., number of sessions, number of days each including one or more sessions) may be terminated when the subject's RMSSD measurement exceeds a specified threshold (e.g., >30 ms). To ensure a stable measurement, in some implementations, a therapeutic session or therapeutic period may be terminated upon establishing consistency across multiple RMSSD measurements, such as determining that at least two out of three measurements taken within consecutive 5-minute periods are each exceeding the specified threshold.

When using skin conductance measurements alone to assess autonomic nervous system functionality, tonic SC thresholds may be applied. Table 9, below, illustrates example initiation and termination thresholds using SC measurements. In an example, neurostimulation therapy may be initiated when a subject's tonic SC measurement exceeds a set threshold (e.g., 25 μS) or rises more than 50% above a baseline measurement. Further to the example, a therapeutic session and/or a therapeutic period (e.g., number of sessions, number of days each including one or more sessions) may be terminated upon determining that the tonic SC measurement has returned to within 20% of the baseline measurement and/or drops below a threshold. To ensure a stable measurement, in some implementations, a therapeutic session or therapeutic period may be terminated upon establishing consistency across multiple tonic SC measurements, such as determining that at least two out of three measurements taken within consecutive 5-minute periods are each below the threshold and/or within 20% of the baseline measurement.

In some embodiments, a combination of HRV and SC measurements are used to assess autonomic nervous system functionality. Table 10 and Table 11, below, provide illustrative examples for using a combination of HRV and SC measurements in initiating and terminating treatment. In an illustrative example, therapy may be initiated when a tonic SC measurement exceeds an SC threshold (e.g., 25 μS) and terminated when both RMSSD exceeds an RMSSD threshold (e.g., 30 ms) and SC returns to within 20% of the baseline. In another illustrative example, therapy may be initiated when the value of at least one tonic SC measurement rises more than 50% above a subject's baseline tonic SC value, with termination requiring either RMSSD to exceed a threshold (e.g., 30 ms) or SC to return to within 10% of baseline in two out of three consecutive 5-minute periods.

In yet another embodiment, SC might be used for therapy initiation (e.g., applying a threshold >25 µS), while the combination of both measures (e.g., RMSSD>30 ms AND SC within 20% of baseline) would be required for termination. This approach leverages the rapid response of SC for initiation while ensuring more robust evidence of autonomic rebalancing before termination.

The various combinations of HRV and SC measurements illustrated in the examples described above provide complementary information about both parasympathetic and sympathetic activation. Specific thresholds and combinations may be established, in some examples, based on individual patient characteristics (e.g., see values corresponding to age ranges in Table 7 through Table 9, below), type(s) of sensor(s) and/or wearable monitoring device(s) being used, and/or clinical requirements. The HRV and/or SC sensors, for example, may be included within a wearable neurostimulation system and/or sensor data may be acquired from one or more additional devices having the sensor(s).

TABLE 7

| HRV Measurements | | |
| --- | --- | --- |
| Measurement | Normal Range | Units |
| RMSSD (Young Adults) | 27-75 | ms |
| RMSSD (Children 5-10) | 50-140 | ms |
| RMSSD (Adolescents 11-17) | 40-120 | ms |
| RMSSD (Middle Age 40-59) | 20-60 | ms |
| RMSSD (Elderly 60+) | 15-45 | ms |
| SDNN (24-hour) | 141 ± 39 | ms |
| SDANN | 127 ± 35 | ms |
| pNN50 | 3-30 | % |
| LF Power | 500-2000 | $ms^2$ |
| HF Power | 100-900 | $ms^2$ |
| LF/HF Ratio | 1.5-2.0 | ratio |

TABLE 8

| Treatment Thresholds: HRV (RMSSD) Treatment Thresholds-HRV (RMSSD) | | | |
| --- | --- | --- | --- |
| Population | Start Therapy Threshold (e.g., from a single 5-minutes measurement) | Stop Therapy Threshold (e.g., from two out of three consecutive 5 minutes measurement) | Units |
| Young Adults (18-39) | <20 | >30 | ms |
| Middle Age (40-59) | <15 | >25 | ms |
| Elderly (60+) | <12 | >20 | ms |
| Children (5-10) | <40 | >50 | ms |
| Adolescents (11-17) | <35 | >45 | ms |

TABLE 9

| Treatment Thresholds: SC Treatment Thresholds-SC | | | |
| --- | --- | --- | --- |
| Variable | Start Therapy | Stop Therapy | Units |
| Absolute Value | >25 | within 20% of baseline | µS |
| Relative Change | >50% above baseline | within 20% of baseline | % change |
| Phasic Response Frequency | >5 | <3 | responses/minute |
| Phasic Response Amplitude | >1.5 | <1.0 | µS |

TABLE 10

| Example 1: Treatment Initiation and Termination Parameters Combined Thresholds Example 1 | | | |
| --- | --- | --- | --- |
| Technique | Start | Stop | Units |
| SC | >25 | within 20% of baseline | µS |
| RMSSD | not used | >30 | ms |

TABLE 11

| Example 2: Treatment Initiation and Termination Parameters Combined Thresholds Example 2 | | | |
| --- | --- | --- | --- |
| Technique | Start | Stop | Units |
| SC | >50% above baseline | within 10% of baseline | % change |
| RMSSD | not used | >30 | ms |

In a further illustrative example, feedback signals collected by the muscle response sensor(s) 1370f may be analyzed to trigger stimulation during physical movement recovery, such as arm movement recovery. For arm movement recovery, multiple muscle response sensors 1370f can be arranged in a sleeve such as the NeuroLife® EMG Sleeve provided by Battelle Memorial Institute of Norwell, Massachusetts.

In a final illustrative example, attention, alertness, and/or wakefulness can be assessed by the ultrasonic sensor(s) 1370h by measuring cerebral blood flow velocity (CBFV). In such an example, CBFV can be used as feedback to adjust therapy.

In some implementations, the sensor data analytics system 1352 collects historic sensor data and treatment parameters across a population of patients and applies the collected data to performing machine learning analysis to refine therapeutic protocols and parameters at an individual level. This, for example, can lead to faster and/or a higher function recovery. Following a stroke or a TBI, in an illustrative example that may be used in a hospital setting, such as in the Intensive Care Unit (ICU) or the Neonatal Intensive Care Unit (NICU), data collected via sensors 1370 such as, in some examples, heart rate (ECG), arterial oxygen saturation (SpO2), arterial blood pressure (in some cases using an arterial catheter), central venous pressure, core temperature, blood glucose level, breathing rate and/or volume, urine output, ANS activity and/or P/S ratio (e.g., using HRV and/or electrodermal activity), and/or cardiac sensor(s) output, may be analyzed and applied in automatically directing and/or adjusting neuromodulatory treatment. In further examples, the sensor data may provide insight regarding osmolarity, serum electrolytes, and/or blood gases (arterial) that, in turn, could assist in making determinations when automatically directing and/or adjusting the neuromodulatory treatment. The sensor data, in some examples, may be analyzed for evidence of a comfort level of the patient (e.g., indicators of potential pain and/or stress in the patient), evidence of inflammation, and/or evidence of ischemic processes (e.g., evidence of build-up of metabolic waste).

Figure 14:
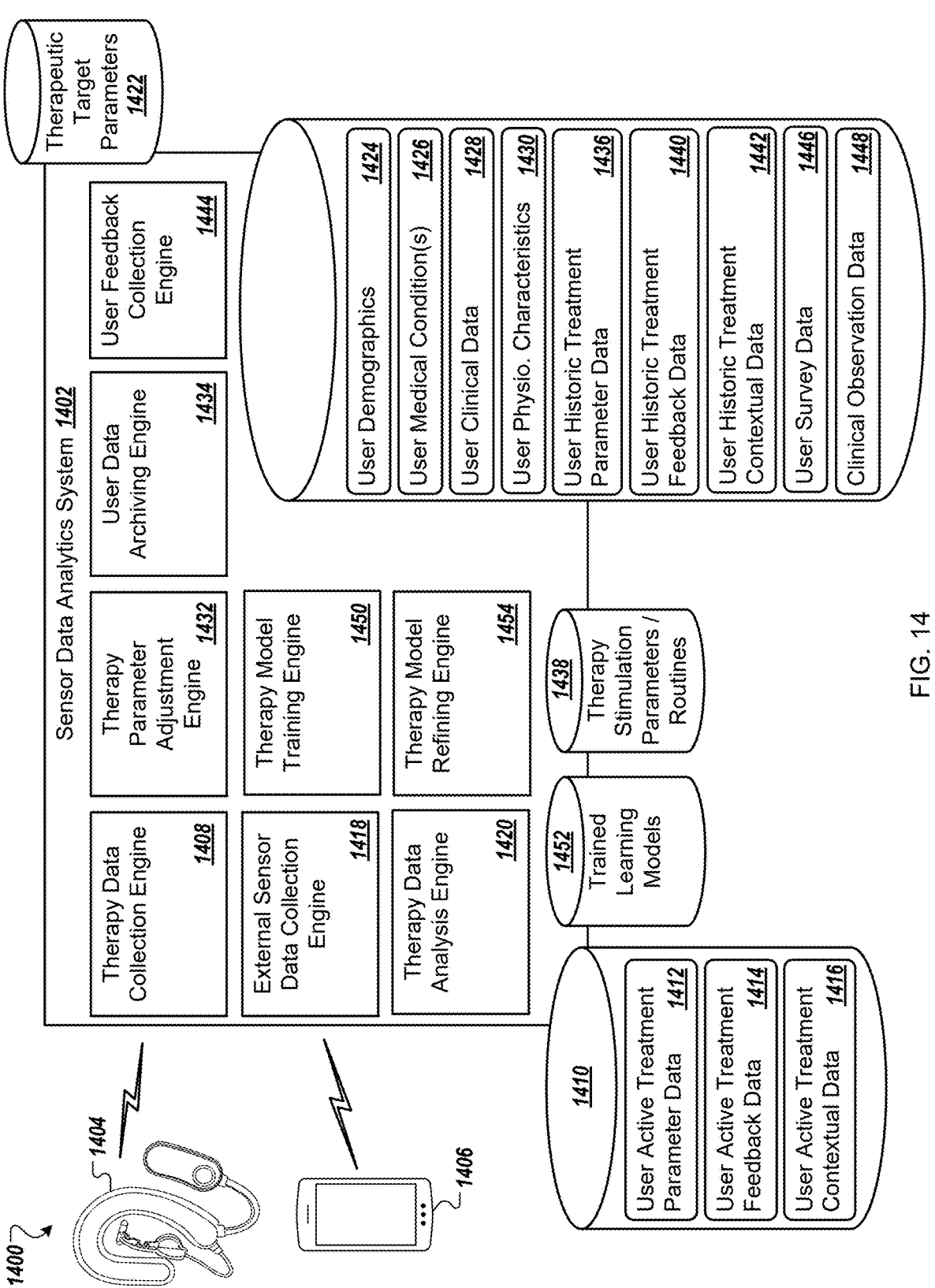
FIG. 14 is a block diagram of an example sensor data analytics system for delivering neurostimulation therapy that is customized to the wearer.

In some implementations, the sensor data analytics system 1352 applies machine learning and/or artificial intelligence (AI) analysis to refine therapy sessions to deliver more efficacious and/or more efficient treatment. Turning to FIG. 14, an example sensor data analytics system 1402 and platform environment 1400 obtains data from neurostimulation systems (e.g., devices and/or pulse generators) 1404 and/or computing devices 1406 and analyzes the data to confirm therapeutic goals are being met and/or to automatically refine therapeutic parameters to improve on the effectiveness of the present therapy.

In some embodiments, the sensor data analytics system 1352 includes a therapy data collection engine 1408 configured to collect data from the neurostimulation systems 1404 and associate the data with individual users. The therapy data collection engine 1408, in some examples, may collect, in relation to each user of each neurostimulation system 1404 and store the data to a computer-readable data storage region (user data store) 1410. The user data, in some examples, can include active treatment parameter data 1412 (e.g., stimulation pattern(s), frequenc(ies), identification of a particular therapeutic routine, identification of a particular therapeutic setting, etc.), active treatment feedback data 1414 (e.g., sensor data collected by the neurostimulation system 1404 and/or one or more other sensor devices in communication with the neurostimulation system 1404), and/or active treatment contextual data 1416 (e.g., geographic location, time of day, day of week, ambient temperature, velocity/acceleration of wearer, ambient noise level, etc.).

In some implementations, an external sensor data collection engine 1418 collects sensor data obtained by one or more devices external to the neurostimulation systems 1404 and in communication with the sensor data analytics system 1402. The devices, in some examples, can include fitness-monitoring devices (e.g., Fitbit, Apple Watch, or Garmin Smartwatch) and/or health-monitoring devices (e.g., a glucose meter, a holter monitor, an electrocardiogram (EKG) monitor, or an electroencephalogram (EEG) monitor). In further examples, the external devices may include clinical patient monitoring and/or management devices (e.g., brain monitoring, capnography monitoring, cerebral/somatic oximetry, pulse oximetry, localized and/or corporeal temperature management, etc.).

In an illustrative example, the external sensor data collection engine 1418 may collect menstrual cycle data from a fitness-monitoring device. The menstrual cycle data, for example, may be inputted by the wearer and/or derived by the fitness-monitoring device based on historic cycle patterns and/or biological patterns (e.g., changes in body temperature, changes in sleep patterns, etc.) of the wearer. The menstrual cycle data may be used to prompt the subject to begin stimulation treatment (e.g., anticipating onset of PMS).

In another example, the external sensor data collection engine 1418 may collect body temperature data and/or sweat gland activity data (e.g., galvanic skin response (GSR) sensor data) to identify hot flashes. The data for identifying hot flashes, for example, may be used to trigger therapy and/or to propose a stimulation regimen appropriate to the subject based on historic data trends.

In some implementations, a therapy data analysis engine 1420 analyzes the user data stored to the user data store 1410 to gauge efficacy of ongoing and/or recently completed therapy. Evidence of efficacy, for example, may be based on a set of therapeutic target parameters 1422 associated with a given therapy. The therapy data analysis engine 1420, for example, may compare the user active treatment feedback data 1414 to threshold values and/or target ranges of values. In another example, the therapy data analysis engine 1420 may compare a duration of each symptom, as evidenced through sensor data, to a threshold duration prior to reduction or cessation of symptom. In some embodiments, the therapeutic target parameters 1422 may be clinician-adjustable such that a clinician may customize the target parameters based on a particular patient. In certain embodiments, different sets of therapeutic target parameters 1422 are provided based on, in some examples, user demographics 1424 (e.g., age, gender, etc.), user medical conditions 1426 (e.g., diagnosed diseases and/or disorders), and/or user clinical data 1428 (e.g., weight, body mass index (BMI), smoking status, drug use status, pregnancy status, etc.). In further embodiments, the therapeutic target parameters 1422 are adjusted based on user physiological characteristics 1430 (e.g., baselines or typical physiological patterns exhibited by the particular wearer).

In some implementations, the therapy analysis engine 1420, based on a difference between the therapeutic target parameters 1422 and the user active treatment feedback data 1414, provides parameter deltas and/or other feedback information to a therapy parameter adjustment engine 1432 to determine a set of adjusted treatment parameters. The set of adjusted treatment parameters may include one or more device settings (e.g., frequenc (ies), pattern(s), repetition(s), etc.). In one illustration involving repeated rehabilitation exercises, the stimulation duration may be systematically varied such that, using movement sensors (including for example, triaxial accelerometers and/or gyroscopes), a rate of improvement versus stimulation duration following triggering can be established. The steps for varying stimulation, for example, may be stored as therapy stimulation parameters and/or routines 1438. Stimulation duration may be automatically adjusted in order to increase the success rate and/or accelerate the recovery of a particular function.

In the example illustration of motor skill recovery training for a stroke patient, based at least in part on the user active treatment feedback data 1414 corresponding to a current activity or rehabilitative exercise, the therapy parameter adjustment engine 1432 may determine a next therapeutic routine and/or stimulation parameters. For example, upon sufficiency of performance of a current task, the therapy parameter adjustment engine 1432 may provide the neurostimulation system 1404 with instructions for a next task. The next task, in some examples, may be more challenging, exercise a different muscle group, and/or focus on linking learned skills into a series performance. The next task may be selected, for example, from a hierarchy or series of tasks stored as part of the therapy stimulation parameters and/or routines 1438.

In some embodiments, the therapy stimulation parameters and/or routines 1438 include one or more priming routines to be applied to a wearer of the neurostimulation systems 1404 prior to beginning therapeutic stimulation, such as a motor skills training session or PTSD recovery session. In illustration, neurostimulation for priming, or preparing cognitive pathways for a therapeutic/training session, may begin at least 1 minute, between 1 minute and 10 minutes, up to 30 minutes, and/or within an hour or so of the therapeutic training session. In another example, a priming routine may be introduced into the middle of a larger therapy routine involving multiple stages or phases of treatment. In a first illustration, therapeutic stimulation may be paired with an activity in a first training phase to, for example, develop new pathways to recover specific functions. In a second, priming, phase, priming stimulation may be used for general cognition boosting, for example while performing a motor skill routine that encompasses multiple functions (e.g., a combination of multiple movements/tasks). In a second illustration, therapeutic stimulation may be paired with exposure to stimulating input (e.g., aural, visual, and/or haptic, etc.) in a first training phase to, for example, overcome adverse reactions. In a second, priming, phase, priming stimulation may be used for general emotional well-being enhancement, for example while taking a break between stimulating input exposure.

In some implementations, the sensor data analytics system 1402 provides the adjusted treatment parameters to the corresponding neurostimulation system 1404, directly or via another computing device 1406. A user data archiving engine 1434 may also archive the user active treatment parameter data 1412 to capture the treatment parameters, prior to adjustment, as user historic treatment parameter data 1436. The adjusted treatment parameters, further, may be added or replace the prior version of the user active treatment parameter data 1412 corresponding to the subject neurostimulation system 1404.

In some implementations, the user data archiving engine 1434 collects the user data stored to the user data store 1410 for archival as corresponding user historic treatment parameter data 1436, user historic treatment feedback data 1440, and/or user historic treatment contextual data 1442. The user data archiving engine 1434, in some embodiments, de-identifies at least a portion of the archived user data 1436, 1440, and/or 1442 for use in big data analysis across multiple users of neurostimulation systems 1404.

In some implementations, in addition to automatically acquired sensor data and/or contextual data, a user feedback collection engine 1444 collects information from wearers of the neurostimulation systems 1404 and/or clinicians working with the wearers regarding the experience of using the neurostimulation system 1404. The user feedback collection engine 1444, for example, may collect user survey data 1446 regarding the wearer's experience during and/or after therapy. For example, the user may have a user interface with the neurostimulation device 1404 and/or a corresponding software application executing on one of the computing devices 1406 to submit feedback regarding the experience. The wearer feedback, in some examples, may include information regarding a stimulation comfort level, an improvement of symptoms level, and/or a comfort of wearing level. The feedback may be provided, in some examples, on a numeric scale or on a descriptor scale that is linked to a numeric scale (e.g., excellent, good, so-so, not great, unpleasant). In another example, the wearer may submit feedback regarding distress (symptoms not improving/seem worse, stimulation causing significant discomfort, etc.) in real-time that the therapy parameter adjustment engine 1432 can take into account when determining adjusted therapeutic parameters.

In some embodiments, the user feedback collection engine 1444 collects clinical observation data 1448 regarding clinicians' experiences in working with patients during therapy and/or who have been prescribed therapy. The clinical observation data 1448, in some examples, may include outcomes information (e.g., reduction or cessation in prescribed medication), diagnosis adjustment information (e.g., severity of a disorder), and/or progress information (e.g., relative recovery of capabilities).

In some embodiments, a therapy model training engine 1450 accesses the archived user historic treatment parameter data 1436, user historic treatment feedback data 1440, user historic treatment contextual data 1442, user survey data 1446 and/or clinical observation data 1448 across a population of wearers of neurostimulation systems 1404 over a period of time (e.g., one month, three months, half a year, one year, etc.) to develop one or more trained learning models 1452. The therapy model training engine 1450, for example, may apply machine learning and/or artificial intelligence to derive promising therapy stimulation parameters and/or routines, such as the therapy stimulation parameters and/or routines 1438. The therapy model training engine 1450, for example, may identify those therapy parameters, treatment schedules, and/or contextual parameters (e.g., setting, timing, etc.) associated with successful treatment. The trained learning models 1452 may include one or more models per treatment type (e.g., therapeutic regimen directed to treat a particular disease, disorder, symptom(s), etc.), per diagnoses (e.g., comorbidity such as smoking status, mental health diagnosis such as depression or PTSD), and/or per user demographic (e.g., age, gender, etc.), and/or per user type (e.g., military, athlete, etc.). The trained learning models 1452, for example, may be designed predict, based on user demographics 1424, user medical condition(s) 1426, and/or user clinical data 1428, beneficial therapy stimulation parameters and/or routines 1438 for the particular patient.

In some implementations, after initially training the trained learning models 1452, upon collecting further user historic data 1436, 1440, and/or 1442, user survey data 1446, and/or clinical observation data 1448, a therapy model refining engine 1454 updates the trained learning models 1452 using the new learning data. The therapy model refining engine 1454, for example, may refine the trained learning models 1452 on a periodic basis or ongoing as new data is collected by the sensor data analytics system 1402.

Although the sensor data analytics system 1402 is illustrated as being separate from the neurostimulation system 1404, in some embodiments, portions of the sensor data analytics system 1402 is included within the neurostimulation system 1404 and/or in a computing device 1406 in direct (e.g., wired or short rage wireless transmission range, etc.) communication with the neurostimulation system 1404. For example, to swiftly adapt ongoing neurostimulation therapy based on sensor feedback, portions of the functionality of the therapy data analysis engine 1420 may execute in real-time or near real-time on equipment local to the wearer.

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors, for example on one or more physical computing systems such as a computer farm or a cloud drive.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations. The hardware logic may be synthesized on a reprogrammable computing chip such as a field programmable gate array (FPGA), programmable logic device (PLD), or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the pulse generator 950 of FIG. 9, the system 1360 of FIG. 13, and/or the sensor data analytics system 1402 of FIG. 14 to perform various methods and algorithms described above. Further, the processing circuitry and stored instructions may enable the peripheral device(s) 1354, 1390 of FIG. 13 to perform various methods and algorithms described above.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi, Bluetooth, Zigbee, or another wireless form of communication.

The computing device, such as the peripheral device(s) 1354, 1390 of FIG. 13, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display.

A sound controller, in some embodiments, is also provided in the computing device, such as the peripheral device(s) 1354, 1390 of FIG. 13, to interface with speakers/microphone thereby providing audio input and output.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Certain functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™, may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google Cloud Storage, may store processed and unprocessed data supplied by systems described herein.

The systems described herein may communicate with the cloud computing environment through a secure gateway. In some implementations, the secure gateway includes a database querying interface, such as the Google BigQuery platform.

In some implementations, an edge server is used to transfer data between one or more computing devices and a cloud computing environment according to various embodiments described herein. The edge server, for example, may be a computing device configured to execute processor intensive operations that are sometimes involved when executing machine learning processes, such as natural language processing operations. An edge server may include, for example, one or more GPUs that are capable of efficiently executing matrix operations as well as substantial cache or other high-speed memory to service the GPUs. An edge server may be a standalone physical device. An edge server may be incorporated into other computing equipment, such as a laptop computer, tablet computer, medical device, or other specialized computing device. Alternatively or additionally, an edge server may be located within a carrying case for such computing equipment. An edge server, in a further example, may be incorporated into the communications and processing capabilities of a mobile unit such as a vehicle or drone, or may otherwise be located within the mobile unit.

In some implementations, the edge server communicates with one or more local devices to the edge server. The edge server, for example, can be used to move a portion of the computing capability traditionally shifted to a cloud computing environment into the local environment so that any computation intensive data processing and/or analytics required by the one or more local devices can run accurately and efficiently. In some embodiments, the edge server is used to support the one or more local devices in the absence of a connection with a remote computing environment. The edge server may be configured to communicate with the one or more local devices directly or via a network. For instance, the edge server can include a private wireless network interface, a public wireless network interface, and/or a wired interface through which the edge server can communicate with the one or more local devices. In some embodiments, certain local devices may be configured to communicate indirectly with the edge server, for example via another local device. Further, the edge server may be configured to communicate with a remote computing (e.g., cloud) environment via one or more public or private wireless network interfaces. The device interoperating with the edge server, for example, may share processing functionality with the edge server via one or more APIs implemented by the processes.

The systems described herein may include one or more artificial intelligence (AI) neural networks for performing automated analysis of data. The AI neural networks, in some examples, can include a synaptic neural network, a deep neural network, a transformer neural network, and/or a generative adversarial network (GAN). The AI neural networks may be trained using one or more machine learning techniques and/or classifiers such as, in some examples, anomaly detection, clustering, and/or supervised and/or association. In one example, the AI neural networks may be developed and/or based on a bidirectional encoder representations for transformers (BERT) model by Google of Mountain View, CA.

The systems described herein may communicate with one or more foundational model systems (e.g., artificial intelligence neural networks). The foundational model system(s), in some examples, may be developed, trained, tuned, fine-tuned, and/or prompt engineered to evaluate data inputs such as sensor inputs collected by the system 1360 and/or the sensor data analytics system 1352 of FIG. 13 and/or sensor inputs collected by the sensor data analytics system 1402 of FIG. 14. The foundational model systems, in some examples, may include or be based off of the generative pre-trained transformer (GPT) models available via the OpenAI platform by OpenAI of San Francisco, CA (e.g., GPT-3, GPT-3.5, and/or GPT-4) and/or the generative AI models available through Azure OpenAI or Vertex AI by Google of Mountain View, CA (e.g., PaLM 2).

Certain foundational models may be fine-tuned as AI models trained for performing particular tasks required by the systems described herein. Training material, for example, may be submitted to certain foundational models to adjust the training of the foundational model for performing types of analyses described herein.

Multiple foundational model systems may be applied by the systems and methods described herein depending on context. The context, for example, may include type(s) of data, type(s) of response output desired (e.g., at least one answer, at least one answer plus an explanation regarding the reasoning that lead to the answer(s), etc.). In another example, the context can include user-based context such as demographic information, entity information, and/or product information. In some embodiments, a single foundational model system may be dynamically adapted to different forms of analyses requested by the systems and methods described herein using prompt engineering.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A method for treating uterine bleeding, the method comprising:

applying, at least once within each forty-eight-hour period of a plurality of consecutive forty-eight-hour periods in which a subject exhibits or is expected to exhibit menstrual bleeding, neurostimulation therapy in one or more sessions, each session of the one or more sessions having a duration of at least five minutes, the neurostimulation therapy being configured to treat uterine bleeding in the subject, wherein applying the neurostimulation therapy comprises applying electrical neurostimulation or mechanical neurostimulation to directly and/or indirectly activate one or more neural targets, the one or more neural targets including at least one of a trigeminal cervical complex (TCC) or vagal efferent fibers (VEF), and the neurostimulation therapy is configured to enhance platelet function of the subject, thereby reducing a total volume of blood loss over a course of the menstrual bleeding wherein enhancing platelet function comprises increasing a baseline ionized calcium concentration in platelets of the subject.

2. The method of claim 1, wherein the subject is diagnosed with abnormal uterine bleeding or heavy menstrual bleeding.

3. The method of claim 2, wherein the subject is diagnosed with a bleeding disorder.

4. The method of claim 1, wherein the neurostimulation therapy is applied at one or more regions of skin of the subject.

5. The method of claim 4, wherein the one or more regions of the skin of the subject are disposed on at least one of a head or a neck of the subject.

6. The method of claim 5, further comprising donning a head-mounted stimulation device, thereby positioning, against each skin region of the one or more regions of skin, a respective stimulation delivery element of one or more stimulation delivery elements.

7. The method of claim 6, wherein the head-mounted stimulation device is an ear-mounted stimulation device.

8. The method of claim 4, wherein applying the electrical neurostimulation at the one or more regions of the skin of the subject comprises applying the electrical neurostimulation via one or more electrodes, each electrode physically contacting a respective region of skin of the one or more regions of skin of the subject.

9. The method of claim 8, wherein the one or more electrodes are percutaneous electrodes.

10. The method of claim 1, wherein the neurostimulation therapy is applied via one or more implanted electrodes.

11. The method of claim 1, wherein indirectly activating the VEF comprises positioning at least one electrical or mechanical stimulation element within neurostimulation delivery range of an auricular branch of a vagus nerve (ABVN) of the subject.

12. The method of claim 1, wherein indirectly activating the TCC comprises positioning at least one electrical or mechanical stimulation element within neurostimulation delivery range of an auriculotemporal nerve (ATN) of the subject.

13. The method of claim 1, wherein the neurostimulation therapy is further configured to generate a vasodilation response in a uterus of the subject, thereby reducing at least one of dysmenorrhea or menstrual cramping.

14. The method of claim 1, wherein the neurostimulation therapy is further configured to activate a Nucleus Tractus Solitari (NTS) via stimulation of vagal and/or trigeminal branches to trigger release of endorphins, thereby modulating pain signals in a central nervous system (CNS) and mitigating pain in the subject.

15. The method of claim 1, further comprising, during a luteal phase of menses, for each respective pre-menstrual session of at least one pre-menstrual session per respective forty-eight hour timeframe of one or more consecutive forty-eight hour timeframes, applying, for a pre-menstrual session length of the respective pre-menstrual session of at least five minutes, the neurostimulation therapy for treating uterine bleeding, thereby preparing the subject with an initial increased baseline of circulating platelets with enhanced platelet function at onset of the uterine bleeding.

16. The method of claim 1, wherein the neurostimulation therapy is applied daily.

17. The method of claim 1, wherein the duration is at least ten minutes.

18. The method of claim 1, wherein the neurostimulation therapy is configured to reduce a total number of bleeding days over the course of the menstrual bleeding.

19. The method of claim 1, wherein the neurostimulation therapy is configured to reduce a total number of hours spent by the subject in bed rest over the course of the menstrual bleeding.

\* \* \* \* \*